(12) United States Patent
Siegel et al.

(10) Patent No.: US 10,149,892 B2
(45) Date of Patent: *Dec. 11, 2018

(54) COMPOSITIONS AND METHODS FOR TREATING CELIAC SPRUE DISEASE

(71) Applicant: UNIVERSITY OF WASHINGTON THROUGH ITS CENTER FOR COMMERCIALIZATION, Seattle, WA (US)

(72) Inventors: Justin Siegel, Seattle, WA (US); David Baker, Seattle, WA (US); Sydney Rin Anna Gordon, Seattle, WA (US); Ingrid Swanson Pultz, Seattle, WA (US); Elizabeth Joy Stanley, Bothell, WA (US); Sarah Jane Wolf, Camas, WA (US)

(73) Assignee: University of Washington Through its Center For Commercialization, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/896,536

(22) Filed: Feb. 14, 2018

(65) Prior Publication Data

US 2018/0185458 A1 Jul. 5, 2018

Related U.S. Application Data

(60) Continuation of application No. 15/633,065, filed on Jun. 26, 2017, now Pat. No. 9,925,249, which is a continuation of application No. 15/006,341, filed on Jan. 26, 2016, now Pat. No. 9,707,280, which is a division of application No. 14/131,601, filed as application No. PCT/US2012/050364 on Aug. 10, 2012, now Pat. No. 9,289,473.

(60) Provisional application No. 61/521,899, filed on Aug. 10, 2011.

(51) Int. Cl.
*A61K 38/48* (2006.01)
*C12N 9/50* (2006.01)
*C12N 9/52* (2006.01)

(52) U.S. Cl.
CPC ............ *A61K 38/482* (2013.01); *A61K 38/48* (2013.01); *C12N 9/50* (2013.01); *C12N 9/52* (2013.01); *C12Y 304/21* (2013.01)

(58) Field of Classification Search
CPC ....................................................... C12N 9/52
See application file for complete search history.

(56) References Cited

U.S. PATENT DOCUMENTS

| | | | |
|---|---|---|---|
| 7,202,216 B2 | 4/2007 | Sollid et al. | |
| 7,265,093 B2 | 9/2007 | Khosla et al. | |
| 7,303,871 B2 | 12/2007 | Hausch et al. | |
| 7,320,788 B2 | 1/2008 | Shan et al. | |
| 7,462,688 B2 | 12/2008 | Khosla et al. | |
| 7,534,426 B2 | 5/2009 | Piper et al. | |
| 7,563,864 B2 | 7/2009 | Marti et al. | |
| 7,579,313 B2 | 8/2009 | Khosla et al. | |
| 7,605,150 B2 | 10/2009 | Khosla et al. | |
| 7,628,985 B2 | 12/2009 | Shan et al. | |
| 7,776,545 B2 | 8/2010 | Khosla et al. | |
| 7,910,541 B2 | 3/2011 | Hausch et al. | |
| 7,923,532 B2 | 4/2011 | Hausch et al. | |
| 7,928,056 B2 | 4/2011 | Hausch et al. | |
| 7,943,312 B2 | 5/2011 | Hausch et al. | |
| 8,071,316 B2 | 12/2011 | Khosla et al. | |
| 8,143,210 B2 | 3/2012 | Shan et al. | |
| 8,153,593 B2 | 4/2012 | Khosla et al. | |
| 8,426,145 B2 | 4/2013 | Khosla et al. | |
| 8,470,782 B2 | 6/2013 | Khosla et al. | |
| 8,796,201 B2 | 8/2014 | Shan et al. | |
| 8,871,718 B2 | 10/2014 | Khosla et al. | |
| 8,962,545 B2 | 2/2015 | Hausch et al. | |
| 2006/0269538 A1 | 11/2006 | Kolterman et al. | |
| 2009/0117092 A1 | 5/2009 | Kappler et al. | |
| 2009/0280555 A1 | 11/2009 | Hausch et al. | |
| 2011/0171201 A1 | 7/2011 | Siegel et al. | |
| 2011/0293724 A1 | 12/2011 | Hausch et al. | |

FOREIGN PATENT DOCUMENTS

| | | |
|---|---|---|
| JP | 2002078489 | 3/2002 |
| WO | 2013/023151 A2 | 2/2013 |
| WO | 2013/083338 A1 | 6/2013 |
| WO | 2015/023728 A1 | 2/2015 |

OTHER PUBLICATIONS

Akobeng, et al., "Systematic review: tolerable amount of gluten for people with coeliac disease," Alimentary Pharmacology & Therapeutics, 27: 1044-1052 (2008).
Arentz-Hansen, et al., "The Intestinal T Cell Response to a-Gliadin in Adult Celiac Disease Is Focused on a Single Deamidated Glutamine Targeted by Tissue Transglutaminase," J. Exp. Med., 191(4): 603-612, 2000.
Armstrong, et al., "Advances in coeliac disease," Curr Opin Gastroenterol 2012, 28:104-112.
Arnold, "Combinatorial and computational challenges for biocatalyst design," Nature, 409: 253-257, Jan. 2001.
Bershtein, et al., "Advances in laboratory evolution of enzymes," Current Opinion in Chemical Biology 2008, 12:151-158.
Bethune, et al., "Heterologous Expression, Purification, Refolding, and Structural-Functional Characterization of EP-B2, a Self-Activating Barley Cysteine Endoprotease," Chemistry & Biology 13, 637-647, Jun. 2006.
Bethune, et al., "Oral Enzyme Therapy for Celiac Sprue," Methods in Enzymology, 502: 241-270, 2012.
Camarca, et al., "Intestinal T Cell Responses to Gluten Peptides Are Largely Heterogeneous: Implications for a Peptide-Based Therapy in Celiac Disease," the Journal of Immunology, 2009, 4158-4166.
Castillo, et al., "The present and the future in the diagnosis and management of celiac disease," Gastroenterology Report, 3(1), 2015, 3-11.

(Continued)

*Primary Examiner* — Suzanne M Noakes
(74) *Attorney, Agent, or Firm* — McDonnell Boehnen Hulbert & Berghoff LLP

(57) ABSTRACT

Disclosed herein are compositions and methods for treating celiac sprue.

38 Claims, 4 Drawing Sheets

Specification includes a Sequence Listing.

(56) References Cited

OTHER PUBLICATIONS

Catassi, et al., "World Perspective and Celiac Disease Epidemiology," Dig Dis 2015;33:141-146.

Catassi, et al., "A prospective, double-blind, placebo-controlled trial to establish a safe gluten threshold for patients with celiac disease," Am J Clin Nutr 2007;85:160-6.

Chand, et al., "Celiac Disease Current Concepts in Diagnosis and Treatment," J Clin Gastroenterol 2006;40:3-14.

Chang, et al., "A Novel Placement Method of the Bravo Wireless pH Monitoring Capsule for Measuring Intragastric pH," Dig Dis Sci (2009) 54:578-585.

Ehern, et al., "A Food-Grade Enzyme Preparation with Modest Gluten Detoxification Properties," PLoS ONE 4(7): e6313. doi:10.1371/journal.pone.0006313, Jul. 2009.

Ehern, et al., "Protein engineering of improved prolyl endopeptidases for celiac sprue therapy," Protein Engineering, Design & Selection vol. 21 No. 12 pp. 699-707, 2008.

Eiben, et al., "Increased Diels-Alderase activity through backbone remodeling guided by Foldit players," Nature Biotechnology, 30(2): 190-194, 2012.

Fleishman, et al., "Computational Design of Proteins Targeting the Conserved Stem Region of Influenza Hemagglutinin," Science, 332:816-821, May 2011.

Gardner, et al., Measurement of meal-stimulated gastric acid secretion by in vivo gastric autotitration, J Appl Physiol 92: 427-434, 2002.

Gass, et al., "Combination Enzyme Therapy for Gastric Digestion of Dietary Gluten in Patients With Celiac Sprue," Gastroenterology 2007;133:472-480.

Gass, et al., "Effect of Barley Endoprotease EP-B2 on Gluten Digestion in the Intact Rat," The Journal of Pharmacology and Experimental Therapeutics vol. 318, No. 3, pp. 1178-1186, 2006.

Gordon, et al., "Computational Design of an α-Gliadin Peptidase," J. Am. Chem. Soc. 2012, 134, 20513-20520.

Hausch, et al., "Intestinal digestive resistance of immunodominant gliadin peptides," Am J Physiol Gastrointest Liver Physiol 283: G996-G1003, 2002.

Houghton, et al., "Relationship of the Motor Activity of the Antrum, Pylorus, and Duodenum to Gastric Emptying of a Solid Liquid Mixed Meal," Gatroenterology, 1988; 94:1285-91.

International Search Report PCT/US2012/050364, dated Apr. 18, 2013.

International Search Report PCT/US2014/050835, dated Dec. 2, 2014.

Kuhlman, et al., "Design of a Novel Globular Protein Fold with Atomic-Level Accuracy," Science, 302: 1364-1368, Nov. 2003.

Kunkel, "Rapid and efficient site-specific mutagenesis without phenotypic selection," Proc. Natl. Acad. Sci. USA vol. 82, pp. 488-492, Jan. 1985.

Lahdeaho, et al., "Glutenase ALV003 Attenuates Gluten-Induced Mucosal Injury in Patients With Celiac Disease," Gastroenterology 2014;146:1649-1658.

Leaver-Fay, et al., "ROSETTA3: An Object-Oriented Software Suite for the Simulation and Design of Macromolecules," Methods in Enzymology, vol. 487:545-574, 2011.

Lupo, et al., "Validation Study of the Veratox R5 Rapid ELISA for Detection of Gliadin," Journal of AOAC International vol. 96, No. 1, 2013.

Moron, et al., "Sensitive detection of cereal fractions that are toxic to celiac disease patients by using monoclonal antibodies to a main immunogenic wheat peptide," Am J Clin Nutr 2008;87:405-14.

Mustalahti, et al., "The prevalence of celiac disease in Europe: Results of a centralized, international mass screening project," Annals of Medicine, 42:8, 587-595, Nov 2010.

Oda, et al., "Subsite Preferences of Pepstatin-Insensitive Carboxyl Proteinases from Prokaryotes: Kumamolysin, a Thermostable Pepstatin-Insensitive Carboxyl Proteinase," J. Biochem. 128,499-607 (2000).

Okubo, et al., "Processing, catalytic activity and crystal structures of kumamolisin-As with an engineered active site," FEBS Journal 273 (2006) 2563-2576.

Oyama, et al., "A CLN2-Related and Thermostable Serine-Carboxyl Proteinase, Kumamolysin: Cloning, Expression, and Identification of Catalytic Serine Residue," J. Biochem. 131, 757-766 (2002).

Pera, et al., "Influence of Mastication on Gastric Emptying," J Dent Res 81(3):179-181, 2002.

Petersen, et al., "T-cell receptor recognition of HLA-DQ2-gliadin complexes associated with celiac disease," Nature Structural & Molecular Biology, 21(5): 480-490, May 2014.

Picariello, et al., "Proteomics, Peptidomics, and Immunogenic Potential of Wheat Beer (Weissbier)," J. Agric. Food Chem. 2015, 63, 3579-3586.

Richter, et al., "De Novo Enzyme Design Using Rosetta3," PLoS ONE 6(5): e19230. doi:10.1371/journal.pone.0019230, May 2011.

Romero, et al., "Exploring protein fitness landscapes by directed evolution," Nature Reviews: Molecular cell Biology, 10: 866-876, Dec. 2009.

Rubio-Tapia, et al., "The Prevalence of Celiac Disease in the United States," Am J Gastroenterol 2012; 107:1538-1544; doi: 10.1038/ajg.2012.219; published online Jul. 31, 2012.

Shan, et al., "Comparative biochemical analysis of three bacterial prolyl endopeptidases: implications for coeliac sprue," Biochem. J. (2004) 383, 311-318.

Shan, et al., "Identification and Analysis of Multivalent Proteolytically Resistant Peptides from Gluten: Implications for Celiac Sprue," Journal of Proteome Research 2005, 4, 1732-1741.

Shan, et al., "Structural Basis for Gluten Intolerance in Celiac Sprue," Science, 297:2275-2279, Sep. 2002.

Siegel, et al., "Rational Design of Combination Enzyme Therapy for Celiac Sprue," Chemistry & Biology 13, 649-658, Jun. 2006.

Siegel, et al., "Safety, Tolerability, and Activity of ALV003: Results from Two Phase 1 Single, Escalating-Dose Clinical Trials," Dig Dis Sci (2012) 57:440-450.

Sollid, et al., "Nomenclature and listing of celiac disease relevant gluten T-cell epitopes restricted by HLA-DQ molecules," Immunogenetics (2012) 64:455-460.

Sollid, et al., "Coeliac Disease: Dissecting a Complex Inflammatory Disorder," Nature Reviews: Immunology, 2:847-855, Sep. 2002.

Stepniak, et al., "Highly efficient gluten degradation with a newly identified prolyl endoprotease: implications for celiac disease," Am J Physiol Gastrointest Liver Physiol 291: G621-G629, May 2006.

Tye-Din, et al., "Comprehensive, Quantitative Mapping of T Cell Epitopes in Gluten in Celiac Disease," Sci Transl Med 2, 41ra51 (2010).

Office Action dated Dec. 23, 2015 in EP 12748354.3.

Ehren, Jennifer, Sridhar Govindarajan, Belâen Morâon, Jeremy Minshull, and Chaitan Khosla. 2008. "Protein engineering of improved prolyl endopeptidases for celiac sprue therapy". Protein Engineering, Design & Selection. 21 (12): 699-707.

Shan L, Ø Molberg, I Parrot, F Hausch, F Filiz, GM Gray, LM Sollid, and C Khosla. 2002. "Structural basis for gluten intolerance in celiac sprue". Science (New York, N.Y.). 297 (5590): 2275-9.

Wlodawer A, M Li, A Gustchina, N Tsuruoka, M Ashida, H Minakata, H Oyama, K Oda, T Nishino, and T Nakayama. 2004. "Crystallographic and biochemical investigations of kumamolisin-As, a serine-carboxyl peptidase with collagenase activity". The Journal of Biological Chemistry. 279 (20): 21500-10.

Vora Harmit, et al., (2007) "A scaleable manufacturing process for pro-EP-B2, a cysteine protease from barley indicated for celiac psrue," Biotechnology and Bioengineering, 98(1): 177-185.

Oyama Hiroshi, et al., (2002) "A CLN2-related and thermostable serine-carboxyl proteinase, kumamolysin: cloning, expression, and identification of catalytic serine residue," Biochemistry, 131(5):757-765.

International Search Report for PCT/US12/50364, dated Apr. 18, 2013.

Vora, et al., "A Scaleable Manufacturing Process for pro-EP-B2, A Cysteine Protease From Barley Indicated for Celiac Sprue," Biotechnology and Bioengineering, vol. 98, No. 1, Sep. 1, 2007.

(56) References Cited

OTHER PUBLICATIONS

Wieser, "Chemistry of gluten proteins," Food Microbiology 24 (2007) 115-119.
Wlodawer, et al., "Crystallographic andBiochemical Investigations of Kumamolisin-As, a Serine-Carboxyl Peptidase with Collagenase Activity," The Journal of Biological Chemistry vol. 279, No. 20, Issue of May 14, pp. 21500-21510, 2004.
Arentz-Hansen et al. (Sep. 2002) "Celiac lesion T cells recognize epitopes that cluster in regions of gliadins rich in proline residues," Gastroenterology, 123(3):803-809.
Siegel et al. (Jul. 2010) "Computational Design of an Enzyme Catalyst for a Stereoselective Bimolecular Diels-Alder Reaction," Science, 329(5989):309-313.
UniProt C8WU40—Retrieved from < http://www.uniprot.org/uniprot/C8WU40 >on Jan. 29, 2015.
Mustalahti K, C Catassi, A Reunanen, E Fabiani, M Heier, S McMillan, L Murray, et al. 2010. "The prevalence of celiac disease in Europe: results of a centralized, international mass screening project". Annals of Medicine. 42 (8): 587-95.
Cornellas-Bigler, et al., "1.2 A crystal structure of the serine carboxyl porteinase pro-kumamolisin: structure of an intact pro-subtilase," Structure, 12: 1313-1323, Jul. 2004.
Dunn, et al., "Engineered Enzyme," Encyclopedia of Life Sciences, 2005, p. 1-8.
Genbank: ACV57803.1, Peptidase S53 propeptide, Sep. 2009.
GenBank: BAC41257.1, kumamolisin-As precursor, Jun. 2003.
GenBank: 1SIO_A, Chain A, Structure of Kumamolisin-As Complex, Sep. 2008.
International Search Report and Written Opinion for PCT/US2016/036356, dated Aug. 10, 2016.
Database Uniparc, XP002760283, Jan. 15, 2010.
Wolf, et al., "Engineering of Kuma 030: A Gliadin peptidase that rapidly degrades immunogenic gliadin peptides in gastric conditions," Journal of the American Chemical Society, 137(40): 13106-13113, Oct. 2015.

SEQUENCE LISTING

```
<160> NUMBER OF SEQ ID NOS: 73

<210> SEQ ID NO 1
<211> LENGTH: 573
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (119)..(119)
<223> OTHER INFORMATION: X can be V or D
<220> FEATURE:
<221> NAME/KEY: MISC_FEATURE
<222> LOCATION: (262)..(262)
<223> OTHER INFORMATION: X can be S, K or G
<220> FEATURE:
<221> NAME/KEY: MISC_FEATURE
<222> LOCATION: (291)..(291)
<223> OTHER INFORMATION: X can be N or D
<220> FEATURE:
<221> NAME/KEY: MISC_FEATURE
<222> LOCATION: (292)..(292)
<223> OTHER INFORMATION: X can be T or S
<220> FEATURE:
<221> NAME/KEY: MISC_FEATURE
<222> LOCATION: (293)..(293)
<223> OTHER INFORMATION: X can be D, A, T, or N
<220> FEATURE:
<221> NAME/KEY: MISC_FEATURE
<222> LOCATION: (319)..(319)
<223> OTHER INFORMATION: X can be G or S
<220> FEATURE:
<221> NAME/KEY: MISC_FEATURE
<222> LOCATION: (354)..(354)
<223> OTHER INFORMATION: X can be S or N
<220> FEATURE:
<221> NAME/KEY: MISC_FEATURE
<222> LOCATION: (357)..(357)
<223> OTHER INFORMATION: X can be T or A
<220> FEATURE:
<221> NAME/KEY: MISC_FEATURE
<222> LOCATION: (358)..(358)
<223> OTHER INFORMATION: X can be D, N or G
<220> FEATURE:
<221> NAME/KEY: MISC_FEATURE
<222> LOCATION: (361)..(361)
<223> OTHER INFORMATION: X can be Q or D
<220> FEATURE:
<221> NAME/KEY: MISC_FEATURE
<222> LOCATION: (368)..(368)
<223> OTHER INFORMATION: X can be D, S, or H

<400> SEQUENCE: 1

Met Ser Asp Met Glu Lys Pro Trp Lys Glu Gly Glu Glu Ala Arg Ala
1               5                   10                  15

Val Leu Gln Gly His Ala Arg Ala Gln Ala Pro Gln Ala Val Asp Lys
            20                  25                  30
```

```
Gly Pro Val Ala Gly Asp Glu Arg Met Ala Val Thr Val Leu Arg
         35                  40                  45

Arg Gln Arg Ala Gly Glu Leu Ala Ala His Val Glu Arg Gln Ala Ala
     50                  55                  60

Ile Ala Pro His Ala Arg Glu His Leu Lys Arg Glu Ala Phe Ala Ala
 65                  70                  75                  80

Ser His Gly Ala Ser Leu Asp Asp Phe Ala Glu Leu Arg Arg Phe Ala
                 85                  90                  95

Asp Ala His Gly Leu Ala Leu Asp Arg Ala Asn Val Ala Ala Gly Thr
                100                 105                 110

Ala Val Leu Ser Gly Pro Xaa Asp Ala Ile Asn Arg Ala Phe Gly Val
             115                 120                 125

Glu Leu Arg His Phe Asp His Pro Asp Gly Ser Tyr Arg Ser Tyr Leu
         130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
                180                 185                 190

Thr Ala Tyr Thr Pro Leu Asp Val Ala Gln Ala Tyr Gln Phe Pro Glu
            195                 200                 205

Gly Leu Asp Gly Gln Gly Gln Cys Ile Ala Ile Ile Glu Leu Gly Gly
        210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Xaa Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Xaa Xaa Xaa Ala Gly Phe Leu Asp Ala Ile Thr Thr Ala Ile
290                 295                 300

His Asp Pro Thr Leu Lys Pro Ser Val Val Ser Ile Ser Trp Xaa Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Xaa Gly Ser Xaa Xaa Gly Glu Xaa Asp Gly Leu Tyr His Val Xaa
        355                 360                 365

Phe Pro Ala Ala Ser Pro Tyr Val Leu Ala Cys Gly Gly Thr Arg Leu
370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro
        435                 440                 445
```

```
Ala Thr Gly Tyr Glu Val Val Ile Asp Gly Glu Ala Thr Val Ile Gly
        450                 455                 460
Gly Thr Ser Ala Val Ala Pro Leu Phe Ala Ala Leu Val Ala Arg Ile
465                 470                 475                 480
Asn Gln Lys Leu Gly Lys Ala Val Gly Tyr Leu Asn Pro Thr Leu Tyr
                485                 490                 495
Gln Leu Pro Ala Asp Val Phe His Asp Ile Thr Glu Gly Asn Asn Asp
            500                 505                 510
Ile Ala Asn Arg Ala Gln Ile Tyr Gln Ala Gly Pro Gly Trp Asp Pro
        515                 520                 525
Cys Thr Gly Leu Gly Ser Pro Ile Gly Val Arg Leu Leu Gln Ala Leu
    530                 535                 540
Leu Pro Ser Ala Ser Gln Pro Gln Pro Gly Ser Thr Glu Asn Leu Tyr
545                 550                 555                 560
Phe Gln Ser Gly Ala Leu Glu His His His His His
                565                 570
```

<210> SEQ ID NO 2
<211> LENGTH: 573
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (119)..(119)
<223> OTHER INFORMATION: X can be V or D
<220> FEATURE:
<221> NAME/KEY: MISC_FEATURE
<222> LOCATION: (262)..(262)
<223> OTHER INFORMATION: X can be S, K or G
<220> FEATURE:
<221> NAME/KEY: MISC_FEATURE
<222> LOCATION: (291)..(291)
<223> OTHER INFORMATION: All mutants with more than 10-fold activity
      have this substitution
<220> FEATURE:
<221> NAME/KEY: MISC_FEATURE
<222> LOCATION: (292)..(292)
<223> OTHER INFORMATION: X can be T or S
<220> FEATURE:
<221> NAME/KEY: MISC_FEATURE
<222> LOCATION: (293)..(293)
<223> OTHER INFORMATION: X can be D, A, T or N
<220> FEATURE:
<221> NAME/KEY: MISC_FEATURE
<222> LOCATION: (319)..(319)
<223> OTHER INFORMATION: X can be G or S
<220> FEATURE:
<221> NAME/KEY: MISC_FEATURE
<222> LOCATION: (354)..(354)
<223> OTHER INFORMATION: X can be S or N
<220> FEATURE:
<221> NAME/KEY: MISC_FEATURE
<222> LOCATION: (357)..(357)
<223> OTHER INFORMATION: X can be T or A
<220> FEATURE:
<221> NAME/KEY: MISC_FEATURE
<222> LOCATION: (358)..(358)
<223> OTHER INFORMATION: X can be D, N or G
<220> FEATURE:
<221> NAME/KEY: MISC_FEATURE
<222> LOCATION: (361)..(361)
<223> OTHER INFORMATION: X can be Q or D
<220> FEATURE:
<221> NAME/KEY: MISC_FEATURE
<222> LOCATION: (368)..(368)
<223> OTHER INFORMATION: X can be D, S or H

<400> SEQUENCE: 2

```
Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Val Leu Arg
                35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Xaa Asp Ala Ile Asn Arg Ala Phe Gly Val
            115                 120                 125

Glu Leu Arg His Phe Asp His Pro Asp Gly Ser Tyr Arg Ser Tyr Leu
        130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Tyr Gln Phe Pro Glu
        195                 200                 205

Gly Leu Asp Gly Gln Gly Gln Cys Ile Ala Ile Ile Glu Leu Gly Gly
        210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Xaa Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asp Xaa Xaa Ala Gly Phe Leu Asp Ala Ile Thr Thr Ala Ile
        290                 295                 300

His Asp Pro Thr Leu Lys Pro Ser Val Val Ser Ile Ser Trp Xaa Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Xaa Gly Ser Xaa Xaa Gly Glu Xaa Asp Gly Leu Tyr His Val Xaa
        355                 360                 365

Phe Pro Ala Ala Ser Pro Tyr Val Leu Ala Cys Gly Gly Thr Arg Leu
        370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
```

```
                420             425             430
Ala Ser Ser Gly Arg Gly Val Pro Asp Leu Ala Gly Asn Ala Asp Pro
            435             440             445

Ala Thr Gly Tyr Glu Val Val Ile Asp Gly Glu Ala Thr Val Ile Gly
    450             455             460

Gly Thr Ser Ala Val Ala Pro Leu Phe Ala Ala Leu Val Ala Arg Ile
465             470             475             480

Asn Gln Lys Leu Gly Lys Ala Val Gly Tyr Leu Asn Pro Thr Leu Tyr
            485             490             495

Gln Leu Pro Ala Asp Val Phe His Asp Ile Thr Glu Gly Asn Asn Asp
        500             505             510

Ile Ala Asn Arg Ala Gln Ile Tyr Gln Ala Gly Pro Gly Trp Asp Pro
        515             520             525

Cys Thr Gly Leu Gly Ser Pro Ile Gly Val Arg Leu Leu Gln Ala Leu
    530             535             540

Leu Pro Ser Ala Ser Gln Pro Gln Pro Gly Ser Thr Glu Asn Leu Tyr
545             550             555             560

Phe Gln Ser Gly Ala Leu Glu His His His His His His
            565             570
```

```
<210> SEQ ID NO 3
<211> LENGTH: 573
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (119)..(119)
<223> OTHER INFORMATION: X can be V or D
<220> FEATURE:
<221> NAME/KEY: MISC_FEATURE
<222> LOCATION: (262)..(262)
<223> OTHER INFORMATION: X can be S, K, or G
<220> FEATURE:
<221> NAME/KEY: MISC_FEATURE
<222> LOCATION: (291)..(291)
<223> OTHER INFORMATION: All mutants with more than 20-fold activity
      increase have this substitution together with 358 substitution
<220> FEATURE:
<221> NAME/KEY: MISC_FEATURE
<222> LOCATION: (292)..(292)
<223> OTHER INFORMATION: X is T or S
<220> FEATURE:
<221> NAME/KEY: MISC_FEATURE
<222> LOCATION: (293)..(293)
<223> OTHER INFORMATION: X is D, A, T or N
<220> FEATURE:
<221> NAME/KEY: MISC_FEATURE
<222> LOCATION: (319)..(319)
<223> OTHER INFORMATION: X is G or S
<220> FEATURE:
<221> NAME/KEY: MISC_FEATURE
<222> LOCATION: (354)..(354)
<223> OTHER INFORMATION: X is S or N
<220> FEATURE:
<221> NAME/KEY: MISC_FEATURE
<222> LOCATION: (357)..(357)
<223> OTHER INFORMATION: X is T or A
<220> FEATURE:
<221> NAME/KEY: MISC_FEATURE
<222> LOCATION: (358)..(358)
<223> OTHER INFORMATION: X is N or G (most have G at this position)
<220> FEATURE:
<221> NAME/KEY: MISC_FEATURE
<222> LOCATION: (361)..(361)
<223> OTHER INFORMATION: X is Q or D
<220> FEATURE:
<221> NAME/KEY: MISC_FEATURE
```

<222> LOCATION: (368)..(368)
<223> OTHER INFORMATION: X is D, S, or H

<400> SEQUENCE: 3

```
Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Val Leu Arg
                35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Xaa Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Xaa Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asp Xaa Xaa Ala Gly Phe Leu Asp Ala Ile Thr Thr Ala Ile
    290                 295                 300

His Asp Pro Thr Leu Lys Pro Ser Val Val Ser Ile Ser Trp Xaa Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Xaa Gly Ser Xaa Xaa Gly Glu Xaa Asp Gly Leu Tyr His Val Xaa
        355                 360                 365

Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Asp Gly
385                 390                 395                 400
```

```
Pro Asp Gly Gly Ala Thr Gly Gly Val Ser Arg Ile Phe Pro Leu
            405                 410                 415

Pro Ala Trp Gln Glu His Ala Asn Val Pro Pro Ser Ala Asn Pro Gly
        420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
    450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
    530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His His
                565                 570
```

<210> SEQ ID NO 4
<211> LENGTH: 573
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (119)..(119)
<223> OTHER INFORMATION: X is V or D
<220> FEATURE:
<221> NAME/KEY: MISC_FEATURE
<222> LOCATION: (262)..(262)
<223> OTHER INFORMATION: X is S, K or G
<220> FEATURE:
<221> NAME/KEY: MISC_FEATURE
<222> LOCATION: (291)..(291)
<223> OTHER INFORMATION: All mutants with more than 50-fold activity
      increase have this substitution together with 319, 358, and 368
      substitutions
<220> FEATURE:
<221> NAME/KEY: MISC_FEATURE
<222> LOCATION: (292)..(292)
<223> OTHER INFORMATION: X is T or S
<220> FEATURE:
<221> NAME/KEY: MISC_FEATURE
<222> LOCATION: (293)..(293)
<223> OTHER INFORMATION: X is D, A, T, or N
<220> FEATURE:
<221> NAME/KEY: MISC_FEATURE
<222> LOCATION: (354)..(354)
<223> OTHER INFORMATION: X is S or N
<220> FEATURE:
<221> NAME/KEY: MISC_FEATURE
<222> LOCATION: (357)..(357)
<223> OTHER INFORMATION: X is T or A
<220> FEATURE:
<221> NAME/KEY: MISC_FEATURE
<222> LOCATION: (361)..(361)
<223> OTHER INFORMATION: X is Q or D

<400> SEQUENCE: 4

Met Ser Asp Met Glu Lys Pro Trp Lys Glu Gly Glu Glu Ala Arg Ala

-continued

```
1               5                   10                  15
Val Leu Gln Gly His Ala Arg Ala Gln Ala Pro Gln Ala Val Asp Lys
                20                  25                  30
Gly Pro Val Ala Gly Asp Glu Arg Met Ala Val Thr Val Val Leu Arg
                35                  40                  45
Arg Gln Arg Ala Gly Glu Leu Ala Ala His Val Glu Arg Gln Ala Ala
     50                  55                  60
Ile Ala Pro His Ala Arg Glu His Leu Lys Arg Glu Ala Phe Ala Ala
 65                  70                  75                  80
Ser His Gly Ala Ser Leu Asp Asp Phe Ala Glu Leu Arg Arg Phe Ala
                85                  90                  95
Asp Ala His Gly Leu Ala Leu Asp Arg Ala Asn Val Ala Ala Gly Thr
                100                 105                 110
Ala Val Leu Ser Gly Pro Xaa Asp Ala Ile Asn Arg Ala Phe Gly Val
                115                 120                 125
Glu Leu Arg His Phe Asp His Pro Asp Gly Ser Tyr Arg Ser Tyr Leu
            130                 135                 140
Gly Glu Val Thr Val Pro Ala Ser Ile Ala Pro Met Ile Glu Ala Val
145                 150                 155                 160
Leu Gly Leu Asp Thr Arg Pro Val Ala Arg Pro His Phe Arg Met Gln
                165                 170                 175
Arg Arg Ala Glu Gly Gly Phe Glu Ala Arg Ser Gln Ala Ala Ala Pro
            180                 185                 190
Thr Ala Tyr Thr Pro Leu Asp Val Ala Gln Ala Tyr Gln Phe Pro Glu
            195                 200                 205
Gly Leu Asp Gly Gln Gly Gln Cys Ile Ala Ile Ile Glu Leu Gly Gly
210                 215                 220
Gly Tyr Asp Glu Ala Ser Leu Ala Gln Tyr Phe Ala Ser Leu Gly Val
225                 230                 235                 240
Pro Ala Pro Gln Val Val Ser Val Ser Val Asp Gly Ala Ser Asn Gln
                245                 250                 255
Pro Thr Gly Asp Pro Xaa Gly Pro Asp Gly Glu Val Glu Leu Asp Ile
            260                 265                 270
Glu Val Ala Gly Ala Leu Ala Pro Gly Ala Lys Phe Ala Val Tyr Phe
        275                 280                 285
Ala Pro Asp Xaa Xaa Ala Gly Phe Leu Asp Ala Ile Thr Thr Ala Ile
        290                 295                 300
His Asp Pro Thr Leu Lys Pro Ser Val Val Ser Ile Ser Trp Ser Gly
305                 310                 315                 320
Pro Glu Asp Ser Trp Thr Ser Ala Ala Ile Ala Ala Met Asn Arg Ala
                325                 330                 335
Phe Leu Asp Ala Ala Leu Gly Val Thr Val Leu Ala Ala Ala Gly
            340                 345                 350
Asp Xaa Gly Ser Xaa Gly Gly Glu Xaa Asp Gly Leu Tyr His Val His
            355                 360                 365
Phe Pro Ala Ala Ser Pro Tyr Val Leu Ala Cys Gly Gly Thr Arg Leu
    370                 375                 380
Val Ala Ser Gly Gly Arg Ile Ala Gln Glu Thr Val Trp Asn Asp Gly
385                 390                 395                 400
Pro Asp Gly Gly Ala Thr Gly Gly Val Ser Arg Ile Phe Pro Leu
            405                 410                 415
Pro Ala Trp Gln Glu His Ala Asn Val Pro Ser Ala Asn Pro Gly
            420                 425                 430
```

```
Ala Ser Ser Gly Arg Gly Val Pro Asp Leu Ala Gly Asn Ala Asp Pro
        435                 440                 445

Ala Thr Gly Tyr Glu Val Val Ile Asp Gly Glu Ala Thr Val Ile Gly
    450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
515                 520                 525

Cys Thr Gly Leu Gly Ser Pro Ile Gly Val Arg Leu Leu Gln Ala Leu
            530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His
                565                 570

<210> SEQ ID NO 5
<211> LENGTH: 573
<212> TYPE: PRT
<213> ORGANISM: Artificial Sequence
<220> FEATURE:
<223> OTHER INFORMATION: Synthetic

<400> SEQUENCE: 5

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Val Leu Arg
            35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220
```

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
            245                 250                 255

Pro Thr Gly Asp Pro Ser Gly Pro Asp Gly Glu Val Glu Leu Asp Ile
            260                 265                 270

Glu Val Ala Gly Ala Leu Ala Pro Gly Ala Lys Phe Ala Val Tyr Phe
            275                 280                 285

Ala Pro Asn Thr Asp Ala Gly Phe Leu Asp Ala Ile Thr Thr Ala Ile
            290                 295                 300

His Asp Pro Thr Leu Lys Pro Ser Val Val Ser Ile Ser Trp Gly Gly
305                 310                 315                 320

Pro Glu Asp Ser Trp Thr Ser Ala Ala Ile Ala Ala Met Asn Arg Ala
                325                 330                 335

Phe Leu Asp Ala Ala Leu Gly Val Thr Val Leu Ala Ala Ala Gly
                340                 345                 350

Asp Ser Gly Ser Thr Asn Gly Glu Gln Asp Gly Leu Tyr His Val Asp
            355                 360                 365

Phe Pro Ala Ala Ser Pro Tyr Val Leu Ala Cys Gly Gly Thr Arg Leu
370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
            405                 410                 415

Pro Ala Trp Gln Glu His Ala Asn Val Pro Pro Ser Ala Asn Pro Gly
                420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
            450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
            530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His
                565                 570

<210> SEQ ID NO 6
<211> LENGTH: 573
<212> TYPE: PRT
<213> ORGANISM: Artificial Sequence
<220> FEATURE:
<223> OTHER INFORMATION: Synthetic

<400> SEQUENCE: 6

Met Ser Asp Met Glu Lys Pro Trp Lys Glu Gly Glu Glu Ala Arg Ala
1               5                   10                  15

```
Val Leu Gln Gly His Ala Arg Ala Gln Ala Pro Gln Ala Val Asp Lys
             20                  25                  30

Gly Pro Val Ala Gly Asp Glu Arg Met Ala Val Thr Val Leu Arg
         35                  40                  45

Arg Gln Arg Ala Gly Glu Leu Ala Ala His Val Glu Arg Gln Ala Ala
 50                  55                  60

Ile Ala Pro His Ala Arg Glu His Leu Lys Arg Glu Ala Phe Ala Ala
 65                  70                  75                  80

Ser His Gly Ala Ser Leu Asp Asp Phe Ala Glu Leu Arg Arg Phe Ala
                 85                  90                  95

Asp Ala His Gly Leu Ala Leu Asp Arg Ala Asn Val Ala Ala Gly Thr
             100                 105                 110

Ala Val Leu Ser Gly Pro Val Asp Ala Ile Asn Arg Ala Phe Gly Val
         115                 120                 125

Glu Leu Arg His Phe Asp His Pro Asp Gly Ser Tyr Arg Ser Tyr Leu
130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                 165                 170                 175

Arg Arg Ala Glu Gly Gly Phe Glu Ala Arg Ser Gln Ala Ala Ala Pro
             180                 185                 190

Thr Ala Tyr Thr Pro Leu Asp Val Ala Gln Ala Tyr Gln Phe Pro Glu
         195                 200                 205

Gly Leu Asp Gly Gln Gly Gln Cys Ile Ala Ile Ile Glu Leu Gly Gly
210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                 245                 250                 255

Pro Thr Gly Asp Pro Ser Gly Pro Asp Gly Glu Val Glu Leu Asp Ile
             260                 265                 270

Glu Val Ala Gly Ala Leu Ala Pro Gly Ala Lys Phe Ala Val Tyr Phe
         275                 280                 285

Ala Pro Asp Thr Asp Ala Gly Phe Leu Asp Ala Ile Thr Thr Ala Ile
290                 295                 300

His Asp Pro Thr Leu Lys Pro Ser Val Val Ser Ile Ser Trp Gly Gly
305                 310                 315                 320

Pro Glu Asp Ser Trp Thr Ser Ala Ala Ile Ala Ala Met Asn Arg Ala
                 325                 330                 335

Phe Leu Asp Ala Ala Leu Gly Val Thr Val Leu Ala Ala Ala Gly
             340                 345                 350

Asp Ser Gly Ser Thr Asp Gly Glu Gln Asp Gly Leu Tyr His Val Asp
         355                 360                 365

Phe Pro Ala Ala Ser Pro Tyr Val Leu Ala Cys Gly Gly Thr Arg Leu
370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
             405                 410                 415

Pro Ala Trp Gln Glu His Ala Asn Val Pro Ser Ala Asn Pro Gly
             420                 425                 430
```

```
Ala Ser Ser Gly Arg Gly Val Pro Asp Leu Ala Gly Asn Ala Asp Pro
        435                 440                 445

Ala Thr Gly Tyr Glu Val Val Ile Asp Gly Glu Ala Thr Val Ile Gly
    450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
515                 520                 525

Cys Thr Gly Leu Gly Ser Pro Ile Gly Val Arg Leu Leu Gln Ala Leu
    530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His His
                565                 570
```

<210> SEQ ID NO 7
<211> LENGTH: 573
<212> TYPE: PRT
<213> ORGANISM: Artificial Sequence
<220> FEATURE:
<223> OTHER INFORMATION: Synthetic

<400> SEQUENCE: 7

```
Met Ser Asp Met Glu Lys Pro Trp Lys Glu Gly Glu Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220
```

```
Gly Tyr Asp Glu Ala Ser Leu Ala Gln Tyr Phe Ala Ser Leu Gly Val
225                 230                 235                 240

Pro Ala Pro Gln Val Ser Val Ser Val Asp Gly Ala Ser Asn Gln
            245                 250                 255

Pro Thr Gly Asp Pro Ser Gly Pro Asp Gly Glu Val Glu Leu Asp Ile
            260                 265                 270

Glu Val Ala Gly Ala Leu Ala Pro Gly Ala Lys Phe Ala Val Tyr Phe
            275                 280                 285

Ala Pro Asn Thr Asp Ala Gly Phe Leu Asp Ala Ile Thr Thr Ala Ile
            290                 295                 300

His Asp Pro Thr Leu Lys Pro Ser Val Val Ser Ile Ser Trp Gly Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
                340                 345                 350

Asp Ser Gly Ser Thr Gly Gly Glu Gln Asp Gly Leu Tyr His Val Asp
                355                 360                 365

Phe Pro Ala Ala Ser Pro Tyr Val Leu Ala Cys Gly Gly Thr Arg Leu
            370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Ser Ala Asn Pro Gly
            420                 425                 430

Ala Ser Ser Gly Arg Gly Val Pro Asp Leu Ala Gly Asn Ala Asp Pro
                435                 440                 445

Ala Thr Gly Tyr Glu Val Val Ile Asp Gly Glu Ala Thr Val Ile Gly
            450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His
                565                 570

<210> SEQ ID NO 8
<211> LENGTH: 573
<212> TYPE: PRT
<213> ORGANISM: Artificial Sequence
<220> FEATURE:
<223> OTHER INFORMATION: Synthetic

<400> SEQUENCE: 8

Met Ser Asp Met Glu Lys Pro Trp Lys Glu Gly Glu Glu Ala Arg Ala
1               5                   10                  15
```

-continued

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Leu Arg
         35                  40                  45

Arg Gln Arg Ala Gly Glu Leu Ala Ala His Val Glu Arg Gln Ala Ala
     50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
            115                 120                 125

Glu Leu Arg His Phe Asp His Pro Asp Gly Ser Tyr Arg Ser Tyr Leu
        130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
            195                 200                 205

Gly Leu Asp Gly Gln Gly Gln Cys Ile Ala Ile Ile Glu Leu Gly Gly
        210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Ser Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asn Thr Asp Ala Gly Phe Leu Asp Ala Ile Thr Thr Ala Ile
        290                 295                 300

His Asp Pro Thr Leu Lys Pro Ser Val Val Ser Ile Ser Trp Gly Gly
305                 310                 315                 320

Pro Glu Asp Ser Trp Thr Ser Ala Ala Ile Ala Ala Met Asn Arg Ala
                325                 330                 335

Phe Leu Asp Ala Ala Leu Gly Val Thr Val Leu Ala Ala Ala Gly
            340                 345                 350

Asp Ser Gly Ser Ala Asp Gly Glu Gln Asp Gly Leu Tyr His Val Asp
            355                 360                 365

Phe Pro Ala Ala Ser Pro Tyr Val Leu Ala Cys Gly Gly Thr Arg Leu
        370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro

```
            435                 440                 445
Ala Thr Gly Tyr Glu Val Val Ile Asp Gly Glu Ala Thr Val Ile Gly
        450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
        530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His His
                565                 570
```

<210> SEQ ID NO 9
<211> LENGTH: 573
<212> TYPE: PRT
<213> ORGANISM: Artificial Sequence
<220> FEATURE:
<223> OTHER INFORMATION: Synthetic

<400> SEQUENCE: 9

```
Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Leu Arg
            35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
```

```
                225                 230                 235                 240
Pro Ala Pro Gln Val Ser Val Ser Val Asp Gly Ala Ser Asn Gln
                245                 250                 255

Pro Thr Gly Asp Pro Ser Gly Pro Asp Gly Glu Val Glu Leu Asp Ile
            260                 265                 270

Glu Val Ala Gly Ala Leu Ala Pro Gly Ala Lys Phe Ala Val Tyr Phe
                275                 280                 285

Ala Pro Asn Thr Ala Ala Gly Phe Leu Asp Ala Ile Thr Thr Ala Ile
            290                 295                 300

His Asp Pro Thr Leu Lys Pro Ser Val Val Ser Ile Ser Trp Gly Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
                340                 345                 350

Asp Ser Gly Ser Thr Asp Gly Glu Gln Asp Gly Leu Tyr His Val Asp
            355                 360                 365

Phe Pro Ala Ala Ser Pro Tyr Val Leu Ala Cys Gly Gly Thr Arg Leu
            370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
        450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
        530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His
                565                 570

<210> SEQ ID NO 10
<211> LENGTH: 573
<212> TYPE: PRT
<213> ORGANISM: Artificial Sequence
<220> FEATURE:
<223> OTHER INFORMATION: Synthetic

<400> SEQUENCE: 10

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
```

```
            20                  25                  30
Gly Pro Val Ala Gly Asp Glu Arg Met Ala Val Thr Val Leu Arg
            35                  40                  45
Arg Gln Arg Ala Gly Glu Leu Ala Ala His Val Glu Arg Gln Ala Ala
50                  55                  60
Ile Ala Pro His Ala Arg Glu His Leu Lys Arg Glu Ala Phe Ala Ala
65                  70                  75                  80
Ser His Gly Ala Ser Leu Asp Asp Phe Ala Glu Leu Arg Arg Phe Ala
                85                  90                  95
Asp Ala His Gly Leu Ala Leu Asp Arg Ala Asn Val Ala Ala Gly Thr
            100                 105                 110
Ala Val Leu Ser Gly Pro Val Asp Ala Ile Asn Arg Ala Phe Gly Val
            115                 120                 125
Glu Leu Arg His Phe Asp His Pro Asp Gly Ser Tyr Arg Ser Tyr Leu
            130                 135                 140
Gly Glu Val Thr Val Pro Ala Ser Ile Ala Pro Met Ile Glu Ala Val
145                 150                 155                 160
Leu Gly Leu Asp Thr Arg Pro Val Ala Arg Pro His Phe Arg Met Gln
                165                 170                 175
Arg Arg Ala Glu Gly Gly Phe Glu Ala Arg Ser Gln Ala Ala Ala Pro
            180                 185                 190
Thr Ala Tyr Thr Pro Leu Asp Val Ala Gln Ala Tyr Gln Phe Pro Glu
            195                 200                 205
Gly Leu Asp Gly Gln Gly Gln Cys Ile Ala Ile Ile Glu Leu Gly Gly
            210                 215                 220
Gly Tyr Asp Glu Ala Ser Leu Ala Gln Tyr Phe Ala Ser Leu Gly Val
225                 230                 235                 240
Pro Ala Pro Gln Val Val Ser Val Ser Val Asp Gly Ala Ser Asn Gln
                245                 250                 255
Pro Thr Gly Asp Pro Ser Gly Pro Asp Gly Glu Val Glu Leu Asp Ile
            260                 265                 270
Glu Val Ala Gly Ala Leu Ala Pro Gly Ala Lys Phe Ala Val Tyr Phe
            275                 280                 285
Ala Pro Asn Thr Asp Ala Gly Phe Leu Asp Ala Ile Thr Thr Ala Ile
            290                 295                 300
His Asp Pro Thr Leu Lys Pro Ser Val Val Ser Ile Ser Trp Ser Gly
305                 310                 315                 320
Pro Glu Asp Ser Trp Thr Ser Ala Ala Ile Ala Ala Met Asn Arg Ala
                325                 330                 335
Phe Leu Asp Ala Ala Ala Leu Gly Val Thr Val Leu Ala Ala Ala Gly
            340                 345                 350
Asp Ser Gly Ser Thr Asp Gly Glu Gln Asp Gly Leu Tyr His Val Ser
            355                 360                 365
Phe Pro Ala Ala Ser Pro Tyr Val Leu Ala Cys Gly Gly Thr Arg Leu
            370                 375                 380
Val Ala Ser Gly Gly Arg Ile Ala Gln Glu Thr Val Trp Asn Asp Gly
385                 390                 395                 400
Pro Asp Gly Gly Ala Thr Gly Gly Val Ser Arg Ile Phe Pro Leu
                405                 410                 415
Pro Ala Trp Gln Glu His Ala Asn Val Pro Pro Ser Ala Asn Pro Gly
            420                 425                 430
Ala Ser Ser Gly Arg Gly Val Pro Asp Leu Ala Gly Asn Ala Asp Pro
            435                 440                 445
```

```
Ala Thr Gly Tyr Glu Val Val Ile Asp Gly Glu Ala Thr Val Ile Gly
            450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His His
                565                 570

<210> SEQ ID NO 11
<211> LENGTH: 573
<212> TYPE: PRT
<213> ORGANISM: Artificial Sequence
<220> FEATURE:
<223> OTHER INFORMATION: Synthetic

<400> SEQUENCE: 11

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Leu Arg
            35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
            115                 120                 125

Glu Leu Arg His Phe Asp His Pro Asp Gly Ser Tyr Arg Ser Tyr Leu
            130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
            195                 200                 205

Gly Leu Asp Gly Gln Gly Gln Cys Ile Ala Ile Ile Glu Leu Gly Gly
            210                 215                 220

Gly Tyr Asp Glu Ala Ser Leu Ala Gln Tyr Phe Ala Ser Leu Gly Val
225                 230                 235                 240
```

```
Pro Ala Pro Gln Val Val Ser Val Ser Val Asp Gly Ala Ser Asn Gln
            245                 250                 255
Pro Thr Gly Asp Pro Ser Gly Pro Asp Gly Glu Val Glu Leu Asp Ile
            260                 265                 270
Glu Val Ala Gly Ala Leu Ala Pro Gly Ala Lys Phe Ala Val Tyr Phe
            275                 280                 285
Ala Pro Asn Thr Asp Ala Gly Phe Leu Asp Ala Ile Thr Thr Ala Ile
        290                 295                 300
His Asp Pro Thr Leu Lys Pro Ser Val Val Ser Ile Ser Trp Gly Gly
305                 310                 315                 320
Pro Glu Asp Ser Trp Thr Ser Ala Ala Ile Ala Ala Met Asn Arg Ala
            325                 330                 335
Phe Leu Asp Ala Ala Leu Gly Val Thr Val Leu Ala Ala Ala Ala Gly
            340                 345                 350
Asp Ser Gly Ser Thr Gly Gly Glu Gln Asp Gly Leu Tyr His Val His
            355                 360                 365
Phe Pro Ala Ala Ser Pro Tyr Val Leu Ala Cys Gly Gly Thr Arg Leu
        370                 375                 380
Val Ala Ser Gly Gly Arg Ile Ala Gln Glu Thr Val Trp Asn Asp Gly
385                 390                 395                 400
Pro Asp Gly Gly Ala Thr Gly Gly Val Ser Arg Ile Phe Pro Leu
            405                 410                 415
Pro Ala Trp Gln Glu His Ala Asn Val Pro Pro Ser Ala Asn Pro Gly
            420                 425                 430
Ala Ser Ser Gly Arg Gly Val Pro Asp Leu Ala Gly Asn Ala Asp Pro
        435                 440                 445
Ala Thr Gly Tyr Glu Val Val Ile Asp Gly Glu Ala Thr Val Ile Gly
            450                 455                 460
Gly Thr Ser Ala Val Ala Pro Leu Phe Ala Ala Leu Val Ala Arg Ile
465                 470                 475                 480
Asn Gln Lys Leu Gly Lys Ala Val Gly Tyr Leu Asn Pro Thr Leu Tyr
            485                 490                 495
Gln Leu Pro Ala Asp Val Phe His Asp Ile Thr Glu Gly Asn Asn Asp
            500                 505                 510
Ile Ala Asn Arg Ala Gln Ile Tyr Gln Ala Gly Pro Gly Trp Asp Pro
        515                 520                 525
Cys Thr Gly Leu Gly Ser Pro Ile Gly Val Arg Leu Leu Gln Ala Leu
            530                 535                 540
Leu Pro Ser Ala Ser Gln Pro Gln Pro Gly Ser Thr Glu Asn Leu Tyr
545                 550                 555                 560
Phe Gln Ser Gly Ala Leu Glu His His His His His His
            565                 570

<210> SEQ ID NO 12
<211> LENGTH: 573
<212> TYPE: PRT
<213> ORGANISM: Artificial Sequence
<220> FEATURE:
<223> OTHER INFORMATION: Synthetic

<400> SEQUENCE: 12

Met Ser Asp Met Glu Lys Pro Trp Lys Glu Gly Glu Ala Arg Ala
1               5                   10                  15
Val Leu Gln Gly His Ala Arg Ala Gln Ala Pro Gln Ala Val Asp Lys
            20                  25                  30
```

```
Gly Pro Val Ala Gly Asp Glu Arg Met Ala Val Thr Val Leu Arg
            35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
 65                 70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
                100                 105                 110

Ala Val Leu Ser Gly Pro Val Asp Ala Ile Asn Arg Ala Phe Gly Val
            115                 120                 125

Glu Leu Arg His Phe Asp His Pro Asp Gly Ser Tyr Arg Ser Tyr Leu
        130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Ser Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asp Thr Asp Ala Gly Phe Leu Asp Ala Ile Thr Thr Ala Ile
    290                 295                 300

His Asp Pro Thr Leu Lys Pro Ser Val Val Ser Ile Ser Trp Gly Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Ser Gly Ser Thr Asp Gly Glu Asp Asp Gly Leu Tyr His Val Asp
        355                 360                 365

Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro
        435                 440                 445
```

```
Ala Thr Gly Tyr Glu Val Val Ile Asp Gly Glu Ala Thr Val Ile Gly
        450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His
                565                 570
```

```
<210> SEQ ID NO 13
<211> LENGTH: 573
<212> TYPE: PRT
<213> ORGANISM: Artificial Sequence
<220> FEATURE:
<223> OTHER INFORMATION: Synthetic

<400> SEQUENCE: 13
```

```
Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Val Leu Arg
            35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
        115                 120                 125

Glu Leu Arg His Phe Asp His Pro Asp Gly Ser Tyr Arg Ser Tyr Leu
130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
210                 215                 220

Gly Tyr Asp Glu Ala Ser Leu Ala Gln Tyr Phe Ala Ser Leu Gly Val
225                 230                 235                 240
```

```
Pro Ala Pro Gln Val Val Ser Val Ser Val Asp Gly Ala Ser Asn Gln
                245                 250                 255

Pro Thr Gly Asp Pro Ser Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asp Thr Asp Ala Gly Phe Leu Asp Ala Ile Thr Thr Ala Ile
    290                 295                 300

His Asp Pro Thr Leu Lys Pro Ser Val Val Ser Ile Ser Trp Gly Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Ser Gly Ser Thr Asn Gly Glu Gln Asp Gly Leu Tyr His Val Asp
        355                 360                 365

Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro
        435                 440                 445

Ala Thr Gly Tyr Glu Val Val Ile Asp Gly Glu Ala Thr Val Ile Gly
    450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
    530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His
                565                 570

<210> SEQ ID NO 14
<211> LENGTH: 573
<212> TYPE: PRT
<213> ORGANISM: Artificial Sequence
<220> FEATURE:
<223> OTHER INFORMATION: Synthetic

<400> SEQUENCE: 14

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30
```

```
Gly Pro Val Ala Gly Asp Glu Arg Met Ala Val Thr Val Leu Arg
             35                  40                  45

Arg Gln Arg Ala Gly Glu Leu Ala Ala His Val Glu Arg Gln Ala Ala
 50                  55                  60

Ile Ala Pro His Ala Arg Glu His Leu Lys Arg Glu Ala Phe Ala Ala
 65                  70                  75                  80

Ser His Gly Ala Ser Leu Asp Asp Phe Ala Glu Leu Arg Arg Phe Ala
                 85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Phe Glu Ala Arg Ser Gln Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Ser Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asp Thr Ala Ala Gly Phe Leu Asp Ala Ile Thr Thr Ala Ile
    290                 295                 300

His Asp Pro Thr Leu Lys Pro Ser Val Val Ser Ile Ser Trp Gly Gly
305                 310                 315                 320

Pro Glu Asp Ser Trp Thr Ser Ala Ala Ile Ala Ala Met Asn Arg Ala
                325                 330                 335

Phe Leu Asp Ala Ala Leu Gly Val Thr Val Leu Ala Ala Ala Gly
            340                 345                 350

Asp Ser Gly Ser Thr Asp Gly Glu Gln Asp Gly Leu Tyr His Val Asp
        355                 360                 365

Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Ser Ala Asn Pro Gly
            420                 425                 430

Ala Ser Ser Gly Arg Gly Val Pro Asp Leu Ala Gly Asn Ala Asp Pro
        435                 440                 445

Ala Thr Gly Tyr Glu Val Val Ile Asp Gly Glu Ala Thr Val Ile Gly
```

-continued

```
            450                 455                 460
Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
                500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His His
                565                 570
```

<210> SEQ ID NO 15
<211> LENGTH: 573
<212> TYPE: PRT
<213> ORGANISM: Artificial Sequence
<220> FEATURE:
<223> OTHER INFORMATION: Synthetic

<400> SEQUENCE: 15

```
Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Leu Arg
            35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
```

```
                    245                 250                 255
Pro Thr Gly Asp Pro Ser Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asp Thr Ala Ala Gly Phe Leu Asp Ala Ile Thr Thr Ala Ile
    290                 295                 300

His Asp Pro Thr Leu Lys Pro Ser Val Val Ser Ile Ser Trp Gly Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Ser Gly Ser Thr Asn Gly Glu Gln Asp Gly Leu Tyr His Val Asp
        355                 360                 365

Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Ser Ala Asn Pro Gly
            420                 425                 430

Ala Ser Ser Gly Arg Gly Val Pro Asp Leu Ala Gly Asn Ala Asp Pro
        435                 440                 445

Ala Thr Gly Tyr Glu Val Val Ile Asp Gly Glu Ala Thr Val Ile Gly
    450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
    530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His
                565                 570

<210> SEQ ID NO 16
<211> LENGTH: 573
<212> TYPE: PRT
<213> ORGANISM: Artificial Sequence
<220> FEATURE:
<223> OTHER INFORMATION: Synthetic

<400> SEQUENCE: 16

Met Ser Asp Met Glu Lys Pro Trp Lys Glu Gly Glu Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Val Leu Arg
```

```
                35                  40                  45
Arg Gln Arg Ala Gly Glu Leu Ala Ala His Val Glu Arg Gln Ala Ala
            50                  55                  60
Ile Ala Pro His Ala Arg Glu His Leu Lys Arg Glu Ala Phe Ala Ala
65                  70                  75                  80
Ser His Gly Ala Ser Leu Asp Asp Phe Ala Glu Leu Arg Arg Phe Ala
                85                  90                  95
Asp Ala His Gly Leu Ala Leu Asp Arg Ala Asn Val Ala Ala Gly Thr
            100                 105                 110
Ala Val Leu Ser Gly Pro Val Asp Ala Ile Asn Arg Ala Phe Gly Val
        115                 120                 125
Glu Leu Arg His Phe Asp His Pro Asp Gly Ser Tyr Arg Ser Tyr Leu
    130                 135                 140
Gly Glu Val Thr Val Pro Ala Ser Ile Ala Pro Met Ile Glu Ala Val
145                 150                 155                 160
Leu Gly Leu Asp Thr Arg Pro Val Ala Arg Pro His Phe Arg Met Gln
                165                 170                 175
Arg Arg Ala Glu Gly Phe Glu Ala Arg Ser Gln Ala Ala Ala Pro
            180                 185                 190
Thr Ala Tyr Thr Pro Leu Asp Val Ala Gln Ala Tyr Gln Phe Pro Glu
        195                 200                 205
Gly Leu Asp Gly Gln Gly Gln Cys Ile Ala Ile Ile Glu Leu Gly Gly
    210                 215                 220
Gly Tyr Asp Glu Ala Ser Leu Ala Gln Tyr Phe Ala Ser Leu Gly Val
225                 230                 235                 240
Pro Ala Pro Gln Val Val Ser Val Ser Val Asp Gly Ala Ser Asn Gln
                245                 250                 255
Pro Thr Gly Asp Pro Ser Gly Pro Asp Gly Glu Val Glu Leu Asp Ile
            260                 265                 270
Glu Val Ala Gly Ala Leu Ala Pro Gly Ala Lys Phe Ala Val Tyr Phe
        275                 280                 285
Ala Pro Asn Thr Asp Ala Gly Phe Leu Asp Ala Ile Thr Thr Ala Ile
    290                 295                 300
His Asp Pro Thr Leu Lys Pro Ser Val Val Ser Ile Ser Trp Ser Gly
305                 310                 315                 320
Pro Glu Asp Ser Trp Thr Ser Ala Ala Ile Ala Ala Met Asn Arg Ala
                325                 330                 335
Phe Leu Asp Ala Ala Leu Gly Val Thr Val Leu Ala Ala Ala Gly
            340                 345                 350
Asp Ser Gly Ser Thr Gly Gly Glu Gln Asp Gly Leu Tyr His Val His
        355                 360                 365
Phe Pro Ala Ala Ser Pro Tyr Val Leu Ala Cys Gly Gly Thr Arg Leu
    370                 375                 380
Val Ala Ser Gly Gly Arg Ile Ala Gln Glu Thr Val Trp Asn Asp Gly
385                 390                 395                 400
Pro Asp Gly Gly Ala Thr Gly Gly Val Ser Arg Ile Phe Pro Leu
                405                 410                 415
Pro Ala Trp Gln Glu His Ala Asn Val Pro Pro Ser Ala Asn Pro Gly
            420                 425                 430
Ala Ser Ser Gly Arg Gly Val Pro Asp Leu Ala Gly Asn Ala Asp Pro
        435                 440                 445
Ala Thr Gly Tyr Glu Val Val Ile Asp Gly Glu Ala Thr Val Ile Gly
    450                 455                 460
```

```
Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His His
                565                 570
```

<210> SEQ ID NO 17
<211> LENGTH: 573
<212> TYPE: PRT
<213> ORGANISM: Artificial Sequence
<220> FEATURE:
<223> OTHER INFORMATION: Synthetic

<400> SEQUENCE: 17

```
Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Leu Arg
            35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255
```

-continued

```
Pro Thr Gly Asp Pro Ser Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asn Thr Asp Ala Gly Phe Leu Asp Ala Ile Thr Thr Ala Ile
    290                 295                 300

His Asp Pro Thr Leu Lys Pro Ser Val Val Ser Ile Ser Trp Gly Gly
305                 310                 315                 320

Pro Glu Asp Ser Trp Thr Ser Ala Ala Ile Ala Ala Met Asn Arg Ala
                325                 330                 335

Phe Leu Asp Ala Ala Leu Gly Val Thr Val Leu Ala Ala Ala Ala Gly
            340                 345                 350

Asp Asn Gly Ser Thr Gly Gly Glu Gln Asp Gly Leu Tyr His Val His
        355                 360                 365

Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro
        435                 440                 445

Ala Thr Gly Tyr Glu Val Val Ile Asp Gly Glu Ala Thr Val Ile Gly
    450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
    530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His
                565                 570
```

<210> SEQ ID NO 18
<211> LENGTH: 573
<212> TYPE: PRT
<213> ORGANISM: Artificial Sequence
<220> FEATURE:
<223> OTHER INFORMATION: Synthetic

<400> SEQUENCE: 18

```
Met Ser Asp Met Glu Lys Pro Trp Lys Glu Gly Glu Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
        35                  40                  45
```

Arg Gln Arg Ala Gly Glu Leu Ala Ala His Val Glu Arg Gln Ala Ala
 50                  55                  60

Ile Ala Pro His Ala Arg Glu His Leu Lys Arg Glu Ala Phe Ala Ala
 65                  70                  75                  80

Ser His Gly Ala Ser Leu Asp Asp Phe Ala Glu Leu Arg Arg Phe Ala
                 85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Ser Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asp Thr Asp Ala Gly Phe Leu Asp Ala Ile Thr Thr Ala Ile
    290                 295                 300

His Asp Pro Thr Leu Lys Pro Ser Val Val Ser Ile Ser Trp Gly Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Ser Gly Ser Thr Gly Gly Glu Asp Asp Gly Leu Tyr His Val Asp
        355                 360                 365

Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro
        435                 440                 445

Ala Thr Gly Tyr Glu Val Val Ile Asp Gly Glu Ala Thr Val Ile Gly
    450                 455                 460

```
Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
            485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
            530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His His
                565                 570

<210> SEQ ID NO 19
<211> LENGTH: 573
<212> TYPE: PRT
<213> ORGANISM: Artificial Sequence
<220> FEATURE:
<223> OTHER INFORMATION: Synthetic

<400> SEQUENCE: 19

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Leu Arg
            35                  40                  45

Arg Gln Arg Ala Gly Glu Leu Ala Ala His Val Glu Arg Gln Ala Ala
50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
            115                 120                 125

Glu Leu Arg His Phe Asp His Pro Asp Gly Ser Tyr Arg Ser Tyr Leu
130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
            195                 200                 205

Gly Leu Asp Gly Gln Gln Cys Ile Ala Ile Ile Glu Leu Gly Gly
            210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255
```

Pro Thr Gly Asp Pro Ser Gly Pro Asp Gly Glu Val Glu Leu Asp Ile
                260                 265                 270

Glu Val Ala Gly Ala Leu Ala Pro Gly Ala Lys Phe Ala Val Tyr Phe
            275                 280                 285

Ala Pro Asp Thr Asp Ala Gly Phe Leu Asp Ala Ile Thr Thr Ala Ile
        290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Leu Gly Val Thr Val Leu Ala Ala Ala Ala Gly
            340                 345                 350

Asp Ser Gly Ser Thr Gly Gly Glu Gln Asp Gly Leu Tyr His Val His
        355                 360                 365

Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro
        435                 440                 445

Ala Thr Gly Tyr Glu Val Val Ile Asp Gly Glu Ala Thr Val Ile Gly
    450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
    530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His His
                565                 570

<210> SEQ ID NO 20
<211> LENGTH: 573
<212> TYPE: PRT
<213> ORGANISM: Artificial Sequence
<220> FEATURE:
<223> OTHER INFORMATION: Synthetic

<400> SEQUENCE: 20

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Val Leu Arg
        35                  40                  45

```
Arg Gln Arg Ala Gly Glu Leu Ala Ala His Val Glu Arg Gln Ala Ala
 50                  55                  60
Ile Ala Pro His Ala Arg Glu His Leu Lys Arg Glu Ala Phe Ala Ala
 65                  70                  75                  80
Ser His Gly Ala Ser Leu Asp Asp Phe Ala Glu Leu Arg Arg Phe Ala
                 85                  90                  95
Asp Ala His Gly Leu Ala Leu Asp Arg Ala Asn Val Ala Ala Gly Thr
            100                 105                 110
Ala Val Leu Ser Gly Pro Val Asp Ala Ile Asn Arg Ala Phe Gly Val
            115                 120                 125
Glu Leu Arg His Phe Asp His Pro Asp Gly Ser Tyr Arg Ser Tyr Leu
130                 135                 140
Gly Glu Val Thr Val Pro Ala Ser Ile Ala Pro Met Ile Glu Ala Val
145                 150                 155                 160
Leu Gly Leu Asp Thr Arg Pro Val Ala Arg Pro His Phe Arg Met Gln
                165                 170                 175
Arg Arg Ala Glu Gly Gly Phe Glu Ala Arg Ser Gln Ala Ala Ala Pro
            180                 185                 190
Thr Ala Tyr Thr Pro Leu Asp Val Ala Gln Ala Tyr Gln Phe Pro Glu
            195                 200                 205
Gly Leu Asp Gly Gln Gly Gln Cys Ile Ala Ile Ile Glu Leu Gly Gly
210                 215                 220
Gly Tyr Asp Glu Ala Ser Leu Ala Gln Tyr Phe Ala Ser Leu Gly Val
225                 230                 235                 240
Pro Ala Pro Gln Val Val Ser Val Ser Val Asp Gly Ala Ser Asn Gln
                245                 250                 255
Pro Thr Gly Asp Pro Ser Gly Pro Asp Gly Glu Val Glu Leu Asp Ile
            260                 265                 270
Glu Val Ala Gly Ala Leu Ala Pro Gly Ala Lys Phe Ala Val Tyr Phe
            275                 280                 285
Ala Pro Asp Thr Ala Ala Gly Phe Leu Asp Ala Ile Thr Thr Ala Ile
290                 295                 300
His Asp Pro Thr Leu Lys Pro Ser Val Val Ser Ile Ser Trp Gly Gly
305                 310                 315                 320
Pro Glu Asp Ser Trp Thr Ser Ala Ala Ile Ala Ala Met Asn Arg Ala
                325                 330                 335
Phe Leu Asp Ala Ala Ala Leu Gly Val Thr Val Leu Ala Ala Ala Gly
            340                 345                 350
Asp Ser Gly Ser Thr Asn Gly Glu Asp Asp Gly Leu Tyr His Val Asp
            355                 360                 365
Phe Pro Ala Ala Ser Pro Tyr Val Leu Ala Cys Gly Gly Thr Arg Leu
370                 375                 380
Val Ala Ser Gly Gly Arg Ile Ala Gln Glu Thr Val Trp Asn Asp Gly
385                 390                 395                 400
Pro Asp Gly Gly Ala Thr Gly Gly Val Ser Arg Ile Phe Pro Leu
                405                 410                 415
Pro Ala Trp Gln Glu His Ala Asn Val Pro Pro Ser Ala Asn Pro Gly
            420                 425                 430
Ala Ser Ser Gly Arg Gly Val Pro Asp Leu Ala Gly Asn Ala Asp Pro
            435                 440                 445
Ala Thr Gly Tyr Glu Val Val Ile Asp Gly Glu Ala Thr Val Ile Gly
450                 455                 460
Gly Thr Ser Ala Val Ala Pro Leu Phe Ala Ala Leu Val Ala Arg Ile
```

```
                465                 470                 475                 480
            Asn Gln Lys Leu Gly Lys Ala Val Gly Tyr Leu Asn Pro Thr Leu Tyr
                            485                 490                 495
            Gln Leu Pro Ala Asp Val Phe His Asp Ile Thr Glu Gly Asn Asn Asp
                        500                 505                 510
            Ile Ala Asn Arg Ala Gln Ile Tyr Gln Ala Gly Pro Gly Trp Asp Pro
                        515                 520                 525
            Cys Thr Gly Leu Gly Ser Pro Ile Gly Val Arg Leu Leu Gln Ala Leu
                        530                 535                 540
            Leu Pro Ser Ala Ser Gln Pro Gln Pro Gly Ser Thr Glu Asn Leu Tyr
            545                 550                 555                 560
            Phe Gln Ser Gly Ala Leu Glu His His His His His His
                        565                 570

<210> SEQ ID NO 21
<211> LENGTH: 573
<212> TYPE: PRT
<213> ORGANISM: Artificial Sequence
<220> FEATURE:
<223> OTHER INFORMATION: Synthetic

<400> SEQUENCE: 21

Met Ser Asp Met Glu Lys Pro Trp Lys Glu Gly Glu Ala Arg Ala
1               5                   10                  15
Val Leu Gln Gly His Ala Arg Ala Gln Ala Pro Gln Ala Val Asp Lys
                20                  25                  30
Gly Pro Val Ala Gly Asp Glu Arg Met Ala Val Thr Val Leu Arg
            35                  40                  45
Arg Gln Arg Ala Gly Glu Leu Ala Ala His Val Glu Arg Gln Ala Ala
        50                  55                  60
Ile Ala Pro His Ala Arg Glu His Leu Lys Arg Glu Ala Phe Ala Ala
65                  70                  75                  80
Ser His Gly Ala Ser Leu Asp Asp Phe Ala Glu Leu Arg Arg Phe Ala
                85                  90                  95
Asp Ala His Gly Leu Ala Leu Asp Arg Ala Asn Val Ala Ala Gly Thr
            100                 105                 110
Ala Val Leu Ser Gly Pro Val Asp Ala Ile Asn Arg Ala Phe Gly Val
        115                 120                 125
Glu Leu Arg His Phe Asp His Pro Asp Gly Ser Tyr Arg Ser Tyr Leu
    130                 135                 140
Gly Glu Val Thr Val Pro Ala Ser Ile Ala Pro Met Ile Glu Ala Val
145                 150                 155                 160
Leu Gly Leu Asp Thr Arg Pro Val Ala Arg Pro His Phe Arg Met Gln
                165                 170                 175
Arg Arg Ala Glu Gly Gly Phe Glu Ala Arg Ser Gln Ala Ala Ala Pro
            180                 185                 190
Thr Ala Tyr Thr Pro Leu Asp Val Ala Gln Ala Tyr Gln Phe Pro Glu
        195                 200                 205
Gly Leu Asp Gly Gln Gly Gln Cys Ile Ala Ile Ile Glu Leu Gly Gly
    210                 215                 220
Gly Tyr Asp Glu Ala Ser Leu Ala Gln Tyr Phe Ala Ser Leu Gly Val
225                 230                 235                 240
Pro Ala Pro Gln Val Val Ser Val Ser Val Asp Gly Ala Ser Asn Gln
                245                 250                 255
Pro Thr Gly Asp Pro Ser Gly Pro Asp Gly Glu Val Glu Leu Asp Ile
```

```
                260                 265                 270
Glu Val Ala Gly Ala Leu Ala Pro Gly Ala Lys Phe Ala Val Tyr Phe
            275                 280                 285

Ala Pro Asn Thr Asp Ala Gly Phe Leu Asp Ile Thr Thr Ala Ile
        290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Asn Gly Ser Thr Gly Gly Glu Gln Asp Gly Leu Tyr His Val His
        355                 360                 365

Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro
        435                 440                 445

Ala Thr Gly Tyr Glu Val Val Ile Asp Gly Glu Ala Thr Val Ile Gly
    450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
    530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His His
                565                 570

<210> SEQ ID NO 22
<211> LENGTH: 573
<212> TYPE: PRT
<213> ORGANISM: Artificial Sequence
<220> FEATURE:
<223> OTHER INFORMATION: Synthetic

<400> SEQUENCE: 22

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Val Leu Arg
        35                  40                  45

Arg Gln Arg Ala Gly Glu Leu Ala Ala His Val Glu Arg Gln Ala Ala
```

-continued

```
                 50                  55                  60
Ile Ala Pro His Ala Arg Glu His Leu Lys Arg Glu Ala Phe Ala Ala
 65                  70                  75                  80
Ser His Gly Ala Ser Leu Asp Asp Phe Ala Glu Leu Arg Arg Phe Ala
                     85                  90                  95
Asp Ala His Gly Leu Ala Leu Asp Arg Ala Asn Val Ala Ala Gly Thr
                100                 105                 110
Ala Val Leu Ser Gly Pro Val Asp Ala Ile Asn Arg Ala Phe Gly Val
            115                 120                 125
Glu Leu Arg His Phe Asp His Pro Asp Gly Ser Tyr Arg Ser Tyr Leu
130                 135                 140
Gly Glu Val Thr Val Pro Ala Ser Ile Ala Pro Met Ile Glu Ala Val
145                 150                 155                 160
Leu Gly Leu Asp Thr Arg Pro Val Ala Arg Pro His Phe Arg Met Gln
                165                 170                 175
Arg Arg Ala Glu Gly Gly Phe Glu Ala Arg Ser Gln Ala Ala Ala Pro
                180                 185                 190
Thr Ala Tyr Thr Pro Leu Asp Val Ala Gln Ala Tyr Gln Phe Pro Glu
                195                 200                 205
Gly Leu Asp Gly Gln Gly Gln Cys Ile Ala Ile Ile Glu Leu Gly Gly
            210                 215                 220
Gly Tyr Asp Glu Ala Ser Leu Ala Gln Tyr Phe Ala Ser Leu Gly Val
225                 230                 235                 240
Pro Ala Pro Gln Val Val Ser Val Ser Val Asp Gly Ala Ser Asn Gln
                245                 250                 255
Pro Thr Gly Asp Pro Ser Gly Pro Asp Gly Glu Val Glu Leu Asp Ile
                260                 265                 270
Glu Val Ala Gly Ala Leu Ala Pro Gly Ala Lys Phe Ala Val Tyr Phe
            275                 280                 285
Ala Pro Asp Thr Ala Ala Gly Phe Leu Asp Ala Ile Thr Thr Ala Ile
                290                 295                 300
His Asp Pro Thr Leu Lys Pro Ser Val Val Ser Ile Ser Trp Gly Gly
305                 310                 315                 320
Pro Glu Asp Ser Trp Thr Ser Ala Ala Ile Ala Ala Met Asn Arg Ala
                325                 330                 335
Phe Leu Asp Ala Ala Ala Leu Gly Val Thr Val Leu Ala Ala Ala Gly
                340                 345                 350
Asp Ser Gly Ser Thr Gly Gly Glu Asp Asp Gly Leu Tyr His Val Asp
            355                 360                 365
Phe Pro Ala Ala Ser Pro Tyr Val Leu Ala Cys Gly Gly Thr Arg Leu
370                 375                 380
Val Ala Ser Gly Gly Arg Ile Ala Gln Glu Thr Val Trp Asn Asp Gly
385                 390                 395                 400
Pro Asp Gly Gly Ala Thr Gly Gly Val Ser Arg Ile Phe Pro Leu
                405                 410                 415
Pro Ala Trp Gln Glu His Ala Asn Val Pro Pro Ser Ala Asn Pro Gly
                420                 425                 430
Ala Ser Ser Gly Arg Gly Val Pro Asp Leu Ala Gly Asn Ala Asp Pro
            435                 440                 445
Ala Thr Gly Tyr Glu Val Val Ile Asp Gly Glu Ala Thr Val Ile Gly
            450                 455                 460
Gly Thr Ser Ala Val Ala Pro Leu Phe Ala Ala Leu Val Ala Arg Ile
465                 470                 475                 480
```

```
Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
            530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His His
                565                 570

<210> SEQ ID NO 23
<211> LENGTH: 573
<212> TYPE: PRT
<213> ORGANISM: Artificial Sequence
<220> FEATURE:
<223> OTHER INFORMATION: Synthetic

<400> SEQUENCE: 23

Met Ser Asp Met Glu Lys Pro Trp Lys Glu Gly Glu Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Ser Gly Pro Asp Gly Glu Val Glu Leu Asp Ile
            260                 265                 270
```

Glu Val Ala Gly Ala Leu Ala Pro Gly Ala Lys Phe Ala Val Tyr Phe
            275                 280                 285

Ala Pro Asp Thr Asp Ala Gly Phe Leu Asp Ala Ile Thr Thr Ala Ile
            290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Ser Gly Ser Thr Gly Gly Glu Asp Gly Leu Tyr His Val His
            355                 360                 365

Phe Pro Ala Ala Ser Pro Tyr Val Leu Ala Cys Gly Gly Thr Arg Leu
            370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
                420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
            450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His
                565                 570

<210> SEQ ID NO 24
<211> LENGTH: 573
<212> TYPE: PRT
<213> ORGANISM: Artificial Sequence
<220> FEATURE:
<223> OTHER INFORMATION: Synthetic

<400> SEQUENCE: 24

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
                35                  40                  45

Arg Gln Arg Ala Gly Glu Leu Ala Ala His Val Glu Arg Gln Ala Ala
        50                  55                  60

```
Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
            115                 120                 125

Glu Leu Arg His Phe Asp His Pro Asp Gly Ser Tyr Arg Ser Tyr Leu
            130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
            195                 200                 205

Gly Leu Asp Gly Gln Gly Gln Cys Ile Ala Ile Ile Glu Leu Gly Gly
210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Ser Gly Pro Asp Gly Glu Val Glu Leu Asp Ile
            260                 265                 270

Glu Val Ala Gly Ala Leu Ala Pro Gly Ala Lys Phe Ala Val Tyr Phe
            275                 280                 285

Ala Pro Asp Thr Asp Ala Gly Phe Leu Asp Ala Ile Thr Thr Ala Ile
            290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Leu Gly Val Thr Val Leu Ala Ala Ala Gly
            340                 345                 350

Asp Asn Gly Ser Thr Gly Gly Glu Gln Asp Gly Leu Tyr His Val His
            355                 360                 365

Phe Pro Ala Ala Ser Pro Tyr Val Leu Ala Cys Gly Gly Thr Arg Leu
            370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Ser Ala Asn Pro Gly
            420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
            450                 455                 460

Gly Thr Ser Ala Val Ala Pro Leu Phe Ala Ala Leu Val Ala Arg Ile
465                 470                 475                 480
```

```
Asn Gln Lys Leu Gly Lys Ala Val Gly Tyr Leu Asn Pro Thr Leu Tyr
                485                 490                 495
Gln Leu Pro Ala Asp Val Phe His Asp Ile Thr Glu Gly Asn Asn Asp
            500                 505                 510
Ile Ala Asn Arg Ala Gln Ile Tyr Gln Ala Gly Pro Gly Trp Asp Pro
515                 520                 525
Cys Thr Gly Leu Gly Ser Pro Ile Gly Val Arg Leu Leu Gln Ala Leu
        530                 535                 540
Leu Pro Ser Ala Ser Gln Pro Gln Pro Gly Ser Thr Glu Asn Leu Tyr
545                 550                 555                 560
Phe Gln Ser Gly Ala Leu Glu His His His His His His
                565                 570

<210> SEQ ID NO 25
<211> LENGTH: 573
<212> TYPE: PRT
<213> ORGANISM: Artificial Sequence
<220> FEATURE:
<223> OTHER INFORMATION: Synthetic

<400> SEQUENCE: 25

Met Ser Asp Met Glu Lys Pro Trp Lys Glu Gly Glu Glu Ala Arg Ala
1               5                   10                  15
Val Leu Gln Gly His Ala Arg Ala Gln Ala Pro Gln Ala Val Asp Lys
            20                  25                  30
Gly Pro Val Ala Gly Asp Glu Arg Met Ala Val Thr Val Leu Arg
        35                  40                  45
Arg Gln Arg Ala Gly Glu Leu Ala Ala His Val Glu Arg Gln Ala Ala
    50                  55                  60
Ile Ala Pro His Ala Arg Glu His Leu Lys Arg Glu Ala Phe Ala Ala
65                  70                  75                  80
Ser His Gly Ala Ser Leu Asp Asp Phe Ala Glu Leu Arg Arg Phe Ala
                85                  90                  95
Asp Ala His Gly Leu Ala Leu Asp Arg Ala Asn Val Ala Ala Gly Thr
            100                 105                 110
Ala Val Leu Ser Gly Pro Val Asp Ala Ile Asn Arg Ala Phe Gly Val
        115                 120                 125
Glu Leu Arg His Phe Asp His Pro Asp Gly Ser Tyr Arg Ser Tyr Leu
    130                 135                 140
Gly Glu Val Thr Val Pro Ala Ser Ile Ala Pro Met Ile Glu Ala Val
145                 150                 155                 160
Leu Gly Leu Asp Thr Arg Pro Val Ala Arg Pro His Phe Arg Met Gln
                165                 170                 175
Arg Arg Ala Glu Gly Gly Phe Glu Ala Arg Ser Gln Ala Ala Ala Pro
            180                 185                 190
Thr Ala Tyr Thr Pro Leu Asp Val Ala Gln Ala Tyr Gln Phe Pro Glu
        195                 200                 205
Gly Leu Asp Gly Gln Gly Gln Cys Ile Ala Ile Ile Glu Leu Gly Gly
    210                 215                 220
Gly Tyr Asp Glu Ala Ser Leu Ala Gln Tyr Phe Ala Ser Leu Gly Val
225                 230                 235                 240
Pro Ala Pro Gln Val Val Ser Val Ser Val Asp Gly Ala Ser Asn Gln
                245                 250                 255
Pro Thr Gly Asp Pro Ser Gly Pro Asp Gly Glu Val Gly Leu Asp Ile
            260                 265                 270
```

Glu Val Ala Gly Ala Leu Ala Pro Gly Ala Lys Phe Ala Val Tyr Phe
            275                 280                 285

Ala Pro Asp Thr Ala Ala Gly Phe Leu Asp Ala Ile Thr Thr Ala Ile
290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Leu Gly Val Thr Val Leu Ala Ala Ala Gly
            340                 345                 350

Asp Ser Gly Ser Thr Gly Gly Glu Asp Gly Leu Tyr His Val His
        355                 360                 365

Phe Pro Ala Ala Ser Pro Tyr Val Leu Ala Cys Gly Gly Thr Arg Leu
370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
            405                 410                 415

Pro Ala Trp Gln Glu His Ala Asn Val Pro Pro Ser Ala Asn Pro Gly
                420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
        450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
            485                 490                 495

Gln Leu Pro Ala Asp Val Phe His Asp Ile Thr Glu Gly Asn Asn Asp
                500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His
            565                 570

<210> SEQ ID NO 26
<211> LENGTH: 573
<212> TYPE: PRT
<213> ORGANISM: Artificial Sequence
<220> FEATURE:
<223> OTHER INFORMATION: Synthetic

<400> SEQUENCE: 26

Met Ser Asp Met Glu Lys Pro Trp Lys Glu Gly Glu Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Val Leu Arg
        35                  40                  45

Arg Gln Arg Ala Gly Glu Leu Ala Ala His Val Glu Arg Gln Ala Ala
    50                  55                  60

```
Ile Ala Pro His Ala Arg Glu His Leu Lys Arg Glu Ala Phe Ala Ala
 65                  70                  75                  80

Ser His Gly Ala Ser Leu Asp Asp Phe Ala Glu Leu Arg Arg Phe Ala
             85                  90                  95

Asp Ala His Gly Leu Ala Leu Asp Arg Ala Asn Val Ala Ala Gly Thr
        100                 105                 110

Ala Val Leu Ser Gly Pro Val Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
            165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
            245                 250                 255

Pro Thr Gly Asp Pro Ser Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asp Thr Asp Ala Gly Phe Leu Asp Ala Ile Thr Thr Ala Ile
        290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
            325                 330                 335

Phe Leu Asp Ala Ala Leu Gly Val Thr Val Leu Ala Ala Ala Gly
            340                 345                 350

Asp Asn Gly Ser Thr Gly Gly Glu Asp Gly Leu Tyr His Val His
            355                 360                 365

Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
            405                 410                 415

Pro Ala Trp Gln Glu His Ala Asn Val Pro Ser Ala Asn Pro Gly
            420                 425                 430

Ala Ser Ser Gly Arg Gly Val Pro Asp Leu Ala Gly Asn Ala Asp Pro
    435                 440                 445

Ala Thr Gly Tyr Glu Val Val Ile Asp Gly Glu Thr Val Ile Gly
        450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
```

```
                        485                 490                 495
Gln Leu Pro Ala Asp Val Phe His Asp Ile Thr Glu Gly Asn Asn Asp
                500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
        530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His His
                565                 570

<210> SEQ ID NO 27
<211> LENGTH: 573
<212> TYPE: PRT
<213> ORGANISM: Artificial Sequence
<220> FEATURE:
<223> OTHER INFORMATION: Synthetic

<400> SEQUENCE: 27

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Ser Gly Pro Asp Gly Glu Val Glu Leu Asp Ile
            260                 265                 270

Glu Val Ala Gly Ala Leu Ala Pro Gly Ala Lys Phe Ala Val Tyr Phe
```

```
                    275                 280                 285
Ala Pro Asp Thr Ala Ala Gly Phe Leu Asp Ala Ile Thr Thr Ala Ile
            290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Leu Gly Val Thr Val Leu Ala Ala Ala Gly
            340                 345                 350

Asp Asn Gly Ser Thr Gly Gly Glu Asp Gly Leu Tyr His Val His
                355                 360                 365

Phe Pro Ala Ala Ser Pro Tyr Val Leu Ala Cys Gly Gly Thr Arg Leu
            370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Gly Val Ser Arg Ile Phe Pro Leu
                405                 410                 415

Pro Ala Trp Gln Glu His Ala Asn Val Pro Ser Ala Asn Pro Gly
            420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
            450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His
                565                 570
```

<210> SEQ ID NO 28
<211> LENGTH: 573
<212> TYPE: PRT
<213> ORGANISM: Artificial Sequence
<220> FEATURE:
<223> OTHER INFORMATION: Synthetic

<400> SEQUENCE: 28

```
Met Ser Asp Met Glu Lys Pro Trp Lys Glu Gly Glu Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Leu Arg
            35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
```

```
              65                  70                  75                  80
    Ser His Gly Ala Ser Leu Asp Asp Phe Ala Glu Leu Arg Arg Phe Ala
                         85                  90                  95

Asp Ala His Gly Leu Ala Leu Asp Arg Ala Asn Val Ala Ala Gly Thr
                    100                 105                 110

Ala Val Leu Ser Gly Pro Val Asp Ala Ile Asn Arg Ala Phe Gly Val
                    115                 120                 125

Glu Leu Arg His Phe Asp His Pro Asp Gly Ser Tyr Arg Ser Tyr Leu
            130                 135                 140

Gly Glu Val Thr Val Pro Ala Ser Ile Ala Pro Met Ile Glu Ala Val
    145                 150                 155                 160

Leu Gly Leu Asp Thr Arg Pro Val Ala Arg Pro His Phe Arg Met Gln
                    165                 170                 175

Arg Arg Ala Glu Gly Gly Phe Glu Ala Arg Ser Gln Ala Ala Ala Pro
                    180                 185                 190

Thr Ala Tyr Thr Pro Leu Asp Val Ala Gln Ala Tyr Gln Phe Pro Glu
            195                 200                 205

Gly Leu Asp Gly Gln Gly Gln Cys Ile Ala Ile Ile Glu Leu Gly Gly
            210                 215                 220

Gly Tyr Asp Glu Ala Ser Leu Ala Gln Tyr Phe Ala Ser Leu Gly Val
    225                 230                 235                 240

Pro Ala Pro Gln Val Val Ser Val Ser Val Asp Gly Ala Ser Asn Gln
                    245                 250                 255

Pro Thr Gly Asp Pro Ser Gly Pro Asp Gly Glu Val Glu Leu Asp Ile
                    260                 265                 270

Glu Val Ala Gly Ala Leu Ala Pro Gly Ala Lys Phe Ala Val Tyr Phe
            275                 280                 285

Ala Pro Asp Ser Asp Ala Gly Phe Leu Asp Ala Ile Thr Thr Ala Ile
            290                 295                 300

His Asp Pro Thr Leu Lys Pro Ser Val Val Ser Ile Ser Trp Ser Gly
    305                 310                 315                 320

Pro Glu Asp Ser Trp Thr Ser Ala Ala Ile Ala Ala Met Asn Arg Ala
                    325                 330                 335

Phe Leu Asp Ala Ala Ala Leu Gly Val Thr Val Leu Ala Ala Ala Gly
                    340                 345                 350

Asp Ser Gly Ser Thr Gly Gly Glu Gln Asp Gly Leu Tyr His Val His
            355                 360                 365

Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Asp Gly
    385                 390                 395                 400

Pro Asp Gly Gly Ala Thr Gly Gly Val Ser Arg Ile Phe Pro Leu
                    405                 410                 415

Pro Ala Trp Gln Glu His Ala Asn Val Pro Ser Ala Asn Pro Gly
                    420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
            450                 455                 460

Gly Thr Ser Ala Val Ala Pro Leu Phe Ala Ala Leu Val Ala Arg Ile
    465                 470                 475                 480

Asn Gln Lys Leu Gly Lys Ala Val Gly Tyr Leu Asn Pro Thr Leu Tyr
                    485                 490                 495
```

-continued

Gln Leu Pro Ala Asp Val Phe His Asp Ile Thr Glu Gly Asn Asn Asp
               500                 505                 510

Ile Ala Asn Arg Ala Gln Ile Tyr Gln Ala Gly Pro Gly Trp Asp Pro
               515                 520                 525

Cys Thr Gly Leu Gly Ser Pro Ile Gly Val Arg Leu Leu Gln Ala Leu
               530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His
               565                 570

<210> SEQ ID NO 29
<211> LENGTH: 573
<212> TYPE: PRT
<213> ORGANISM: Artificial Sequence
<220> FEATURE:
<223> OTHER INFORMATION: Synthetic

<400> SEQUENCE: 29

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Leu Arg
                35                  40                  45

Arg Gln Arg Ala Gly Glu Leu Ala Ala His Val Glu Arg Gln Ala Ala
            50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
                100                 105                 110

Ala Val Leu Ser Gly Pro Val Asp Ala Ile Asn Arg Ala Phe Gly Val
            115                 120                 125

Glu Leu Arg His Phe Asp His Pro Asp Gly Ser Tyr Arg Ser Tyr Leu
130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
                195                 200                 205

Gly Leu Asp Gly Gln Gly Gln Cys Ile Ala Ile Ile Glu Leu Gly Gly
            210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Asp Gly Ala Ser Asn Gln
                245                 250                 255

Pro Thr Gly Asp Pro Ser Gly Pro Asp Gly Glu Val Glu Leu Asp Ile
                260                 265                 270

Glu Val Ala Gly Ala Leu Ala Pro Gly Ala Lys Phe Ala Val Tyr Phe
            275                 280                 285

Ala Pro Asp Thr Thr Ala Gly Phe Leu Asp Ala Ile Thr Thr Ala Ile
        290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
            325                 330                 335

Phe Leu Asp Ala Ala Leu Gly Val Thr Val Leu Ala Ala Ala Gly
        340                 345                 350

Asp Ser Gly Ser Thr Gly Gly Glu Gln Asp Gly Leu Tyr His Val His
    355                 360                 365

Phe Pro Ala Ala Ser Pro Tyr Val Leu Ala Cys Gly Gly Thr Arg Leu
370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
            405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro
    435                 440                 445

Ala Thr Gly Tyr Glu Val Val Ile Asp Gly Glu Ala Thr Val Ile Gly
    450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His His
                565                 570

<210> SEQ ID NO 30
<211> LENGTH: 573
<212> TYPE: PRT
<213> ORGANISM: Artificial Sequence
<220> FEATURE:
<223> OTHER INFORMATION: Synthetic

<400> SEQUENCE: 30

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

-continued

```
Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Gly Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asp Ser Asp Ala Gly Phe Leu Asp Ala Ile Thr Thr Ala Ile
    290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Ser Gly Ser Thr Gly Gly Glu Gln Asp Gly Leu Tyr His Val His
        355                 360                 365

Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro
        435                 440                 445

Ala Thr Gly Tyr Glu Val Val Ile Asp Gly Glu Ala Thr Val Ile Gly
    450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495
```

```
Gln Leu Pro Ala Asp Val Phe His Asp Ile Thr Glu Gly Asn Asn Asp
                500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
        530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His His
                565                 570
```

<210> SEQ ID NO 31
<211> LENGTH: 573
<212> TYPE: PRT
<213> ORGANISM: Artificial Sequence
<220> FEATURE:
<223> OTHER INFORMATION: Synthetic

<400> SEQUENCE: 31

```
Met Ser Asp Met Glu Lys Pro Trp Lys Glu Gly Glu Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Lys Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285
```

Ala Pro Asp Thr Asn Ala Gly Phe Leu Asp Ala Ile Thr Thr Ala Ile
290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
                340                 345                 350

Asp Ser Gly Ser Thr Gly Gly Glu Gln Asp Gly Leu Tyr His Val His
                355                 360                 365

Phe Pro Ala Ala Ser Pro Tyr Val Leu Ala Cys Gly Gly Thr Arg Leu
370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
                420                 425                 430

Ala Ser Ser Gly Arg Gly Val Pro Asp Leu Ala Gly Asn Ala Asp Pro
                435                 440                 445

Ala Thr Gly Tyr Glu Val Val Ile Asp Gly Glu Ala Thr Val Ile Gly
                450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
                500                 505                 510

Ile Ala Asn Arg Ala Gln Ile Tyr Gln Ala Gly Pro Gly Trp Asp Pro
                515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His His
                565                 570

<210> SEQ ID NO 32
<211> LENGTH: 573
<212> TYPE: PRT
<213> ORGANISM: Artificial Sequence
<220> FEATURE:
<223> OTHER INFORMATION: Synthetic

<400> SEQUENCE: 32

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Leu Arg
                35                  40                  45

Arg Gln Arg Ala Gly Glu Leu Ala Ala His Val Glu Arg Gln Ala Ala
            50                  55                  60

Ile Ala Pro His Ala Arg Glu His Leu Lys Arg Glu Ala Phe Ala Ala
65                  70                  75                  80

```
Ser His Gly Ala Ser Leu Asp Asp Phe Ala Glu Leu Arg Arg Phe Ala
                85                  90                  95
Asp Ala His Gly Leu Ala Leu Asp Arg Ala Asn Val Ala Ala Gly Thr
            100                 105                 110
Ala Val Leu Ser Gly Pro Asp Ala Ile Asn Arg Ala Phe Gly Val
        115                 120                 125
Glu Leu Arg His Phe Asp His Pro Asp Gly Ser Tyr Arg Ser Tyr Leu
    130                 135                 140
Gly Glu Val Thr Val Pro Ala Ser Ile Ala Pro Met Ile Glu Ala Val
145                 150                 155                 160
Leu Gly Leu Asp Thr Arg Pro Val Ala Arg Pro His Phe Arg Met Gln
                165                 170                 175
Arg Arg Ala Glu Gly Phe Glu Ala Arg Ser Gln Ala Ala Pro
            180                 185                 190
Thr Ala Tyr Thr Pro Leu Asp Val Ala Gln Ala Tyr Gln Phe Pro Glu
        195                 200                 205
Gly Leu Asp Gly Gln Gly Gln Cys Ile Ala Ile Ile Glu Leu Gly Gly
    210                 215                 220
Gly Tyr Asp Glu Ala Ser Leu Ala Gln Tyr Phe Ala Ser Leu Gly Val
225                 230                 235                 240
Pro Ala Pro Gln Val Val Ser Val Ser Val Asp Gly Ala Ser Asn Gln
                245                 250                 255
Pro Thr Gly Asp Pro Lys Gly Pro Asp Gly Glu Val Glu Leu Asp Ile
            260                 265                 270
Glu Val Ala Gly Ala Leu Ala Pro Gly Ala Lys Phe Ala Val Tyr Phe
        275                 280                 285
Ala Pro Asp Thr Thr Ala Gly Phe Leu Asp Ala Ile Thr Thr Ala Ile
    290                 295                 300
His Asp Pro Thr Leu Lys Pro Ser Val Val Ser Ile Ser Trp Ser Gly
305                 310                 315                 320
Pro Glu Asp Ser Trp Thr Ser Ala Ala Ile Ala Ala Met Asn Arg Ala
                325                 330                 335
Phe Leu Asp Ala Ala Leu Gly Val Thr Val Leu Ala Ala Ala Gly
            340                 345                 350
Asp Ser Gly Ser Thr Gly Gly Glu Gln Asp Gly Leu Tyr His Val His
        355                 360                 365
Phe Pro Ala Ala Ser Pro Tyr Val Leu Ala Cys Gly Gly Thr Arg Leu
    370                 375                 380
Val Ala Ser Gly Gly Arg Ile Ala Gln Glu Thr Val Trp Asn Asp Gly
385                 390                 395                 400
Pro Asp Gly Gly Ala Thr Gly Gly Val Ser Arg Ile Phe Pro Leu
                405                 410                 415
Pro Ala Trp Gln Glu His Ala Asn Val Pro Ser Ala Asn Pro Gly
            420                 425                 430
Ala Ser Ser Gly Arg Gly Val Pro Asp Leu Ala Gly Asn Ala Asp Pro
        435                 440                 445
Ala Thr Gly Tyr Glu Val Val Ile Asp Gly Glu Ala Thr Val Ile Gly
    450                 455                 460
Gly Thr Ser Ala Val Ala Pro Leu Phe Ala Ala Leu Val Ala Arg Ile
465                 470                 475                 480
Asn Gln Lys Leu Gly Lys Ala Val Gly Tyr Leu Asn Pro Thr Leu Tyr
                485                 490                 495
Gln Leu Pro Ala Asp Val Phe His Asp Ile Thr Glu Gly Asn Asn Asp
```

```
              500                 505                 510
Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His His
                565                 570

<210> SEQ ID NO 33
<211> LENGTH: 573
<212> TYPE: PRT
<213> ORGANISM: Homo sapiens

<400> SEQUENCE: 33

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
        115                 120                 125

Glu Leu Arg His Phe Asp His Pro Asp Gly Ser Tyr Arg Ser Tyr Leu
130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Ser Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asn Thr Asp Ala Gly Phe Leu Asp Ala Ile Thr Thr Ala Ile
290                 295                 300
```

```
His Asp Pro Thr Leu Lys Pro Ser Val Val Ser Ile Ser Trp Gly Gly
305                 310                 315                 320

Pro Glu Asp Ser Trp Thr Ser Ala Ala Ile Ala Met Asn Arg Ala
            325                 330                 335

Phe Leu Asp Ala Ala Ala Leu Gly Val Thr Val Leu Ala Ala Ala Gly
            340                 345                 350

Asp Ser Gly Ser Thr Asp Gly Glu Gln Asp Gly Leu Tyr His Val Asp
            355                 360                 365

Phe Pro Ala Ala Ser Pro Tyr Val Leu Ala Cys Gly Gly Thr Arg Leu
        370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
            405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
            450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His
                565                 570

<210> SEQ ID NO 34
<211> LENGTH: 6
<212> TYPE: PRT
<213> ORGANISM: Artificial Sequence
<220> FEATURE:
<223> OTHER INFORMATION: Synthetic

<400> SEQUENCE: 34

Pro Gln Pro Gln Leu Pro
1               5

<210> SEQ ID NO 35
<211> LENGTH: 384
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (73)..(73)
<223> OTHER INFORMATION: X can be S, K or G
<220> FEATURE:
<221> NAME/KEY: MISC_FEATURE
<222> LOCATION: (102)..(102)
<223> OTHER INFORMATION: X can be N or D
```

```
<220> FEATURE:
<221> NAME/KEY: MISC_FEATURE
<222> LOCATION: (103)..(103)
<223> OTHER INFORMATION: X can be T or S
<220> FEATURE:
<221> NAME/KEY: MISC_FEATURE
<222> LOCATION: (104)..(104)
<223> OTHER INFORMATION: X can be T or S
<220> FEATURE:
<221> NAME/KEY: MISC_FEATURE
<222> LOCATION: (130)..(130)
<223> OTHER INFORMATION: X can be G or S
<220> FEATURE:
<221> NAME/KEY: MISC_FEATURE
<222> LOCATION: (165)..(165)
<223> OTHER INFORMATION: X can be S or N
<220> FEATURE:
<221> NAME/KEY: MISC_FEATURE
<222> LOCATION: (168)..(168)
<223> OTHER INFORMATION: X can be T or A
<220> FEATURE:
<221> NAME/KEY: MISC_FEATURE
<222> LOCATION: (169)..(169)
<223> OTHER INFORMATION: X can be D, N or G
<220> FEATURE:
<221> NAME/KEY: MISC_FEATURE
<222> LOCATION: (172)..(172)
<223> OTHER INFORMATION: X can be Q or D
<220> FEATURE:
<221> NAME/KEY: MISC_FEATURE
<222> LOCATION: (179)..(179)
<223> OTHER INFORMATION: X can be D, S, or H

<400> SEQUENCE: 35

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Xaa Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Xaa Xaa Xaa Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Xaa Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Xaa Gly Ser Xaa Xaa Gly Glu Xaa Asp Gly Leu Tyr
                165                 170                 175

His Val Xaa Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Gly Val Ser Arg Ile
    210                 215                 220

Phe Pro Leu Pro Ala Trp Gln Glu His Ala Asn Val Pro Pro Ser Ala
225                 230                 235                 240
```

```
Asn Pro Gly Ala Ser Ser Gly Arg Gly Val Pro Asp Leu Ala Gly Asn
            245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
            275                 280                 285

Ala Arg Ile Asn Gln Lys Leu Gly Lys Ala Val Gly Tyr Leu Asn Pro
            290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
            325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
            355                 360                 365

Asn Leu Tyr Phe Gln Ser Gly Ala Leu Glu His His His His His His
            370                 375                 380
```

<210> SEQ ID NO 36
<211> LENGTH: 384
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (73)..(73)
<223> OTHER INFORMATION: X can be S, K or G
<220> FEATURE:
<221> NAME/KEY: MISC_FEATURE
<222> LOCATION: (102)..(102)
<223> OTHER INFORMATION: All mutants with more than 10-fold activity
      have this substitution
<220> FEATURE:
<221> NAME/KEY: MISC_FEATURE
<222> LOCATION: (103)..(103)
<223> OTHER INFORMATION: X can be T or S
<220> FEATURE:
<221> NAME/KEY: MISC_FEATURE
<222> LOCATION: (104)..(104)
<223> OTHER INFORMATION: X can be D, A, T or N
<220> FEATURE:
<221> NAME/KEY: MISC_FEATURE
<222> LOCATION: (130)..(130)
<223> OTHER INFORMATION: X can be G or S
<220> FEATURE:
<221> NAME/KEY: MISC_FEATURE
<222> LOCATION: (165)..(165)
<223> OTHER INFORMATION: X can be S or N
<220> FEATURE:
<221> NAME/KEY: MISC_FEATURE
<222> LOCATION: (168)..(168)
<223> OTHER INFORMATION: X can be T or A
<220> FEATURE:
<221> NAME/KEY: MISC_FEATURE
<222> LOCATION: (169)..(169)
<223> OTHER INFORMATION: X can be D, N, or G
<220> FEATURE:
<221> NAME/KEY: MISC_FEATURE
<222> LOCATION: (172)..(172)
<223> OTHER INFORMATION: X can be Q or D
<220> FEATURE:
<221> NAME/KEY: MISC_FEATURE
<222> LOCATION: (179)..(179)
<223> OTHER INFORMATION: X can be D, S, or H

<400> SEQUENCE: 36

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
            35                  40                  45

Leu Gly Val Pro Ala Pro Gln Val Val Ser Val Ser Val Asp Gly Ala
50                  55                  60

Ser Asn Gln Pro Thr Gly Asp Pro Xaa Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Xaa Xaa Ala Gly Phe Leu Asp Ala Ile Thr
            100                 105                 110

Thr Ala Ile His Asp Pro Thr Leu Lys Pro Ser Val Ser Ile Ser
            115                 120                 125

Trp Xaa Gly Pro Glu Asp Ser Trp Thr Ser Ala Ala Ile Ala Ala Met
130                 135                 140

Asn Arg Ala Phe Leu Asp Ala Ala Leu Gly Val Thr Val Leu Ala
145                 150                 155                 160

Ala Ala Gly Asp Xaa Gly Ser Xaa Xaa Gly Glu Xaa Asp Gly Leu Tyr
                165                 170                 175

His Val Xaa Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
            195                 200                 205

Asn Asp Gly Pro Asp Gly Gly Ala Thr Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
            245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
            275                 280                 285

Ala Arg Ile Asn Gln Lys Leu Gly Lys Ala Val Gly Tyr Leu Asn Pro
            290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
            325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
            355                 360                 365

Asn Leu Tyr Phe Gln Ser Gly Ala Leu Glu His His His His His His
370                 375                 380

<210> SEQ ID NO 37
<211> LENGTH: 384
<212> TYPE: PRT
<213> ORGANISM: Artificial Sequence
<220> FEATURE:
<223> OTHER INFORMATION: Synthetic

```
<220> FEATURE:
<221> NAME/KEY: MISC_FEATURE
<222> LOCATION: (73)..(73)
<223> OTHER INFORMATION: X is S, K, or G
<220> FEATURE:
<221> NAME/KEY: MISC_FEATURE
<222> LOCATION: (102)..(102)
<223> OTHER INFORMATION: All mutants with more than 20-fold activity
      increase have this substitution together with 358 substitution
<220> FEATURE:
<221> NAME/KEY: MISC_FEATURE
<222> LOCATION: (103)..(103)
<223> OTHER INFORMATION: X is T or S
<220> FEATURE:
<221> NAME/KEY: MISC_FEATURE
<222> LOCATION: (104)..(104)
<223> OTHER INFORMATION: X is D, A, T or N
<220> FEATURE:
<221> NAME/KEY: MISC_FEATURE
<222> LOCATION: (130)..(130)
<223> OTHER INFORMATION: X is G or S
<220> FEATURE:
<221> NAME/KEY: MISC_FEATURE
<222> LOCATION: (165)..(165)
<223> OTHER INFORMATION: X is S or N
<220> FEATURE:
<221> NAME/KEY: MISC_FEATURE
<222> LOCATION: (168)..(168)
<223> OTHER INFORMATION: X is T or A
<220> FEATURE:
<221> NAME/KEY: MISC_FEATURE
<222> LOCATION: (169)..(169)
<223> OTHER INFORMATION: X is N or G (most have G at this position)
<220> FEATURE:
<221> NAME/KEY: MISC_FEATURE
<222> LOCATION: (172)..(172)
<223> OTHER INFORMATION: X is Q or D
<220> FEATURE:
<221> NAME/KEY: MISC_FEATURE
<222> LOCATION: (179)..(179)
<223> OTHER INFORMATION: X is D, S, or H

<400> SEQUENCE: 37

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Xaa Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Xaa Xaa Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Xaa Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Xaa Gly Ser Xaa Xaa Gly Glu Xaa Asp Gly Leu Tyr
                165                 170                 175

His Val Xaa Phe Pro Ala Ala Ser Pro Tyr Val Leu Ala Cys Gly Gly
            180                 185                 190
```

-continued

```
Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
        355                 360                 365

Asn Leu Tyr Phe Gln Ser Gly Ala Leu Glu His His His His His
    370                 375                 380
```

```
<210> SEQ ID NO 38
<211> LENGTH: 384
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (73)..(73)
<223> OTHER INFORMATION: X is S, K, or G
<220> FEATURE:
<221> NAME/KEY: MISC_FEATURE
<222> LOCATION: (102)..(102)
<223> OTHER INFORMATION: All mutants with more than 50-fold activity
      increase have this substitution together with 319, 358, and 368
      substitutions
<220> FEATURE:
<221> NAME/KEY: MISC_FEATURE
<222> LOCATION: (103)..(103)
<223> OTHER INFORMATION: X is T or S
<220> FEATURE:
<221> NAME/KEY: MISC_FEATURE
<222> LOCATION: (104)..(104)
<223> OTHER INFORMATION: X is D, A, T, or N
<220> FEATURE:
<221> NAME/KEY: MISC_FEATURE
<222> LOCATION: (165)..(165)
<223> OTHER INFORMATION: X is S or N
<220> FEATURE:
<221> NAME/KEY: MISC_FEATURE
<222> LOCATION: (168)..(168)
<223> OTHER INFORMATION: X is T or A
<220> FEATURE:
<221> NAME/KEY: MISC_FEATURE
<222> LOCATION: (172)..(172)
<223> OTHER INFORMATION: X is Q or D

<400> SEQUENCE: 38
```

```
Ala Ala Pro Thr Ala Tyr Thr Pro Leu Asp Val Ala Gln Ala Tyr Gln
1               5                  10                  15
```

Phe Pro Glu Gly Leu Asp Gly Gln Gly Gln Cys Ile Ala Ile Ile Glu
                20                  25                  30

Leu Gly Gly Gly Tyr Asp Glu Ala Ser Leu Ala Gln Tyr Phe Ala Ser
            35                  40                  45

Leu Gly Val Pro Ala Pro Gln Val Val Ser Val Ser Val Asp Gly Ala
 50                  55                  60

Ser Asn Gln Pro Thr Gly Asp Pro Xaa Gly Pro Asp Gly Glu Val Glu
 65                  70                  75                  80

Leu Asp Ile Glu Val Ala Gly Ala Leu Ala Pro Gly Ala Lys Phe Ala
                85                  90                  95

Val Tyr Phe Ala Pro Asp Xaa Xaa Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
130                 135                 140

Asn Arg Ala Phe Leu Asp Ala Ala Ala Leu Gly Val Thr Val Leu Ala
145                 150                 155                 160

Ala Ala Gly Asp Xaa Gly Ser Xaa Gly Gly Glu Xaa Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
        355                 360                 365

Asn Leu Tyr Phe Gln Ser Gly Ala Leu Glu His His His His His His
370                 375                 380

<210> SEQ ID NO 39
<211> LENGTH: 384
<212> TYPE: PRT
<213> ORGANISM: Artificial Sequence
<220> FEATURE:
<223> OTHER INFORMATION: Synthetic

<400> SEQUENCE: 39

```
Ala Ala Pro Thr Ala Tyr Thr Pro Leu Asp Val Ala Gln Ala Tyr Gln
  1               5                  10                  15

Phe Pro Glu Gly Leu Asp Gly Gln Gly Gln Cys Ile Ala Ile Ile Glu
             20                  25                  30

Leu Gly Gly Gly Tyr Asp Glu Ala Ser Leu Ala Gln Tyr Phe Ala Ser
         35                  40                  45

Leu Gly Val Pro Ala Pro Gln Val Val Ser Val Ser Val Asp Gly Ala
 50                  55                  60

Ser Asn Gln Pro Thr Gly Asp Pro Ser Gly Pro Asp Gly Glu Val Glu
 65                  70                  75                  80

Leu Asp Ile Glu Val Ala Gly Ala Leu Ala Pro Gly Ala Lys Phe Ala
                 85                  90                  95

Val Tyr Phe Ala Pro Asn Thr Asp Ala Gly Phe Leu Asp Ala Ile Thr
                100                 105                 110

Thr Ala Ile His Asp Pro Thr Leu Lys Pro Ser Val Val Ser Ile Ser
             115                 120                 125

Trp Gly Gly Pro Glu Asp Ser Trp Thr Ser Ala Ala Ile Ala Ala Met
130                 135                 140

Asn Arg Ala Phe Leu Asp Ala Ala Leu Gly Val Thr Val Leu Ala
145                 150                 155                 160

Ala Ala Gly Asp Ser Gly Ser Thr Asn Gly Glu Gln Asp Gly Leu Tyr
                165                 170                 175

His Val Asp Phe Pro Ala Ala Ser Pro Tyr Val Leu Ala Cys Gly Gly
            180                 185                 190

Thr Arg Leu Val Ala Ser Gly Arg Ile Ala Gln Thr Val Trp
        195                 200                 205

Asn Asp Gly Pro Asp Gly Gly Ala Thr Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
        355                 360                 365

Asn Leu Tyr Phe Gln Ser Gly Ala Leu Glu His His His His His
370                 375                 380
```

<210> SEQ ID NO 40
<211> LENGTH: 384
<212> TYPE: PRT
<213> ORGANISM: Artificial Sequence
<220> FEATURE:

<223> OTHER INFORMATION: Synthetic

<400> SEQUENCE: 40

```
Ala Ala Pro Thr Ala Tyr Thr Pro Leu Asp Val Ala Gln Ala Tyr Gln
1               5                   10                  15
Phe Pro Glu Gly Leu Asp Gly Gln Gly Gln Cys Ile Ala Ile Ile Glu
            20                  25                  30
Leu Gly Gly Gly Tyr Asp Glu Ala Ser Leu Ala Gln Tyr Phe Ala Ser
        35                  40                  45
Leu Gly Val Pro Ala Pro Gln Val Val Ser Val Ser Val Asp Gly Ala
    50                  55                  60
Ser Asn Gln Pro Thr Gly Asp Pro Ser Gly Pro Asp Gly Glu Val Glu
65                  70                  75                  80
Leu Asp Ile Glu Val Ala Gly Ala Leu Ala Pro Gly Ala Lys Phe Ala
                85                  90                  95
Val Tyr Phe Ala Pro Asp Thr Asp Ala Gly Phe Leu Asp Ala Ile Thr
            100                 105                 110
Thr Ala Ile His Asp Pro Thr Leu Lys Pro Ser Val Ser Ile Ser
        115                 120                 125
Trp Gly Gly Pro Glu Asp Ser Trp Thr Ser Ala Ala Ile Ala Ala Met
    130                 135                 140
Asn Arg Ala Phe Leu Asp Ala Ala Leu Gly Val Thr Val Leu Ala
145                 150                 155                 160
Ala Ala Gly Asp Ser Gly Ser Thr Asp Gly Glu Gln Asp Gly Leu Tyr
                165                 170                 175
His Val Asp Phe Pro Ala Ala Ser Pro Tyr Val Leu Ala Cys Gly Gly
            180                 185                 190
Thr Arg Leu Val Ala Ser Gly Gly Arg Ile Ala Gln Glu Thr Val Trp
        195                 200                 205
Asn Asp Gly Pro Asp Gly Gly Ala Thr Gly Gly Val Ser Arg Ile
    210                 215                 220
Phe Pro Leu Pro Ala Trp Gln Glu His Ala Asn Val Pro Pro Ser Ala
225                 230                 235                 240
Asn Pro Gly Ala Ser Ser Gly Arg Gly Val Pro Asp Leu Ala Gly Asn
                245                 250                 255
Ala Asp Pro Ala Thr Gly Tyr Glu Val Val Ile Asp Gly Glu Ala Thr
            260                 265                 270
Val Ile Gly Gly Thr Ser Ala Val Ala Pro Leu Phe Ala Ala Leu Val
        275                 280                 285
Ala Arg Ile Asn Gln Lys Leu Gly Lys Ala Val Gly Tyr Leu Asn Pro
    290                 295                 300
Thr Leu Tyr Gln Leu Pro Ala Asp Val Phe His Asp Ile Thr Glu Gly
305                 310                 315                 320
Asn Asn Asp Ile Ala Asn Arg Ala Gln Ile Tyr Gln Ala Gly Pro Gly
                325                 330                 335
Trp Asp Pro Cys Thr Gly Leu Gly Ser Pro Ile Gly Val Arg Leu Leu
            340                 345                 350
Gln Ala Leu Leu Pro Ser Ala Ser Gln Pro Gln Pro Gly Ser Thr Glu
        355                 360                 365
Asn Leu Tyr Phe Gln Ser Gly Ala Leu Glu His His His His His
    370                 375                 380
```

<210> SEQ ID NO 41
<211> LENGTH: 384

<212> TYPE: PRT
<213> ORGANISM: Artificial Sequence
<220> FEATURE:
<223> OTHER INFORMATION: Synthetic

<400> SEQUENCE: 41

```
Ala Ala Pro Thr Ala Tyr Thr Pro Leu Asp Val Ala Gln Ala Tyr Gln
 1               5                  10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Ser Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asn Thr Asp Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Gly Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val Asp Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
        355                 360                 365

Asn Leu Tyr Phe Gln Ser Gly Ala Leu Glu His His His His His
    370                 375                 380
```

<210> SEQ ID NO 42
<211> LENGTH: 384
<212> TYPE: PRT
<213> ORGANISM: Artificial Sequence
<220> FEATURE:
<223> OTHER INFORMATION: Synthetic

<400> SEQUENCE: 42

```
Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Ser Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asn Thr Asp Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Gly Gly Pro Glu Asp Ser Trp Thr Ser Ala Ala Ile Ala Ala Met
    130                 135                 140

Asn Arg Ala Phe Leu Asp Ala Ala Leu Gly Val Thr Val Leu Ala
145                 150                 155                 160

Ala Ala Gly Asp Ser Gly Ser Ala Asp Gly Glu Gln Asp Gly Leu Tyr
                165                 170                 175

His Val Asp Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
        355                 360                 365
```

```
Asn Leu Tyr Phe Gln Ser Gly Ala Leu Glu His His His His His His
    370                 375                 380
```

<210> SEQ ID NO 43
<211> LENGTH: 384
<212> TYPE: PRT
<213> ORGANISM: Artificial Sequence
<220> FEATURE:
<223> OTHER INFORMATION: Synthetic

<400> SEQUENCE: 43

```
Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Ser Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asn Thr Ala Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Gly Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Asp Gly Glu Gln Asp Gly Leu Tyr
                165                 170                 175

His Val Asp Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Ala Thr Gly Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350
```

Gln Ala Leu Leu Pro Ser Ala Ser Gln Pro Gln Pro Gly Ser Thr Glu
            355                 360                 365

Asn Leu Tyr Phe Gln Ser Gly Ala Leu Glu His His His His His His
        370                 375                 380

<210> SEQ ID NO 44
<211> LENGTH: 384
<212> TYPE: PRT
<213> ORGANISM: Artificial Sequence
<220> FEATURE:
<223> OTHER INFORMATION: Synthetic

<400> SEQUENCE: 44

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Ser Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asn Thr Asp Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Asp Gly Glu Gln Asp Gly Leu Tyr
                165                 170                 175

His Val Ser Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
            355                 360                 365

Asn Leu Tyr Phe Gln Ser Gly Ala Leu Glu His His His His His His
            370                 375                 380

<210> SEQ ID NO 45
<211> LENGTH: 384
<212> TYPE: PRT
<213> ORGANISM: Artificial Sequence
<220> FEATURE:
<223> OTHER INFORMATION: Synthetic

<400> SEQUENCE: 45

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
            35                  40                  45

Leu Gly Val Pro Ala Pro Gln Val Val Ser Val Ser Val Asp Gly Ala
            50                  55                  60

Ser Asn Gln Pro Thr Gly Asp Pro Ser Gly Pro Asp Gly Glu Val Glu
65                  70                  75                  80

Leu Asp Ile Glu Val Ala Gly Ala Leu Ala Pro Gly Ala Lys Phe Ala
            85                  90                  95

Val Tyr Phe Ala Pro Asn Thr Asp Ala Gly Phe Leu Asp Ala Ile Thr
            100                 105                 110

Thr Ala Ile His Asp Pro Thr Leu Lys Pro Ser Val Val Ser Ile Ser
            115                 120                 125

Trp Gly Gly Pro Glu Asp Ser Trp Thr Ser Ala Ala Ile Ala Ala Met
            130                 135                 140

Asn Arg Ala Phe Leu Asp Ala Ala Leu Gly Val Thr Val Leu Ala
145                 150                 155                 160

Ala Ala Gly Asp Ser Gly Ser Thr Gly Gly Glu Gln Asp Gly Leu Tyr
            165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
            195                 200                 205

Asn Asp Gly Pro Asp Gly Gly Ala Thr Gly Gly Val Ser Arg Ile
            210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
            245                 250                 255

Ala Asp Pro Ala Thr Gly Tyr Glu Val Ile Asp Gly Glu Ala Thr
            260                 265                 270

Val Ile Gly Gly Thr Ser Ala Val Ala Pro Leu Phe Ala Ala Leu Val
            275                 280                 285

Ala Arg Ile Asn Gln Lys Leu Gly Lys Ala Val Gly Tyr Leu Asn Pro
            290                 295                 300

Thr Leu Tyr Gln Leu Pro Ala Asp Val Phe His Asp Ile Thr Glu Gly
305                 310                 315                 320

```
Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
        355                 360                 365

Asn Leu Tyr Phe Gln Ser Gly Ala Leu Glu His His His His His His
370                 375                 380
```

<210> SEQ ID NO 46
<211> LENGTH: 384
<212> TYPE: PRT
<213> ORGANISM: Artificial Sequence
<220> FEATURE:
<223> OTHER INFORMATION: Synthetic

<400> SEQUENCE: 46

```
Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Ser Val Ser Val Asp Gly Ala
    50                  55                  60

Ser Asn Gln Pro Thr Gly Asp Pro Ser Gly Pro Asp Gly Glu Val Glu
65              70                  75                  80

Leu Asp Ile Glu Val Ala Gly Ala Leu Ala Pro Gly Ala Lys Phe Ala
                85                  90                  95

Val Tyr Phe Ala Pro Asp Thr Asp Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Gly Gly Pro Glu Asp Ser Trp Thr Ser Ala Ala Ile Ala Ala Met
130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Asp Gly Glu Asp Asp Gly Leu Tyr
                165                 170                 175

His Val Asp Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Ala Thr Gly Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
290                 295                 300
```

```
Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
            325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
            355                 360                 365

Asn Leu Tyr Phe Gln Ser Gly Ala Leu Glu His His His His His His
            370                 375                 380
```

<210> SEQ ID NO 47
<211> LENGTH: 384
<212> TYPE: PRT
<213> ORGANISM: Artificial Sequence
<220> FEATURE:
<223> OTHER INFORMATION: Synthetic

<400> SEQUENCE: 47

```
Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Ser Gly Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Asp Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Gly Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Asn Gly Glu Gln Asp Gly Leu Tyr
                165                 170                 175

His Val Asp Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285
```

```
Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro Gly Ser Thr Glu
                355                 360                 365

Asn Leu Tyr Phe Gln Ser Gly Ala Leu Glu His His His His His His
370                 375                 380
```

<210> SEQ ID NO 48
<211> LENGTH: 384
<212> TYPE: PRT
<213> ORGANISM: Artificial Sequence
<220> FEATURE:
<223> OTHER INFORMATION: Synthetic

<400> SEQUENCE: 48

```
Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
                20                  25                  30

Leu Gly Gly Gly Tyr Asp Glu Ala Ser Leu Ala Gln Tyr Phe Ala Ser
                35                  40                  45

Leu Gly Val Pro Ala Pro Gln Val Val Ser Val Ser Val Asp Gly Ala
            50                  55                  60

Ser Asn Gln Pro Thr Gly Asp Pro Ser Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Ala Ala Gly Phe Leu Asp Ala Ile Thr
                100                 105                 110

Thr Ala Ile His Asp Pro Thr Leu Lys Pro Ser Val Val Ser Ile Ser
            115                 120                 125

Trp Gly Gly Pro Glu Asp Ser Trp Thr Ser Ala Ala Ile Ala Ala Met
130                 135                 140

Asn Arg Ala Phe Leu Asp Ala Ala Leu Gly Val Thr Val Leu Ala
145                 150                 155                 160

Ala Ala Gly Asp Ser Gly Ser Thr Asp Gly Glu Gln Asp Gly Leu Tyr
                165                 170                 175

His Val Asp Phe Pro Ala Ala Ser Pro Tyr Val Leu Ala Cys Gly Gly
                180                 185                 190

Thr Arg Leu Val Ala Ser Gly Gly Arg Ile Ala Gln Glu Thr Val Trp
            195                 200                 205

Asn Asp Gly Pro Asp Gly Ala Thr Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
                260                 265                 270
```

-continued

```
Val Ile Gly Gly Thr Ser Ala Val Ala Pro Leu Phe Ala Ala Leu Val
            275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
        355                 360                 365

Asn Leu Tyr Phe Gln Ser Gly Ala Leu Glu His His His His His His
    370                 375                 380
```

<210> SEQ ID NO 49
<211> LENGTH: 384
<212> TYPE: PRT
<213> ORGANISM: Artificial Sequence
<220> FEATURE:
<223> OTHER INFORMATION: Synthetic

<400> SEQUENCE: 49

```
Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Ser Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Ala Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Gly Gly Pro Glu Asp Ser Trp Thr Ser Ala Ala Ile Ala Ala Met
    130                 135                 140

Asn Arg Ala Phe Leu Asp Ala Ala Leu Gly Val Thr Val Leu Ala
145                 150                 155                 160

Ala Ala Gly Asp Ser Gly Ser Thr Asn Gly Glu Gln Asp Gly Leu Tyr
                165                 170                 175

His Val Asp Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255
```

```
Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
        355                 360                 365

Asn Leu Tyr Phe Gln Ser Gly Ala Leu Glu His His His His His His
    370                 375                 380
```

<210> SEQ ID NO 50
<211> LENGTH: 384
<212> TYPE: PRT
<213> ORGANISM: Artificial Sequence
<220> FEATURE:
<223> OTHER INFORMATION: Synthetic

<400> SEQUENCE: 50

```
Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Ser Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asn Thr Asp Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240
```

Asn Pro Gly Ala Ser Ser Gly Arg Gly Val Pro Asp Leu Ala Gly Asn
            245                 250                 255

Ala Asp Pro Ala Thr Gly Tyr Glu Val Val Ile Asp Gly Glu Ala Thr
        260                 265                 270

Val Ile Gly Gly Thr Ser Ala Val Ala Pro Leu Phe Ala Ala Leu Val
    275                 280                 285

Ala Arg Ile Asn Gln Lys Leu Gly Lys Ala Val Gly Tyr Leu Asn Pro
290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
        355                 360                 365

Asn Leu Tyr Phe Gln Ser Gly Ala Leu Glu His His His His His His
    370                 375                 380

<210> SEQ ID NO 51
<211> LENGTH: 384
<212> TYPE: PRT
<213> ORGANISM: Artificial Sequence
<220> FEATURE:
<223> OTHER INFORMATION: Synthetic

<400> SEQUENCE: 51

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Ser Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asn Thr Asp Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Gly Gly Pro Glu Asp Ser Trp Thr Ser Ala Ala Ile Ala Ala Met
    130                 135                 140

Asn Arg Ala Phe Leu Asp Ala Ala Leu Gly Val Thr Val Leu Ala
145                 150                 155                 160

Ala Ala Gly Asp Asn Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Arg Ile Ala Gln Glu Thr Val Trp
        195                 200                 205

Asn Asp Gly Pro Asp Gly Ala Thr Gly Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
            245                 250                 255

Ala Asp Pro Ala Thr Gly Tyr Glu Val Val Ile Asp Gly Glu Ala Thr
        260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
        355                 360                 365

Asn Leu Tyr Phe Gln Ser Gly Ala Leu Glu His His His His His His
370                 375                 380

<210> SEQ ID NO 52
<211> LENGTH: 384
<212> TYPE: PRT
<213> ORGANISM: Artificial Sequence
<220> FEATURE:
<223> OTHER INFORMATION: Synthetic

<400> SEQUENCE: 52

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Ser Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Asp Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Gly Gly Pro Glu Asp Ser Trp Thr Ser Ala Ala Ile Ala Ala Met
    130                 135                 140

Asn Arg Ala Phe Leu Asp Ala Ala Leu Gly Val Thr Val Leu Ala
145                 150                 155                 160

Ala Ala Gly Asp Ser Gly Ser Thr Gly Gly Glu Asp Asp Gly Leu Tyr
                165                 170                 175

His Val Asp Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

```
Asn Asp Gly Pro Asp Gly Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
        355                 360                 365

Asn Leu Tyr Phe Gln Ser Gly Ala Leu Glu His His His His His His
370                 375                 380

<210> SEQ ID NO 53
<211> LENGTH: 384
<212> TYPE: PRT
<213> ORGANISM: Artificial Sequence
<220> FEATURE:
<223> OTHER INFORMATION: Synthetic

<400> SEQUENCE: 53

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Ser Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Asp Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190
```

```
Thr Arg Leu Val Ala Ser Gly Gly Arg Ile Ala Gln Glu Thr Val Trp
            195                 200                 205

Asn Asp Gly Pro Asp Gly Gly Ala Thr Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Ile Asp Gly Glu Ala Thr
            260                 265                 270

Val Ile Gly Gly Thr Ser Ala Val Ala Pro Leu Phe Ala Ala Leu Val
            275                 280                 285

Ala Arg Ile Asn Gln Lys Leu Gly Lys Ala Val Gly Tyr Leu Asn Pro
290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
            355                 360                 365

Asn Leu Tyr Phe Gln Ser Gly Ala Leu Glu His His His His His
            370                 375                 380

<210> SEQ ID NO 54
<211> LENGTH: 384
<212> TYPE: PRT
<213> ORGANISM: Artificial Sequence
<220> FEATURE:
<223> OTHER INFORMATION: Synthetic

<400> SEQUENCE: 54

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Ser Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Ala Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Gly Gly Pro Glu Asp Ser Trp Thr Ser Ala Ala Ile Ala Ala Met
    130                 135                 140

Asn Arg Ala Phe Leu Asp Ala Ala Leu Gly Val Thr Val Leu Ala
145                 150                 155                 160

Ala Ala Gly Asp Ser Gly Ser Thr Asn Gly Glu Asp Asp Gly Leu Tyr
                165                 170                 175
```

```
His Val Asp Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
        355                 360                 365

Asn Leu Tyr Phe Gln Ser Gly Ala Leu Glu His His His His His His
    370                 375                 380
```

<210> SEQ ID NO 55
<211> LENGTH: 384
<212> TYPE: PRT
<213> ORGANISM: Artificial Sequence
<220> FEATURE:
<223> OTHER INFORMATION: Synthetic

<400> SEQUENCE: 55

```
Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Ser Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asn Thr Asp Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160
```

```
Ala Ala Gly Asp Asn Gly Ser Thr Gly Gly Glu Gln Asp Gly Leu Tyr
            165                 170                 175

His Val His Phe Pro Ala Ala Ser Pro Tyr Val Leu Ala Cys Gly Gly
            180                 185                 190

Thr Arg Leu Val Ala Ser Gly Arg Ile Ala Gln Glu Thr Val Trp
            195                 200                 205

Asn Asp Gly Pro Asp Gly Gly Ala Thr Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
            245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
            275                 280                 285

Ala Arg Ile Asn Gln Lys Leu Gly Lys Ala Val Gly Tyr Leu Asn Pro
            290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
            325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
            355                 360                 365

Asn Leu Tyr Phe Gln Ser Gly Ala Leu Glu His His His His His His
370                 375                 380

<210> SEQ ID NO 56
<211> LENGTH: 384
<212> TYPE: PRT
<213> ORGANISM: Artificial Sequence
<220> FEATURE:
<223> OTHER INFORMATION: Synthetic

<400> SEQUENCE: 56

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
            35                  40                  45

Leu Gly Val Pro Ala Pro Gln Val Val Ser Val Ser Val Asp Gly Ala
        50                  55                  60

Ser Asn Gln Pro Thr Gly Asp Pro Ser Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Ala Gly Phe Leu Asp Ala Ile Thr
            100                 105                 110

Thr Ala Ile His Asp Pro Thr Leu Lys Pro Ser Val Val Ser Ile Ser
            115                 120                 125

Trp Gly Gly Pro Glu Asp Ser Trp Thr Ser Ala Ala Ile Ala Ala Met
        130                 135                 140
```

```
Asn Arg Ala Phe Leu Asp Ala Ala Leu Gly Val Thr Val Leu Ala
145                 150                 155                 160

Ala Ala Gly Asp Ser Gly Ser Thr Gly Gly Glu Asp Asp Gly Leu Tyr
            165                 170                 175

His Val Asp Phe Pro Ala Ala Ser Pro Tyr Val Leu Ala Cys Gly Gly
            180                 185                 190

Thr Arg Leu Val Ala Ser Gly Arg Ile Ala Gln Glu Thr Val Trp
        195                 200                 205

Asn Asp Gly Pro Asp Gly Gly Ala Thr Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
            245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
            275                 280                 285

Ala Arg Ile Asn Gln Lys Leu Gly Lys Ala Val Gly Tyr Leu Asn Pro
            290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
            355                 360                 365

Asn Leu Tyr Phe Gln Ser Gly Ala Leu Glu His His His His His
            370                 375                 380

<210> SEQ ID NO 57
<211> LENGTH: 384
<212> TYPE: PRT
<213> ORGANISM: Artificial Sequence
<220> FEATURE:
<223> OTHER INFORMATION: Synthetic

<400> SEQUENCE: 57

Ala Ala Pro Thr Ala Tyr Thr Pro Leu Asp Val Ala Gln Ala Tyr Gln
1               5                   10                  15

Phe Pro Glu Gly Leu Asp Gly Gln Gly Cys Ile Ala Ile Ile Glu
            20                  25                  30

Leu Gly Gly Gly Tyr Asp Glu Ala Ser Leu Ala Gln Tyr Phe Ala Ser
            35                  40                  45

Leu Gly Val Pro Ala Pro Gln Val Val Ser Val Ser Val Asp Gly Ala
        50                  55                  60

Ser Asn Gln Pro Thr Gly Asp Pro Ser Gly Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Asp Ala Gly Phe Leu Asp Ala Ile Thr
            100                 105                 110

Thr Ala Ile His Asp Pro Thr Leu Lys Pro Ser Val Val Ser Ile Ser
            115                 120                 125
```

Trp Ser Gly Pro Glu Asp Ser Trp Thr Ser Ala Ala Ile Ala Ala Met
130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Asp Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
        355                 360                 365

Asn Leu Tyr Phe Gln Ser Gly Ala Leu Glu His His His His His His
370                 375                 380

<210> SEQ ID NO 58
<211> LENGTH: 384
<212> TYPE: PRT
<213> ORGANISM: Artificial Sequence
<220> FEATURE:
<223> OTHER INFORMATION: Synthetic

<400> SEQUENCE: 58

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Val Ser Val Asp Gly Ala
    50                  55                  60

Ser Asn Gln Pro Thr Gly Asp Pro Ser Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Asp Ala Gly Phe Leu Asp Ala Ile Thr
            100                 105                 110

-continued

Thr Ala Ile His Asp Pro Thr Leu Lys Pro Ser Val Ser Ile Ser
            115                 120                 125

Trp Ser Gly Pro Glu Asp Ser Trp Thr Ser Ala Ile Ala Ala Met
130                 135                 140

Asn Arg Ala Phe Leu Asp Ala Ala Leu Gly Val Thr Val Leu Ala
145                 150                 155                 160

Ala Ala Gly Asp Asn Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
            195                 200                 205

Asn Asp Gly Pro Asp Gly Gly Ala Thr Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
                260                 265                 270

Val Ile Gly Gly Thr Ser Ala Val Ala Pro Leu Phe Ala Ala Leu Val
            275                 280                 285

Ala Arg Ile Asn Gln Lys Leu Gly Lys Ala Val Gly Tyr Leu Asn Pro
            290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro Gly Ser Thr Glu
            355                 360                 365

Asn Leu Tyr Phe Gln Ser Gly Ala Leu Glu His His His His His His
370                 375                 380

<210> SEQ ID NO 59
<211> LENGTH: 384
<212> TYPE: PRT
<213> ORGANISM: Artificial Sequence
<220> FEATURE:
<223> OTHER INFORMATION: Synthetic

<400> SEQUENCE: 59

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
                20                  25                  30

Leu Gly Gly Gly Tyr Asp Glu Ala Ser Leu Ala Gln Tyr Phe Ala Ser
            35                  40                  45

Leu Gly Val Pro Ala Pro Gln Val Val Ser Val Ser Val Asp Gly Ala
        50                  55                  60

Ser Asn Gln Pro Thr Gly Asp Pro Ser Gly Pro Asp Gly Glu Val Glu
65                  70                  75                  80

Leu Asp Ile Glu Val Ala Gly Ala Leu Ala Pro Gly Ala Lys Phe Ala
                85                  90                  95

```
Val Tyr Phe Ala Pro Asp Thr Ala Ala Gly Phe Leu Asp Ala Ile Thr
                100                 105                 110

Thr Ala Ile His Asp Pro Thr Leu Lys Pro Ser Val Val Ser Ile Ser
            115                 120                 125

Trp Ser Gly Pro Glu Asp Ser Trp Thr Ser Ala Ala Ile Ala Ala Met
        130                 135                 140

Asn Arg Ala Phe Leu Asp Ala Ala Leu Gly Val Thr Val Leu Ala
145                 150                 155                 160

Ala Ala Gly Asp Ser Gly Ser Thr Gly Gly Glu Asp Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
        355                 360                 365

Asn Leu Tyr Phe Gln Ser Gly Ala Leu Glu His His His His His
370                 375                 380

<210> SEQ ID NO 60
<211> LENGTH: 384
<212> TYPE: PRT
<213> ORGANISM: Artificial Sequence
<220> FEATURE:
<223> OTHER INFORMATION: Synthetic

<400> SEQUENCE: 60

Ala Ala Pro Thr Ala Tyr Thr Pro Leu Asp Val Ala Gln Ala Tyr Gln
1               5                   10                  15

Phe Pro Glu Gly Leu Asp Gly Gln Gly Cys Ile Ala Ile Ile Glu
                20                  25                  30

Leu Gly Gly Gly Tyr Asp Glu Ala Ser Leu Ala Gln Tyr Phe Ala Ser
            35                  40                  45

Leu Gly Val Pro Ala Pro Gln Val Val Ser Val Ser Val Asp Gly Ala
        50                  55                  60

Ser Asn Gln Pro Thr Gly Asp Pro Ser Gly Pro Asp Gly Glu Val Glu
65                  70                  75                  80
```

Leu Asp Ile Glu Val Ala Gly Ala Leu Ala Pro Gly Ala Lys Phe Ala
            85                  90                  95

Val Tyr Phe Ala Pro Asp Thr Asp Ala Gly Phe Leu Asp Ala Ile Thr
        100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
130                 135                 140

Asn Arg Ala Phe Leu Asp Ala Ala Leu Gly Val Thr Val Leu Ala
145                 150                 155                 160

Ala Ala Gly Asp Asn Gly Ser Thr Gly Gly Glu Asp Gly Leu Tyr
                165                 170                 175

His Val His Phe Pro Ala Ala Ser Pro Tyr Val Leu Ala Cys Gly Gly
        180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
        210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
        290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
        355                 360                 365

Asn Leu Tyr Phe Gln Ser Gly Ala Leu Glu His His His His His
        370                 375                 380

<210> SEQ ID NO 61
<211> LENGTH: 384
<212> TYPE: PRT
<213> ORGANISM: Artificial Sequence
<220> FEATURE:
<223> OTHER INFORMATION: Synthetic

<400> SEQUENCE: 61

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

```
Ser Asn Gln Pro Thr Gly Asp Pro Ser Gly Pro Asp Gly Glu Val Glu
 65                  70                  75                  80

Leu Asp Ile Glu Val Ala Gly Ala Leu Ala Pro Gly Ala Lys Phe Ala
                 85                  90                  95

Val Tyr Phe Ala Pro Asp Thr Ala Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Leu Gly Val Thr Val Leu Ala
145                 150                 155                 160

Ala Ala Gly Asp Asn Gly Ser Thr Gly Gly Glu Asp Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
        355                 360                 365

Asn Leu Tyr Phe Gln Ser Gly Ala Leu Glu His His His His
370                 375                 380

<210> SEQ ID NO 62
<211> LENGTH: 384
<212> TYPE: PRT
<213> ORGANISM: Artificial Sequence
<220> FEATURE:
<223> OTHER INFORMATION: Synthetic

<400> SEQUENCE: 62

Ala Ala Pro Thr Ala Tyr Thr Pro Leu Asp Val Ala Gln Ala Tyr Gln
 1               5                  10                  15

Phe Pro Glu Gly Leu Asp Gly Gln Gly Gln Cys Ile Ala Ile Ile Glu
                20                  25                  30

Leu Gly Gly Gly Tyr Asp Glu Ala Ser Leu Ala Gln Tyr Phe Ala Ser
            35                  40                  45
```

Leu Gly Val Pro Ala Pro Gln Val Ser Val Ser Val Asp Gly Ala
    50              55                  60

Ser Asn Gln Pro Thr Gly Asp Pro Ser Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Ser Asp Ala Gly Phe Leu Asp Ala Ile Thr
            100                 105                 110

Thr Ala Ile His Asp Pro Thr Leu Lys Pro Ser Val Ser Ile Ser
            115                 120                 125

Trp Ser Gly Pro Glu Asp Ser Trp Thr Ser Ala Ala Ile Ala Ala Met
130                 135                 140

Asn Arg Ala Phe Leu Asp Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
            195                 200                 205

Asn Asp Gly Pro Asp Gly Gly Ala Thr Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
            275                 280                 285

Ala Arg Ile Asn Gln Lys Leu Gly Lys Ala Val Gly Tyr Leu Asn Pro
290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
            355                 360                 365

Asn Leu Tyr Phe Gln Ser Gly Ala Leu Glu His His His His His
370                 375                 380

<210> SEQ ID NO 63
<211> LENGTH: 384
<212> TYPE: PRT
<213> ORGANISM: Artificial Sequence
<220> FEATURE:
<223> OTHER INFORMATION: Synthetic

<400> SEQUENCE: 63

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

-continued

Leu Gly Gly Gly Tyr Asp Glu Ala Ser Leu Ala Gln Tyr Phe Ala Ser
            35                  40                  45

Leu Gly Val Pro Ala Pro Gln Val Val Ser Val Ser Val Asp Gly Ala
 50                  55                  60

Ser Asn Gln Pro Thr Gly Asp Pro Ser Gly Pro Asp Gly Glu Val Glu
 65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Gly Phe Leu Asp Ala Ile Thr
                100                 105                 110

Thr Ala Ile His Asp Pro Thr Leu Lys Pro Ser Val Val Ser Ile Ser
                115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
                180                 185                 190

Thr Arg Leu Val Ala Ser Gly Gly Arg Ile Ala Gln Glu Thr Val Trp
    195                 200                 205

Asn Asp Gly Pro Asp Gly Gly Ala Thr Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
                260                 265                 270

Val Ile Gly Gly Thr Ser Ala Val Ala Pro Leu Phe Ala Ala Leu Val
    275                 280                 285

Ala Arg Ile Asn Gln Lys Leu Gly Lys Ala Val Gly Tyr Leu Asn Pro
290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro Gly Ser Thr Glu
                355                 360                 365

Asn Leu Tyr Phe Gln Ser Gly Ala Leu Glu His His His His His
                370                 375                 380

<210> SEQ ID NO 64
<211> LENGTH: 384
<212> TYPE: PRT
<213> ORGANISM: Artificial Sequence
<220> FEATURE:
<223> OTHER INFORMATION: Synthetic

<400> SEQUENCE: 64

Ala Ala Pro Thr Ala Tyr Thr Pro Leu Asp Val Ala Gln Ala Tyr Gln
 1               5                  10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Gly Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Ser Asp Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Arg Ile Ala Gln Glu Thr Val Trp
        195                 200                 205

Asn Asp Gly Pro Asp Gly Ala Thr Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
        355                 360                 365

Asn Leu Tyr Phe Gln Ser Gly Ala Leu Glu His His His His His
370                 375                 380

<210> SEQ ID NO 65
<211> LENGTH: 384
<212> TYPE: PRT
<213> ORGANISM: Artificial Sequence
<220> FEATURE:
<223> OTHER INFORMATION: Synthetic

<400> SEQUENCE: 65

Ala Ala Pro Thr Ala Tyr Thr Pro Leu Asp Val Ala Gln Ala Tyr Gln
1               5                   10                  15

Phe Pro Glu Gly Leu Asp Gly Gln Gly Cys Ile Ala Ile Ile Glu
            20                  25                  30

Leu Gly Gly Gly Tyr Asp Glu Ala Ser Leu Ala Gln Tyr Phe Ala Ser
                35                  40                  45

Leu Gly Val Pro Ala Pro Gln Val Val Ser Val Ser Val Asp Gly Ala
50                  55                  60

Ser Asn Gln Pro Thr Gly Asp Pro Lys Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Asn Ala Gly Phe Leu Asp Ala Ile Thr
                100                 105                 110

Thr Ala Ile His Asp Pro Thr Leu Lys Pro Ser Val Ser Ile Ser
            115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
            195                 200                 205

Asn Asp Gly Pro Asp Gly Gly Ala Thr Gly Gly Val Ser Arg Ile
            210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
                260                 265                 270

Val Ile Gly Gly Thr Ser Ala Val Ala Pro Leu Phe Ala Ala Leu Val
            275                 280                 285

Ala Arg Ile Asn Gln Lys Leu Gly Lys Ala Val Gly Tyr Leu Asn Pro
            290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
            355                 360                 365

Asn Leu Tyr Phe Gln Ser Gly Ala Leu Glu His His His His His
            370                 375                 380

<210> SEQ ID NO 66
<211> LENGTH: 384
<212> TYPE: PRT
<213> ORGANISM: Artificial Sequence
<220> FEATURE:
<223> OTHER INFORMATION: Synthetic

<400> SEQUENCE: 66

```
Ala Ala Pro Thr Ala Tyr Thr Pro Leu Asp Val Ala Gln Ala Tyr Gln
  1               5                  10                  15
Phe Pro Glu Gly Leu Asp Gly Gln Gly Cys Ile Ala Ile Ile Glu
             20                  25                  30
Leu Gly Gly Gly Tyr Asp Glu Ala Ser Leu Ala Gln Tyr Phe Ala Ser
             35                  40                  45
Leu Gly Val Pro Ala Pro Gln Val Val Ser Val Ser Val Asp Gly Ala
 50                  55                  60
Ser Asn Gln Pro Thr Gly Asp Pro Lys Gly Pro Asp Gly Glu Val Glu
 65                  70                  75                  80
Leu Asp Ile Glu Val Ala Gly Ala Leu Ala Pro Gly Ala Lys Phe Ala
                 85                  90                  95
Val Tyr Phe Ala Pro Asp Thr Thr Ala Gly Phe Leu Asp Ala Ile Thr
                100                 105                 110
Thr Ala Ile His Asp Pro Thr Leu Lys Pro Ser Val Val Ser Ile Ser
                115                 120                 125
Trp Ser Gly Pro Glu Asp Ser Trp Thr Ser Ala Ala Ile Ala Ala Met
130                 135                 140
Asn Arg Ala Phe Leu Asp Ala Ala Leu Gly Val Thr Val Leu Ala
145                 150                 155                 160
Ala Ala Gly Asp Ser Gly Ser Thr Gly Gly Glu Gln Asp Gly Leu Tyr
                165                 170                 175
His Val His Phe Pro Ala Ala Ser Pro Tyr Val Leu Ala Cys Gly Gly
                180                 185                 190
Thr Arg Leu Val Ala Ser Gly Gly Arg Ile Ala Gln Glu Thr Val Trp
                195                 200                 205
Asn Asp Gly Pro Asp Gly Gly Ala Thr Gly Gly Val Ser Arg Ile
210                 215                 220
Phe Pro Leu Pro Ala Trp Gln Glu His Ala Asn Val Pro Pro Ser Ala
225                 230                 235                 240
Asn Pro Gly Ala Ser Ser Gly Arg Gly Val Pro Asp Leu Ala Gly Asn
                245                 250                 255
Ala Asp Pro Ala Thr Gly Tyr Glu Val Val Ile Asp Gly Glu Ala Thr
                260                 265                 270
Val Ile Gly Gly Thr Ser Ala Val Ala Pro Leu Phe Ala Ala Leu Val
                275                 280                 285
Ala Arg Ile Asn Gln Lys Leu Gly Lys Ala Val Gly Tyr Leu Asn Pro
                290                 295                 300
Thr Leu Tyr Gln Leu Pro Ala Asp Val Phe His Asp Ile Thr Glu Gly
305                 310                 315                 320
Asn Asn Asp Ile Ala Asn Arg Ala Gln Ile Tyr Gln Ala Gly Pro Gly
                325                 330                 335
Trp Asp Pro Cys Thr Gly Leu Gly Ser Pro Ile Gly Val Arg Leu Leu
                340                 345                 350
Gln Ala Leu Leu Pro Ser Ala Ser Gln Pro Gln Pro Gly Ser Thr Glu
                355                 360                 365
Asn Leu Tyr Phe Gln Ser Gly Ala Leu Glu His His His His His His
                370                 375                 380

<210> SEQ ID NO 67
<211> LENGTH: 384
<212> TYPE: PRT
```

<213> ORGANISM: Homo sapiens

<400> SEQUENCE: 67

```
Ala Ala Pro Thr Ala Tyr Thr Pro Leu Asp Val Ala Gln Ala Tyr Gln
 1               5                  10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Ser Gly Pro Asp Gly Glu Val Glu
 65                  70                  75                  80

Leu Asp Ile Glu Val Ala Gly Ala Leu Ala Pro Gly Ala Lys Phe Ala
                85                  90                  95

Val Tyr Phe Ala Pro Asn Thr Asp Ala Gly Phe Leu Asp Ala Ile Thr
            100                 105                 110

Thr Ala Ile His Asp Pro Thr Leu Lys Pro Ser Val Ser Ile Ser
        115                 120                 125

Trp Gly Gly Pro Glu Asp Ser Trp Thr Ser Ala Ala Ile Ala Ala Met
    130                 135                 140

Asn Arg Ala Phe Leu Asp Ala Ala Leu Gly Val Thr Val Leu Ala
145                 150                 155                 160

Ala Ala Gly Asp Ser Gly Ser Thr Asp Gly Glu Gln Asp Gly Leu Tyr
                165                 170                 175

His Val Asp Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
        355                 360                 365

Asn Leu Tyr Phe Gln Ser Gly Ala Leu Glu His His His His His
    370                 375                 380
```

<210> SEQ ID NO 68
<211> LENGTH: 4

```
<212> TYPE: PRT
<213> ORGANISM: Artificial Sequence
<220> FEATURE:
<223> OTHER INFORMATION: Synthetic

<400> SEQUENCE: 68

Pro Gln Leu Pro
1

<210> SEQ ID NO 69
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-terminal QXL520
<220> FEATURE:
<221> NAME/KEY: MISC_FEATURE
<222> LOCATION: (6)..(6)
<223> OTHER INFORMATION: C-terminal K(5-FAM)

<400> SEQUENCE: 69

Pro Gln Pro Gln Leu Pro
1               5

<210> SEQ ID NO 70
<211> LENGTH: 12
<212> TYPE: PRT
<213> ORGANISM: Artificial Sequence
<220> FEATURE:
<223> OTHER INFORMATION: Synthetic

<400> SEQUENCE: 70

Gln Leu Gln Pro Phe Pro Gln Pro Gln Leu Pro Tyr
1               5                   10

<210> SEQ ID NO 71
<211> LENGTH: 290
<212> TYPE: PRT
<213> ORGANISM: Homo sapiens

<400> SEQUENCE: 71

Met Val Arg Val Pro Val Pro Gln Leu Gln Pro Gln Asn Pro Ser Gln
1               5                   10                  15

Gln Gln Pro Gln Glu Gln Val Pro Leu Val Gln Gln Gln Gln Phe Pro
            20                  25                  30

Gly Gln Gln Gln Pro Phe Pro Pro Gln Gln Pro Tyr Pro Gln Pro Gln
        35                  40                  45

Pro Phe Pro Ser Gln Gln Phe Tyr Leu Gln Leu Gln Pro Phe Pro Gln
    50                  55                  60

Pro Gln Leu Pro Tyr Pro Gln Pro Gln Leu Pro Tyr Pro Gln Pro Gln
65                  70                  75                  80

Leu Pro Tyr Pro Gln Pro Gln Pro Phe Arg Pro Gln Gln Pro Tyr Pro
                85                  90                  95

Gln Ser Gln Pro Gln Tyr Ser Gln Pro Gln Gln Pro Ile Ser Gln Gln
            100                 105                 110

Gln Gln Gln Gln Gln Gln Gln Gln Gln Lys Gln Gln Gln Gln
        115                 120                 125

Gln Gln Gln Ile Leu Gln Gln Ile Leu Gln Gln Gln Leu Ile Pro Cys
    130                 135                 140
```

```
                         -continued

Arg Asp Val Val Leu Gln Gln His Ser Ile Ala Tyr Gly Ser Ser Gln
145                 150                 155                 160

Val Leu Gln Gln Ser Thr Tyr Gly Leu Val Gln Gln Leu Cys Cys Gln
                165                 170                 175

Gln Leu Trp Gln Ile Pro Glu Gln Ser Arg Cys Gln Ala Ile His Asn
                180                 185                 190

Val Val His Ala Ile Ile Leu His Gln Gln Gln Gln Gln Gln Gln Gln
            195                 200                 205

Gln Gln Gln Gln Pro Leu Ser Gln Val Ser Phe Gln Gln Pro Gln Gln
        210                 215                 220

Gln Tyr Pro Ser Gly Gln Gly Ser Phe Gln Pro Ser Gln Gln Asn Pro
225                 230                 235                 240

Gln Ala Gln Gly Ser Val Gln Pro Gln Gln Leu Pro Gln Phe Glu Glu
                245                 250                 255

Ile Arg Asn Leu Ala Leu Glu Thr Leu Pro Ala Met Cys Asn Val Tyr
                260                 265                 270

Ile Pro Pro Tyr Cys Thr Ile Ala Pro Val Gly Ile Phe Gly Thr Asn
                275                 280                 285

Tyr Arg
    290

<210> SEQ ID NO 72
<211> LENGTH: 33
<212> TYPE: PRT
<213> ORGANISM: Artificial Sequence
<220> FEATURE:
<223> OTHER INFORMATION: Synthetic

<400> SEQUENCE: 72

Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr Pro Gln Pro Gln Pro
                20                  25                  30

Phe

<210> SEQ ID NO 73
<211> LENGTH: 26
<212> TYPE: PRT
<213> ORGANISM: Artificial Sequence
<220> FEATURE:
<223> OTHER INFORMATION: Synthetic

<400> SEQUENCE: 73

Phe Leu Gln Pro Gln Gln Pro Phe Pro Pro Gln Gln Pro Gln Gln Pro
1               5                   10                  15

Tyr Pro Gln Gln Pro Gln Gln Pro Phe Pro
                20                  25
```

COMPOSITIONS AND METHODS FOR TREATING CELIAC SPRUE DISEASE

CROSS REFERENCE

This application is a continuation of U.S. application Ser. No. 15/633,065 filed Jun. 26, 2017, which is a continuation of U.S. application Ser. No. 15/006,341 filed Jan. 26, 2016, now U.S. Pat. No. 9,707,280 issued Jul. 18, 2017, which is a divisional of U.S. application Ser. No. 14/131,601 filed Feb. 26, 2014, now U.S. Pat. No. 9,289,473 issued Mar. 22, 2016, which is a US national stage filing of PCT Application Serial No. PCT/US2012/050364 filed Aug. 10, 2012, which claims priority to U.S. Provisional Application Ser. No. 61/521,899 filed on Aug. 10, 2011, each incorporated herein by reference in its entirety.

STATEMENT OF GOVERNMENT SUPPORT

This invention was made with government support under Defense Advanced Research Projects Agency (DARPA) grant number HR0011-08-1-0085. The government has certain rights in the invention.

BACKGROUND

Celiac sprue is a highly prevalent disease in which dietary proteins found in wheat, barley, and rye products known as 'glutens' evoke an immune response in the small intestine of genetically predisposed individuals. The resulting inflammation can lead to the degradation of the villi of the small intestine, impeding the absorption of nutrients. Symptoms can appear in early childhood or later in life, and range widely in severity, from diarrhea, fatigue and weight loss to abdominal distension, anemia, and neurological symptoms. There are currently no effective therapies for this lifelong disease except the total elimination of glutens from the diet. Although celiac sprue remains largely underdiagnosed, its' prevalence in the US and Europe is estimated at 0.5-1.0% of the population. The identification of suitable naturally-occurring enzymes as oral therapeutics for Celiac disease is difficult due to the stringent physical and chemical requirements to specifically and efficiently degrade gluten-derived peptides in the harsh and highly acidic environment of the human digestive tract.

SUMMARY

In a first aspect, the present invention provides polypeptides comprising an amino acid sequence at least 75% identical to an amino acid sequence according to SEQ ID NO:35, wherein
   (a) the polypeptide degrades a PQPQLP (SEQ ID NO:34) peptide at pH 4;
   (b) residue 278 is Ser, residue 78 is Glu, and residue 82 is Asp; and
   (c) the polypeptide comprises an amino acid change from SEQ ID NO: 67 at one or more residues selected from the group consisting of 73, 102, 103, 104, 130, 165, 168, 169, 172, and 179.

In a second aspect, the present invention provides polypeptide comprising an amino acid sequence at least 75% identical to an amino acid sequence according to SEQ ID NO:1, wherein
   (a) the polypeptide degrades a PQPQLP (SEQ ID NO:34) peptide at pH 4;
   (b) residue 467 is Ser, residue 267 is Glu, and residue 271 is Asp; and
   (c) the polypeptide comprises an amino acid change from SEQ ID NO: 33 at one or more residues selected from the group consisting of 119, 262, 291, 292, 293, 319, 354, 357, 358, 361, and 368.

In various embodiments of the first and second aspect, the polypeptide comprises an amino acid sequence at least 85%, 95%, or 100% identical to an amino acid sequence according to SEQ ID NO:1 or SEQ ID NO: 35. In another embodiment, the polypeptide, comprises an amino acid sequence according to any one of SEQ ID NO:2-66.

In another aspect, the present invention provides polypeptides comprising an amino acid sequence according to SEQ ID NO:1, wherein the polypeptide comprises at least one amino acid change from SEQ ID NO: 33. In another aspect, the present invention provides a polypeptide comprising an amino acid sequence according to SEQ ID NO:35, wherein the polypeptide comprises at least one amino acid change from SEQ ID NO: 67. In various embodiments, the polypeptide, comprises an amino acid sequence according to any one of SEQ ID NO:2-66.

In a further aspect, the present invention provides nucleic acids encoding the polypeptide of any aspect or embodiment of the invention. In another aspect, the invention provides nucleic acid expression vectors comprising the isolated nucleic acids of the invention. In a further embodiment, the invention provides recombinant host cells comprising the nucleic acid expression vectors of the invention. In another aspect, the invention provides pharmaceutical compositions, comprising the polypeptides, the nucleic acids, the nucleic acid expression vectors and/or the recombinant host cells of the invention, and a pharmaceutically acceptable carrier.

In another aspect, the invention provides methods for treating celiac sprue, comprising administering to an individual with celiac sprue a polypeptide or pharmaceutical composition according to any embodiment of the invention, or a polypeptide comprising an amino acid selected from the group consisting of SEQ ID NO:33 or SEQ ID NO:67.

Each protein was measured in triplicate and the error bars represent the standard deviation. Quantification was performed in ImageJ™.

Figure 4:
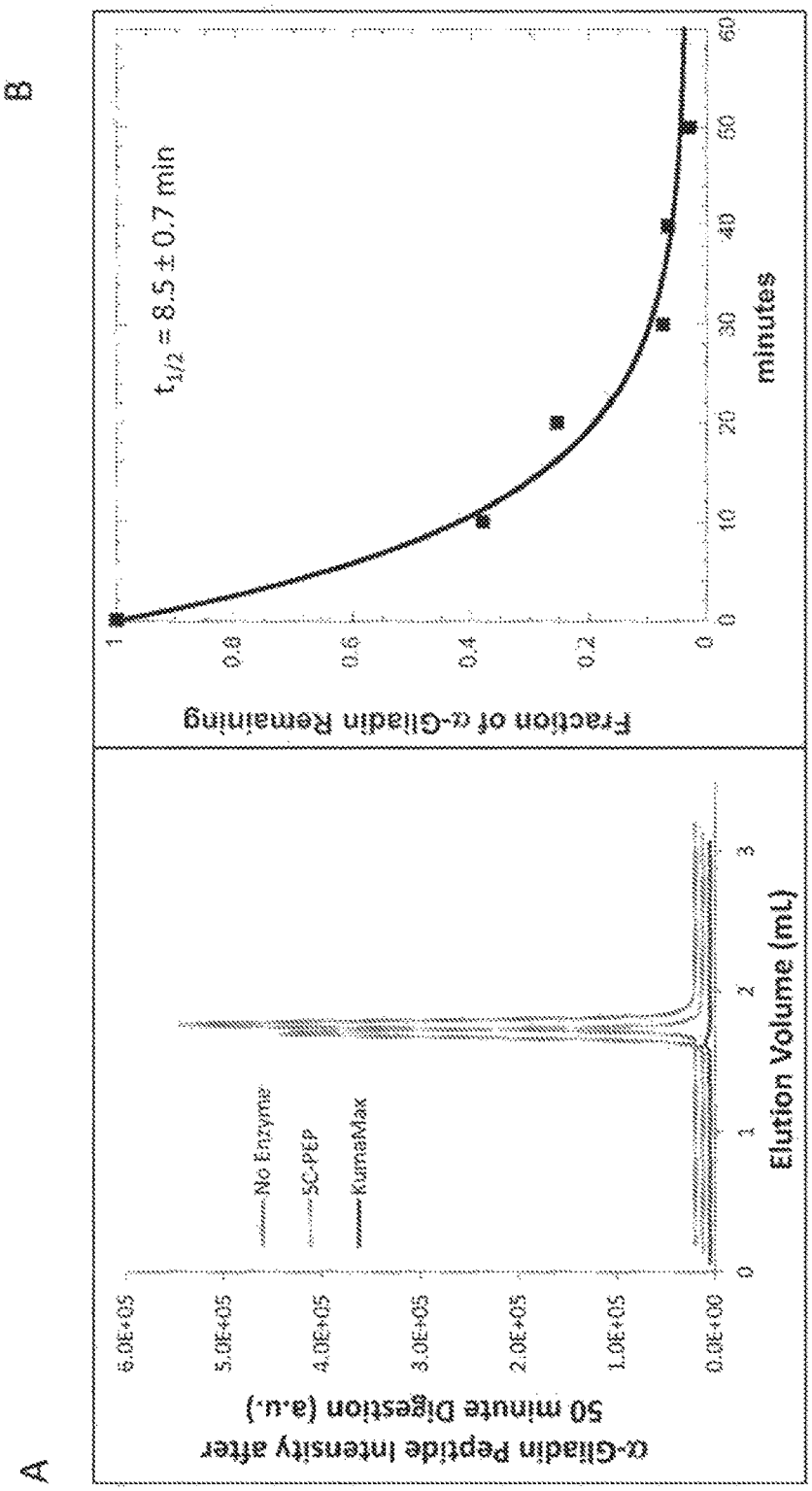

FIG. 4. An immunogenic α9-gliadin peptide is degraded by KUMAMAX™ polypeptide. A) Reaction chromatograms measuring the abundance of the M+H ion of the parent a9-gliadin peptide after 50 minutes of incubation with no enzyme, SC PEP, or KUMAMAX™ polypeptide. B) The fraction of α9-gliadin peptide remaining in the presence of KUMAMAX™ polypeptide as a function of incubation time at pH 4. The data was fit using a standard exponential decay function. The $R^2$ value was greater than 0.9.

DETAILED DESCRIPTION

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, $2^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

As used herein, amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

All embodiments of any aspect of the invention can be used in combination, unless the context clearly dictates otherwise.

In a first aspect, the present invention provides polypeptides comprising an amino acid sequence at least 75% identical to an amino acid sequence according to SEQ ID NO:35, wherein (a) the polypeptide degrades a PQPQLP (SEQ ID NO:34) peptide at pH 4;

(b) residue 278 is Ser, residue 78 is Glu, and residue 82 is Asp; and (c) the polypeptide comprises an amino acid change from SEQ ID NO: 67 at one or more residues selected from the group consisting of 73, 102, 103, 104, 130, 165, 168, 169, 172, and 179.

As disclosed in the examples that follow, polypeptides according to this aspect of the invention can be used, for example, in treating celiac sprue. The polypeptides are modified versions of either the processed version of Kumamolisin-As (SEQ ID NO:67) or the preprocessed version of Kumamolisin-As (SEQ ID NO:33), which is known as a member of the sedolisin family of serine-carboxyl peptidases, and utilizes the key catalytic triad $Ser^{278}$-$Glu^{78}$-$Asp^{82}$ in its processed form to hydrolyze its substrate ($Ser^{467}$-$Glu^{267}$-$Asp^{271}$ in the pre-processed form) Its maximal activity is at pH ~4.0. While the native substrate for Kumamolisin-As is unknown, it has been previously shown to degrade collagen under acidic conditions (4). In addition, this enzyme has been shown to be thermostable, with an ideal temperature at 60° C., but still showing significant activity at 37° C.

The inventors of the present invention have unexpectedly discovered that Kumamolisin-As is capable of degrading proline (P)- and glutamine (Q)-rich components of gluten known as 'gliadins' believed responsible for the bulk of the immune response in most celiac sprue patients. The polypeptides of the invention show improved protease activity at pH 4 against the oligopeptide PQPQLP (a substrate representative of gliadin) compared to wild type Kumamolisin-As.

The polypeptides of this aspect of the invention degrade a PQPQLP (SEQ ID NO:34) peptide at pH 4. Such degradation occurs under the conditions disclosed in the examples that follow.

The polypeptides of this aspect comprise one or more amino acid changes from SEQ ID NO: 67 (wild type processed Kumamolisin-As) at one or more residues selected from the group consisting of residues 73, 102, 103, 104, 130, 165, 168, 169, 172, and 179 (numbering based on the wild type processed Kumamolisin-As amino acid sequence). In non-limiting embodiments, the one or more changes relative to the wild type processed Kumamolisin-As amino acid sequence (SEQ ID NO:67) are selected from the group consisting of:

| WT Residue# | AA change |
|---|---|
| S73 | K, G |
| N102 | D |
| T103 | S |
| D104 | A, T, N |
| G130 | S |
| S165 | N |
| T168 | A |
| D169 | N, G |
| Q172 | D |
| D179 | S, H |

In various further non-limiting embodiments, the one or more changes relative to the wild type processed Kumamolisin-As amino acid sequence include at least N102D. In another embodiment the one or more changes relative to the wild type Kumamolisin-As amino acid sequence include at least N102D and D169N or D169G. In another embodiment the one or more changes relative to the wild type Kumamolisin-As amino acid sequence include at least N102D, D169G, and D179H. In another embodiment the one or more changes relative to the wild type Kumamolisin-As amino acid sequence include at least S73K, D104T, N102D, G130S, D169G, and D179H.

As used herein, "at least 75% identical" means that the polypeptide differs in its full length amino acid sequence by less 25% or less (including any amino acid substitutions, deletions, additions, or insertions) from the polypeptide defined by SEQ ID NO:35.

In various preferred embodiment, the polypeptide s comprise or consist of an amino acid sequence at least 76%, 77%, 78%, 79%, 80%, 81%, 82%, 83%, 84%, 85%, 86%, 87%, 88%, 89%, 90%, 91%, 92%, 92%, 93%, 94%, 95%, 96%, 97%, 98%, or 99% identical to an amino acid sequence according to SEQ ID NO:35. In a further embodiment the polypeptides comprise or consist of an amino acid sequence according to SEQ ID NO:35.

In various further embodiments, the polypeptides comprise or consist of an amino acid sequence at least 75% identical to any one of SEQ ID NOS:36-66. The polypeptides represented by these SEQ ID NOS are specific examples of polypeptides with improved protease activity at pH 4 against the oligopeptide PQPQLP (SEQ ID NO: 34) (a substrate representative of gliadin) compared to wild type Kumamolisin-As. In various preferred embodiment, the polypeptide s comprise or consist of an amino acid sequence at least 76%, 77%, 78%, 79%, 80%, 81%, 82%, 83%, 84%, 85%, 86%, 87%, 88%, 89%, 90%, 91%, 92%, 92%, 93%, 94%, 95%, 96%, 97%, 98%, or 99% identical to an amino acid sequence according to any one of SEQ ID NOS:36-66. In a further embodiment the polypeptides comprise or consist of an amino acid sequence according to any one of SEQ ID NOS:36-66.

In a preferred embodiment of this first aspect, the polypeptides comprising an amino acid sequence at least 75% identical to an amino acid sequence according to SEQ ID NO:1 (based on variants of the preprocessed version of Kumamolisin-As), wherein
  (a) the polypeptide degrades a PQPQLP (SEQ ID NO:34) peptide at pH 4;
  (b) residue 467 is Ser, residue 267 is Glu, and residue 271 is Asp; and
  (c) the polypeptide comprises an amino acid change from SEQ ID NO: 33 at one or more residues selected from the group consisting of 119, 262, 291, 292, 293, 319, 354, 357, 358, 361, and 368.

The polypeptides of this embodiment comprise one or more amino acid changes from SEQ ID NO: 33 (wild type pre-processed Kumamolisin-As) at one or more residues selected from the group consisting of residues 119, 262, 291, 292, 293, 319, 354, 357, 358, 361, and 368 (numbering based on the wild type pre-processed Kumamolisin-As amino acid sequence). In non-limiting embodiments, the one or more changes relative to the wild type Kumamolisin-As amino acid sequence are selected from the group consisting of:

| WT Residue# | AA change |
|---|---|
| V119 | D |
| S262 | K, G |
| N291 | D |
| T292 | S |
| D293 | A, T, N |
| G319 | S |
| S354 | N |
| T357 | A |
| D358 | N, G |
| Q361 | D |
| D368 | S, H |

In various further non-limiting embodiments, the one or more changes relative to the wild type Kumamolisin-As amino acid sequence include at least N291D. In another embodiment the one or more changes relative to the wild type Kumamolisin-As amino acid sequence include at least N291D and 358N or 358G. In another embodiment the one or more changes relative to the wild type Kumamolisin-As amino acid sequence include at least N291D, 358G, and 368H. In another embodiment the one or more changes relative to the wild type Kumamolisin-As amino acid sequence include at least V119D, S262K, D293T, N291D, G319S, D358G, and D368H.

As used herein, "at least 75% identical" means that the polypeptide differs in its full length amino acid sequence by less 25% or less (including any amino acid substitutions, deletions, additions, or insertions) from the polypeptide defined by SEQ ID NO:1.

In various preferred embodiment, the polypeptide s comprise or consist of an amino acid sequence at least 76%, 77%, 78%, 79%, 80%, 81%, 82%, 83%, 84%, 85%, 86%, 87%, 88%, 89%, 90%, 91%, 92%, 92%, 93%, 94%, 95%, 96%, 97%, 98%, or 99% identical to an amino acid sequence according to SEQ ID NO:1. In a further embodiment the polypeptides comprise or consist of an amino acid sequence according to SEQ ID NO:1.

In various further embodiments, the polypeptides comprise or consist of an amino acid sequence at least 75% identical to any one of SEQ ID NOS:2-32. The polypeptides represented by these SEQ ID NOS are specific examples of polypeptides with improved protease activity at pH 4 against the oligopeptide PQPQLP (SEQ ID NO: 34) (a substrate representative of gliadin) compared to wild type Kumamolisin-As. In various preferred embodiment, the polypeptide s comprise or consist of an amino acid sequence at least 76%, 77%, 78%, 79%, 80%, 81%, 82%, 83%, 84%, 85%, 86%, 87%, 88%, 89%, 90%, 91%, 92%, 92%, 93%, 94%, 95%, 96%, 97%, 98%, or 99% identical to an amino acid sequence according to any one of SEQ ID NOS:2-32. In a further embodiment the polypeptides comprise or consist of an amino acid sequence according to any one of SEQ ID NOS:2-32.

In a second aspect, the present invention provides polypeptides comprising or consisting of an amino acid sequence according to SEQ ID NO:35, wherein the polypeptide comprises at least one amino acid change from SEQ ID NO: 67. As disclosed in the examples that follow, polypeptides according to this aspect of the invention can be used, for example, in treating celiac sprue. The polypeptides are modified versions of processed Kumamolisin-As (SEQ ID NO:67), that show improved protease activity at pH 4 against the oligopeptide PQPQLP (SEQ ID NO: 34) (a substrate representative of gliadin) compared to wild type Kumamolisin-As. In one embodiment, the polypeptides comprise or consist of an amino acid sequence according to SEQ ID NO:36. Polypeptides according to SEQ ID NO:36 have a N102D mutation relative to wild-type processed Kumamolisin-As. As shown in the examples that follow, polypeptides containing this mutation have at least 10-fold improved protease activity at pH 4 against the oligopeptide PQPQLP (SEQ ID NO: 34) compared to wild type Kumamolisin-As.

In another embodiment of this second aspect, the polypeptides comprise or consist of an amino acid sequence according to SEQ ID NO:37. Polypeptides according to SEQ ID NO:37 have a N102D mutation and a D169N or D169G mutation relative to wild-type processed Kumamolisin-As. As shown in the examples that follow, polypeptides containing this mutation have at least 20-fold improved protease activity at pH 4 against the oligopeptide PQPQLP (SEQ ID NO: 34) compared to wild type Kumamolisin-As.

In another embodiment of this second aspect, the polypeptides comprise or consist of an amino acid sequence according to SEQ ID NO:38. Polypeptides according to SEQ ID NO:38 have a N102D mutation, a D169G, and a D179H mutation relative to wild-type processed Kumamolisin-As. As shown in the examples that follow, polypeptides containing this mutation have at least 50-fold improved protease activity at pH 4 against the oligopeptide PQPQLP (SEQ ID NO: 34) compared to wild type Kumamolisin-As.

In a further embodiment of this second aspect, the polypeptides comprise or consist of an amino acid sequence according to any one of SEQ ID NOS:39-66. Polypeptides according to these embodiments have all been demonstrated to show improved protease activity at pH 4 against the oligopeptide PQPQLP (SEQ ID NO: 34) compared to wild type Kumamolisin-As. In a preferred embodiment, the polypeptide comprises or consists of an amino acid sequence according to SEQ ID NO:66.

In a preferred embodiment of this second aspect, the present invention provides polypeptides comprising or consisting of an amino acid sequence according to SEQ ID NO:1, wherein the polypeptide comprises at least one amino acid change from SEQ ID NO: 33. As disclosed in the examples that follow, polypeptides according to this aspect of the invention can be used, for example, in treating celiac sprue. The polypeptides are modified versions of preprocessed Kumamolisin-As (SEQ ID NO:33), that show improved protease activity at pH 4 against the oligopeptide PQPQLP (SEQ ID NO: 34) (a substrate representative of gliadin) compared to wild type Kumamolisin-As. In one embodiment, the polypeptides comprise or consist of an amino acid sequence according to SEQ ID NO:2. Polypeptides according to SEQ ID NO:2 have a N291D mutation relative to preprocessed wild-type Kumamolisin-As. As shown in the examples that follow, polypeptides containing this mutation have at least 10-fold improved protease activity at pH 4 against the oligopeptide PQPQLP (SEQ ID NO: 34) compared to wild type Kumamolisin-As.

In another embodiment of this second aspect, the polypeptides comprise or consist of an amino acid sequence according to SEQ ID NO:3. Polypeptides according to SEQ ID NO:3 have a N291D mutation and a D358N or D358G mutation relative to preprocessed wild-type Kumamolisin-As. As shown in the examples that follow, polypeptides containing this mutation have at least 20-fold improved protease activity at pH 4 against the oligopeptide PQPQLP (SEQ ID NO: 34) compared to wild type Kumamolisin-As.

In another embodiment of this second aspect, the polypeptides comprise or consist of an amino acid sequence according to SEQ ID NO:4. Polypeptides according to SEQ ID NO:4 have a N291D mutation, a D358G, and a D368H mutation relative to preprocessed wild-type Kumamolisin-As. As shown in the examples that follow, polypeptides containing this mutation have at least 50-fold improved protease activity at pH 4 against the oligopeptide PQPQLP (SEQ ID NO: 34) compared to wild type Kumamolisin-As.

In a further embodiment of this second aspect, the polypeptides comprise or consist of an amino acid sequence according to any one of SEQ ID NOS:5-32. Polypeptides according to these embodiments have all been demonstrated to show improved protease activity at pH 4 against the oligopeptide PQPQLP (SEQ ID NO: 34) compared to wild type Kumamolisin-As. In a preferred embodiment, the polypeptide comprises or consists of an amino acid sequence according to SEQ ID NO:32; this polypeptide is shown in the examples that follow to possess the most potent protease activity at pH 4 against the oligopeptide PQPQLP (SEQ ID NO: 34) of any of the polypeptides tested.

As used throughout the present application, the term "polypeptide" is used in its broadest sense to refer to a sequence of subunit amino acids, whether naturally occurring or of synthetic origin. The polypeptides of the invention may comprise L-amino acids, D-amino acids (which are resistant to L-amino acid-specific proteases in vivo), or a combination of D- and L-amino acids. The polypeptides described herein may be chemically synthesized or recombinantly expressed. The polypeptides may be linked to other compounds to promote an increased half-life in vivo, such as by PEGylation, HESylation, PASylation, or glycosylation. Such linkage can be covalent or non-covalent as is understood by those of skill in the art. The polypeptides may be linked to any other suitable linkers, including but not limited to any linkers that can be used for purification or detection (such as FLAG or His tags).

In a third aspect, the present invention provides isolated nucleic acids encoding the polypeptide of any aspect or embodiment of the invention. The isolated nucleic acid sequence may comprise RNA or DNA. As used herein, "isolated nucleic acids" are those that have been removed from their normal surrounding nucleic acid sequences in the genome or in cDNA sequences. Such isolated nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the polypeptides of the invention.

In a fourth aspect, the present invention provides nucleic acid expression vectors comprising the isolated nucleic acid of any embodiment of the invention operatively linked to a suitable control sequence. "Recombinant expression vector" includes vectors that operatively link a nucleic acid coding region or gene to any control sequences capable of effecting expression of the gene product. "Control sequences" operably linked to the nucleic acid sequences of the invention are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type known in the art, including but not limited plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; *Gene Transfer and Expression Protocols*, pp. 109-128, ed. E. J. Murray, The Humana Press Inc., Clifton, N.J.), and the Ambion 1998 Catalog (Ambion, Austin, Tex.). The expression vector must be replicable in the host organisms either as an episome or by integration into host chromosomal DNA. In a preferred embodiment, the expression vector comprises a plasmid. However, the invention is intended to include other expression vectors that serve equivalent functions, such as viral vectors.

In a fifth aspect, the present invention provides recombinant host cells comprising the nucleic acid expression vectors of the invention. The host cells can be either prokaryotic or eukaryotic. The cells can be transiently or stably transfected or transduced. Such transfection and transduction of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, *Molecular Cloning: A Laboratory Manual* (Sambrook, et al., 1989, Cold Spring Harbor Laboratory Press; *Culture of Animal Cells: A Manual of Basic Technique, 2$^{nd}$ Ed.* (R. I. Freshney. 1987. Liss, Inc. New York, N.Y.). A method of producing a polypeptide according to the invention is an additional part of the invention. The method comprises the steps of (a) culturing a host according to this aspect of the invention under conditions conducive to the expression of the polypeptide, and (b) optionally, recovering the expressed polypeptide. The expressed polypeptide can be recovered from the cell free extract, cell pellet, or recovered from the culture medium. Methods to purify recombinantly expressed polypeptides are well known to the man skilled in the art.

In a sixth aspect, the present invention provides pharmaceutical compositions, comprising the polypeptide, nucleic acid, nucleic acid expression vector, and/or the recombinant host cell of any aspect or embodiment of the invention, and a pharmaceutically acceptable carrier. The pharmaceutical compositions of the invention can be used, for example, in the methods of the invention described below. The pharmaceutical composition may comprise in addition to the polypeptides, nucleic acids, etc. of the invention (a) a lyoprotectant; (b) a surfactant: (c) a bulking agent; (d) a tonicity adjusting agent: (e) a stabilizer; (f) a preservative and/or (g) a buffer.

In some embodiments, the buffer in the pharmaceutical composition is a Tris buffer, a histidine buffer, a phosphate buffer, a citrate buffer or an acetate buffer. The pharmaceutical composition may also include a lyoprotectant, e.g. sucrose, sorbitol or trehalose. In certain embodiments, the pharmaceutical composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the pharmaceutical composition includes a bulking agent, like glycine. In yet other embodiments, the pharmaceutical composition includes a surfactant e.g. polysorbate-20, polysorbate-40, polysorbate-60, polysorbate-65, polysorbate-80 polysorbate-85, poloxamer-188, sorbitan monolaurate, sorbitan monopalnutate, sorbitan monostearate, sorbitan monooleate, sorbitan trilaurate, sorbitan tristearate, sorbitan trioleaste, or a combination thereof. The pharmaceutical composition may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the pharmaceutical composition additionally includes a stabilizer, e.g., a molecule which, when combined with a protein of interest substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride.

The polypeptides, nucleic acids, etc. of the invention may be the sole active agent in the pharmaceutical composition, or the composition may further comprise one or more other active agents suitable for an intended use.

The pharmaceutical compositions described herein generally comprise a combination of a compound described herein and a pharmaceutically acceptable carrier, diluent, or excipient. Such compositions are substantially free of non-pharmaceutically acceptable components, i.e., contain amounts of non-pharmaceutically acceptable components lower than permitted by US regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablet, capsules, etc.).

These compositions can be prepared in a manner well known in the pharmaceutical art, and can be administered by any suitable route. In a preferred embodiment, the pharmaceutical compositions and formulations are designed for oral administration. Conventional pharmaceutical carriers, aqueous, powder or oily bases, thickeners and the like may be necessary or desirable.

The pharmaceutical compositions can be in any suitable form, including but not limited to tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

In a seventh aspect, the present invention provides methods for treating celiac sprue, comprising administering to an individual with celiac sprue an amount effective to treat the celiac sprue of one or more polypeptides selected from the group consisting of the polypeptides of the first or second aspects of the invention, SEQ ID NO:33, and SEQ ID NO:67.

The inventors of the present invention have unexpectedly discovered that Kumamolisin-As is capable of degrading proline (P)- and glutamine (Q)-rich components of gluten known as 'gliadins' believed responsible for the bulk of the immune response in most celiac sprue patients. The polypeptides of the invention show improved protease activity at pH 4 against the oligopeptide PQPQLP (SEQ ID NO: 34) (a substrate representative of gliadin) compared to wild type Kumamolisin-As.

In one embodiment, the one or more polypeptides comprise an amino acid sequence at least 75% identical to an amino acid sequence according to SEQ ID NO:35, wherein
(a) the polypeptide degrades a PQPQLP (SEQ ID NO:34) peptide at pH 4;
(b) residue 278 is Ser, residue 78 is Glu, and residue 82 is Asp.

In further embodiments, the one or more polypeptides comprise one or more amino acid changes from SEQ ID NO: 67 (wild type processed Kumamolisin-As) at one or more residues selected from the group consisting of residues 73, 102, 103, 104, 130, 165, 168, 169, 172, and 179 (numbering based on the wild type processed Kumamolisin-As amino acid sequence). In non-limiting embodiments, the one or more changes relative to the wild type processed Kumamolisin-As amino acid sequence (SEQ ID NO:67) are selected from the group consisting of:

| WT Residue# | AA change |
|---|---|
| S73 | K, G |
| N102 | D |
| T103 | S |
| D104 | A, T, N |
| G130 | S |
| S165 | N |
| T168 | A |
| D169 | N, G |
| Q172 | D |
| D179 | S, H |

In various further non-limiting embodiments, the one or more changes relative to the wild type processed Kumamolisin-As amino acid sequence include at least N102D. In another embodiment the one or more changes relative to the wild type Kumamolisin-As amino acid sequence include at least N102D and D169N or D169G. In another embodiment the one or more changes relative to the wild type Kumamolisin-As amino acid sequence include at least N102D, D169G, and D179H. In another embodiment the one or more changes relative to the wild type Kumamolisin-As amino acid sequence include at least S73K, D104T, N102D, G130S, D169G, and D179H.

In various preferred embodiment, the one or more polypeptide s comprise or consist of an amino acid sequence at least 76%, 77%, 78%, 79%, 80%, 81%, 82%, 83%, 84%, 85%, 86%, 87%, 88%, 89%, 90%, 91%, 92%, 92%, 93%, 94%, 95%, 96%, 97%, 98%, or 99% identical to an amino acid sequence according to SEQ ID NO:35. In a further embodiment the polypeptides comprise or consist of an amino acid sequence according to SEQ ID NO:35.

In various further embodiments, the one or more polypeptides comprise or consist of an amino acid sequence at least 75% identical to any one of SEQ ID NOS:36-66. The polypeptides represented by these SEQ ID NOS are specific examples of polypeptides with improved protease activity at pH 4 against the oligopeptide PQPQLP (SEQ ID NO: 34) (a substrate representative of gliadin) compared to wild type Kumamolisin-As. In various preferred embodiment, the polypeptide s comprise or consist of an amino acid sequence at least 76%, 77%, 78%, 79%, 80%, 81%, 82%, 83%, 84%, 85%, 86%, 87%, 88%, 89%, 90%, 91%, 92%, 92%, 93%, 94%, 95%, 96%, 97%, 98%, or 99% identical to an amino acid sequence according to any one of SEQ ID NOS:36-66. In a further embodiment the polypeptides comprise or consist of an amino acid sequence according to any one of SEQ ID NOS:36-66.

In a preferred embodiment, the polypeptides for use in the methods of this aspect of the invention comprise an amino acid according to SEQ ID NO:33 or a polypeptide comprising one or more amino acid changes from SEQ ID NO: 33 (wild type preprocessed Kumamolisin-As) at one or more residues selected from the group consisting of residues 119, 262, 291, 292, 293, 319, 354, 357, 358, 361, and 368 (numbering based on the wild type Kumamolisin-As amino acid sequence). In non-limiting embodiments, the one or more changes relative to the wild type Kumamolisin-As amino acid sequence are selected from the group consisting of:

| WT Residue# | AA change |
|---|---|
| V119 | D |
| S262 | K, G |
| N291 | D |
| T292 | S |
| D293 | A, T, N |
| G319 | S |
| S354 | N |
| T357 | A |
| D358 | N, G |
| Q361 | D |
| D368 | S, H |

In various further non-limiting preferred embodiments, the one or more changes relative to the wild type Kumamolisin-As amino acid sequence include at least N291D. In another embodiment the one or more changes relative to the wild type Kumamolisin-As amino acid sequence include at least N291D and 358N or 358G. In another embodiment the one or more changes relative to the wild type Kumamolisin-As amino acid sequence include at least N291D, 358G, and 368H. In another embodiment the one or more changes relative to the wild type Kumamolisin-As amino acid sequence include at least V119D, S262K, D293T, N291D, G319S, D358G, and D368H.

In various preferred embodiment, the polypeptide s for use in the methods of this aspect of the invention comprise or consist of an amino acid sequence at least 76%, 77%, 78%, 79%, 80%, 81%, 82%, 83%, 84%, 85%, 86%, 87%, 88%, 89%, 90%, 91%, 92%, 92%, 93%, 94%, 95%, 96%, 97%, 98%, or 99% identical to an amino acid sequence according to SEQ ID NO:1. In a further embodiment the polypeptides comprise or consist of an amino acid sequence according to SEQ ID NO:1.

In various further embodiments, the polypeptides for use in the methods of this aspect of the invention comprise or consist of an amino acid sequence at least 75% identical to any one of SEQ ID NOS:2-32. The polypeptides represented by these SEQ ID NOS are specific examples of polypeptides with improved protease activity at pH 4 against the oligopeptide PQPQLP (SEQ ID NO: 34) (a substrate representative of gliadin) compared to wild type Kumamolisin-As. In various preferred embodiment, the polypeptides for use in the methods of this aspect of the invention comprise or consist of an amino acid sequence at least 76%, 77%, 78%, 79%, 80%, 81%, 82%, 83%, 84%, 85%, 86%, 87%, 88%, 89%, 90%, 91%, 92%, 92%, 93%, 94%, 95%, 96%, 97%, 98%, or 99% identical to an amino acid sequence according to any one of SEQ ID NOS:2-32. In a further embodiment the polypeptides comprise or consist of an amino acid sequence according to any one of SEQ ID NOS:2-32.

In an eighth aspect, the present invention provides methods for treating celiac sprue, comprising administering to an individual with celiac sprue a polypeptide comprising an amount effective of amino acid sequence according to any one of SEQ ID NOS: 1-67 to treat the celiac sprue.

In one embodiment, the polypeptides administered comprise or consist of an amino acid sequence according to SEQ ID NO:2. Polypeptides according to SEQ ID NO:2 have a N291D mutation relative to wild-type Kumamolisin-As. As shown in the examples that follow, polypeptides containing this mutation have at least 10-fold improved protease activity at pH 4 against the oligopeptide PQPQLP (SEQ ID NO: 34) compared to wild type Kumamolisin-As.

In another embodiment of this second aspect, the polypeptides administered comprise or consist of an amino acid sequence according to SEQ ID NO:3. Polypeptides according to SEQ ID NO:3 have a N291D mutation and a D358N or D358G mutation relative to wild-type Kumamolisin-As.

As shown in the examples that follow, polypeptides containing this mutation have at least 20-fold improved protease activity at pH 4 against the oligopeptide PQPQLP (SEQ ID NO: 34) compared to wild type Kumamolisin-As.

In another embodiment of this second aspect, the polypeptides administered comprise or consist of an amino acid sequence according to SEQ ID NO:4. Polypeptides according to SEQ ID NO:4 have a N291D mutation, a D358G, and a D368H mutation relative to wild-type Kumamolisin-As. As shown in the examples that follow, polypeptides containing this mutation have at least 50-fold improved protease activity at pH 4 against the oligopeptide PQPQLP (SEQ ID NO: 34) compared to wild type Kumamolisin-As.

In a further embodiment of this second aspect, the polypeptides administered comprise or consist of an amino acid sequence according to any one of SEQ ID NOS:5-32. Polypeptides according to these embodiments have all been demonstrated to show improved protease activity at pH 4 against the oligopeptide PQPQLP (SEQ ID NO: 34) compared to wild type Kumamolisin-As. In a preferred embodiment, the polypeptide administered comprises or consists of an amino acid sequence according to SEQ ID NO:32; this polypeptide is shown in the examples that follow to possess the most potent protease activity at pH 4 against the oligopeptide PQPQLP (SEQ ID NO: 34) of any of the polypeptides tested.

In another embodiment, the one or more polypeptides comprise an amino acid sequence according to SEQ ID NO:36. Polypeptides according to SEQ ID NO:36 have a N102D mutation relative to wild-type processed Kumamolisin-As. As shown in the examples that follow, polypeptides containing this mutation have at least 10-fold improved protease activity at pH 4 against the oligopeptide PQPQLP (SEQ ID NO: 34) compared to wild type Kumamolisin-As. In another embodiment, the one or more polypeptides comprise an amino acid sequence according to SEQ ID NO:37. Polypeptides according to SEQ ID NO:37 have a N102D mutation and a D169N or D169G mutation relative to wild-type processed Kumamolisin-As. As shown in the examples that follow, polypeptides containing this mutation have at least 20-fold improved protease activity at pH 4 against the oligopeptide PQPQLP (SEQ ID NO: 34) compared to wild type Kumamolisin-As. In another embodiment, the one or more polypeptides comprise an amino acid sequence according to SEQ ID NO:38. Polypeptides according to SEQ ID NO:38 have a N102D mutation, a D169G, and a D179H mutation relative to wild-type processed Kumamolisin-As. As shown in the examples that follow, polypeptides containing this mutation have at least 50-fold improved protease activity at pH 4 against the oligopeptide PQPQLP (SEQ ID NO: 34) compared to wild type Kumamolisin-As. In further embodiments, the one or more polypeptides comprise an amino acid sequence according to any one of SEQ ID NOS:39-66. Polypeptides according to these embodiments have all been demonstrated to show improved protease activity at pH 4 against the oligopeptide PQPQLP (SEQ ID NO: 34) compared to wild type Kumamolisin-As. In a preferred embodiment, the polypeptide comprises or consists of an amino acid sequence according to SEQ ID NO:66.

Celiac sprue (also known as celiac disease or gluten intolerance) is a highly prevalent disease in which dietary proteins found in wheat, barley, and rye products known as 'glutens' evoke an immune response in the small intestine of genetically predisposed individuals. The resulting inflammation can lead to the degradation of the villi of the small intestine, impeding the absorption of nutrients. Symptoms can appear in early childhood or later in life, and range widely in severity, from diarrhea, fatigue, weight loss, abdominal pain, bloating, excessive gas, indigestion, constipation, abdominal distension, nausea/vomiting, anemia, bruising easily, depression, anxiety, growth delay in children, hair loss, dermatitis, missed menstrual periods, mouth ulcers, muscle cramps, joint pain, nosebleeds, seizures, tingling or numbness in hands or feet, delayed puberty, defects in tooth enamel, and neurological symptoms such as ataxia or paresthesia. There are currently no effective therapies for this lifelong disease except the total elimination of glutens from the diet. Although celiac sprue remains largely underdiagnosed, its' prevalence in the US and Europe is estimated at 0.5-1.0% of the population.

As used herein, "treating celiac sprue" means accomplishing one or more of the following: (a) reducing the severity of celiac sprue; (b) limiting or preventing development of symptoms characteristic of celiac sprue; (c) inhibiting worsening of symptoms characteristic of celiac sprue; (d) limiting or preventing recurrence of celiac sprue in patients that have previously had the disorder; (e) limiting or preventing recurrence of symptoms in patients that were previously symptomatic for celiac sprue; and (f) limiting development of celiac sprue in a subject at risk of developing celiac sprue, or not yet showing the clinical effects of celiac sprue.

The individual to be treated according to the methods of the invention may be any individual suffering from celiac sprue, including human subjects. The individual may be one already suffering from symptoms or one who is asymptomatic.

As used herein, an "amount effective" refers to an amount of the polypeptide that is effective for treating celiac sprue. The polypeptides are typically formulated as a pharmaceutical composition, such as those disclosed above, and can be administered via any suitable route, including orally, parentally, by inhalation spray, or topically in dosage unit formulations containing conventional pharmaceutically acceptable carriers, adjuvants, and vehicles. In a preferred embodiment, the pharmaceutical compositions and formulations are orally administered, such as by tablets, pills, lozenges, elixirs, suspensions, emulsions, solutions, or syrups.

Dosage regimens can be adjusted to provide the optimum desired response (e.g., a therapeutic or prophylactic response). A suitable dosage range may, for instance, be 0.1 ug/kg-100 mg/kg body weight; alternatively, it may be 0.5 ug/kg to 50 mg/kg; 1 ug/kg to 25 mg/kg, or 5 ug/kg to 10 mg/kg body weight. The polypeptides can be delivered in a single bolus, or may be administered more than once (e.g., 2, 3, 4, 5, or more times) as determined by an attending physician.

Examples

Figure 1:
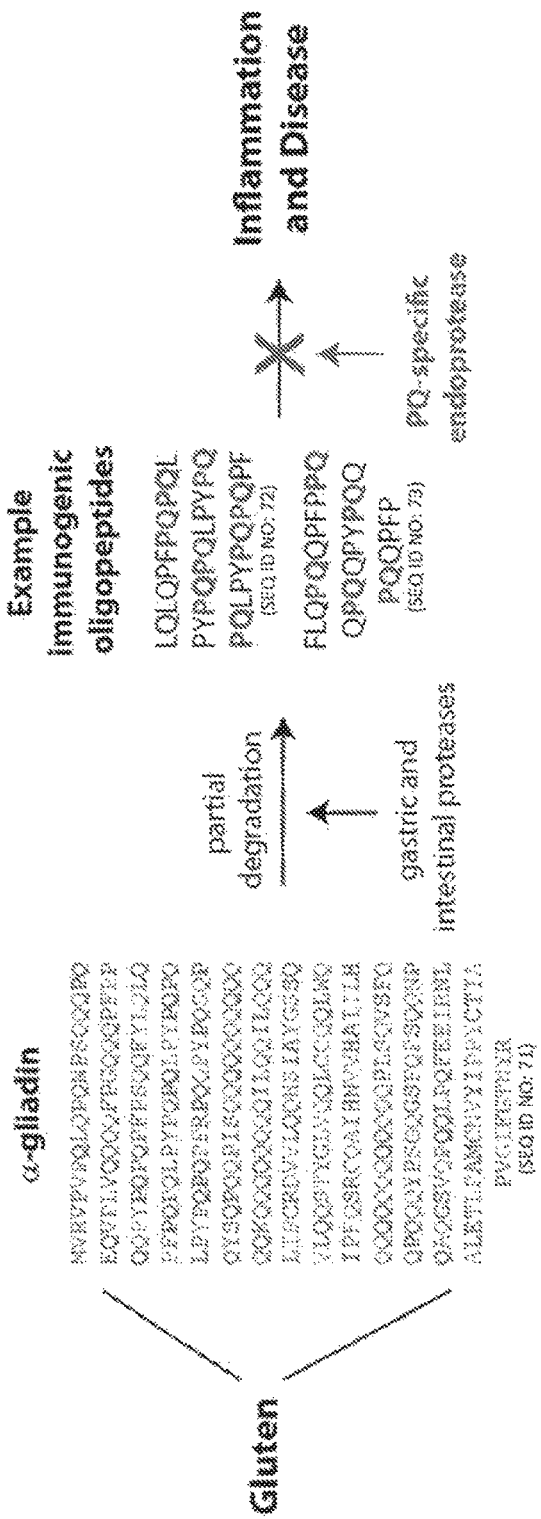
FIG. 1. Schematic depicting the role of enzyme therapeutics in the treatment of Celiac disease. Gluten is comprised of many glycoproteins including α-gliadin. Partial proteolysis of α-gliadin (SEQ ID NO: 71) results in protease-resistant peptides enriched in a PQ dipeptide motif that can lead to inflammation and disease. The addition of an oral enzyme therapeutic that is functional in the stomach and capable of specifically degrading the immunogenic peptides could potentially act as a therapeutic for this disease.

Celiac disease is an autoimmune disorder that afflicts approximately 1% of the population[1,2]. This disease is characterized by an inflammatory reaction to gluten, the major protein in wheat flour, and to related proteins in barley and rye[2]. Gluten is composed of a heterogeneous mixture of the glycoproteins gliadin and glutenin[3]. Upon ingestion, α-gliadin is partially degraded by gastric and intestinal proteases to oligopeptides, which are resistant to further proteolysis due to their unusually high proline and glutamine content[3] (FIG. 1). Immunogenic oligopeptides that result from incomplete proteolysis are enriched in the PQ motif[4,5] (FIG. 1), which stimulate inflammation and injury in the intestine of people with Celiac disease. Currently the only treatment for this disease is complete elimination of gluten from the diet, which is difficult to attain due to the ubiquity of this protein in modern food products[6].

Oral enzyme therapy (OET) in which orally administered proteases are employed to hydrolyze immunogenic peptides before they are capable of triggering inflammation is currently being explored as a treatment for gluten intolerance.

For this purpose, several different proteases have been considered due to their specificity for cleavage after either proline or glutamine residues[4,7-9]. However, these enzymes often demonstrate characteristics that hinder their use in OET for gluten degradation. Most of these peptidases exhibit optimal catalytic activity at neutral pH; however, the pH of the human stomach ranges from 2 to 4. These enzymes are therefore most active when they reach the pH-neutral small intestine, which is too late for effective prevention of Celiac disease as this is the site where gluten-derived pathology develops[2,10]. Additionally, several of these enzymes demonstrate instability in the low pH of the human stomach, are susceptible to proteolysis by digestive proteases, or require extensive refolding procedures during their purification[7,11], which are all characteristics that hamper efforts for clinical use.

The ideal protease for the application of OET in the treatment of gluten intolerance would combine the following traits: optimal activity at low pH, easy purification, stability under the conditions of the human stomach, and high specificity for amino acid motifs found in gluten-derived immunogenic oligopeptides. Here we report the engineering of an endopeptidase that demonstrates these traits. We identified a protease that is highly active in acidic conditions, Kumamolisin-As (KumaWT) from the acidophilic bacterium *Alicyclobacillus sendaiensis*, and used computational modeling tools to engineer it toward the desired oligopeptide specificity. The computationally designed enzyme, designated KUMAMAX™ polypeptide, exhibited over 100-fold increased proteolytic activity and an 800-fold switch in substrate specificity for the targeted PQ motif compared to wild-type KumaWT. In addition, KUMA-MAX™ polypeptide demonstrates resistance to common gastric proteases and is produced at high yields in *E. coli* without the need for refolding. Thus, this protease and others reported herein represent promising therapeutic candidates for Celiac disease.

Results

Selection and Computational Design of an α-Gliadin Endopeptidase

In order to engineer a novel protease that can degrade gluten peptides under gastric conditions, we first focused on identifying an appropriate protease as a starting point for our engineering efforts. Ideally, the template protease would combine stability and activity at low pH with demonstrated specificity for a dipeptide amino acid motif. We identified the enzyme Kumamolisin-As (KumaWT) as a template, since this protease naturally has an optimal activity over the pH range of 2-4[12], which matches the approximate pH ranges in the human stomach before and after a meal is ingested (pH 2 and 4, respectively)[13]. KumaWT also demonstrates high stability and activity at the physiologically relevant temperature 37° C.[14]. In addition, the purification of this enzyme is straightforward and yields significant quantities using standard recombinant protein production methods in *E. coli*[14], an important property both for screening mutant libraries and for its ultimate generation in large batches for use in OET. Finally, KumaWT naturally recognizes a specific dipeptide motif as opposed to single amino acid specificity[14]. This is an important property for an oral protease therapeutic meant to be taken during digestion, since dipeptide specificity should result in reduced competitive inhibition by other food-derived peptides in the stomach.

An effective OET for Celiac disease would likely demonstrate specificity for Proline-Glutamine (PQ), due to the frequent occurrence of this dipeptide in immunogenic gluten-derived oligopeptides (FIG. 1). KumaWT has a strong specificity for proline at the P2 position of its peptide substrate, matching one of the amino acid residues of interest for the degradation of immunogenic α-gliadin peptides. In the P1 site, KumaWT has been established to prefer the positively charged amino acids arginine or lysine[14]. Despite this preference, KumaWT is also capable of recognizing glutamine at the P1 position, albeit at a significantly decreased level compared to its recognition of arginine or lysine[14]. This slight innate proclivity to recognize glutamine at the P1 position suggests that KumaWT may be amenable to re-engineering to prefer glutamine at this position. At the P1' site, KumaWT demonstrates broad specificity, which is desirable since the residue in the position after the PQ motif varies among the different immunogenic peptides, as depicted in FIG. 1.

Given these characteristics of KumaWT, our primary goal was to computationally redesign the S1 binding pocket of KumaWT such that it would prefer a PQ dipeptide motif over the native PR or PK substrates. Using the Rosetta Molecular Modeling Suite, we modeled the PR dipeptide in the S1 binding pocket of KumaWT using this enzyme's solved crystal structure (PDB ID: 1T1E). This revealed that two negatively-charged amino acids, D358 and D368, likely facilitate binding of the positively charged amino acids in the P1 position (FIG. 2A). The native specificity for proline at P2 appears to be derived in large part from a hydrophobic interaction of this amino acid residue with the aromatic ring of W318 in the S2 pocket of the enzyme. As specificity of the P1 position for proline is desired in our enzyme variant, we maintained this native tryptophan during the design of the S1 pocket.

To redesign the KumaWT substrate specificity of the S1 pocket to prefer glutamine at the P1 position, we generated theoretical mutations in the KumaWT binding pocket using the Foldit interface to the Rosetta Molecular Modeling Suite. A tetrapeptide that represents a common immunogenic motif found throughout α-gliadin, PQLP (SEQ ID NO: 68), was modeled into the P2 to P2' active site positions. This structure already contained a polypeptide bound in the active site, so the residues of this polypeptide were mutated using Rosetta to the PQLP (SEQ ID NO: 68) tetrapeptide motif. A total of 75 residues within an 8 Å sphere of the tetrapeptide were randomized to any of the 20 naturally occurring amino acids in order to find mutations that would favor binding of glutamine in the S1 pocket. These mutations were accepted if the overall energy of the new enzyme-PQLP substrate complex was either reduced relative to the native substrate, or was not increased by more than 5 Rosetta energy units. To accommodate the smaller, neutral amino acid glutamine, we focused our computational efforts on 1) removing the negative charge of the S1 pocket during the design process, 2) filling in open space that resulted from the replacement of the large amino acid arginine with glutamine, and 3) providing hydrogen bonds to the amide functional group of the glutamine. This computational modeling yielded 107 novel designs containing from 1 to 7 simultaneous mutations. These designed proteins were then constructed and their catalytic activity against a PQLP (SEQ ID NO: 68) peptide was assessed.

In order to test the activity of each of these designed proteases against the PQLP (SEQ ID NO: 68) motif, the desired mutations were incorporated into the native nucleotide sequence using site directed mutagenesis, and mutant enzyme variants were produced in *E. coli* BL21(DE3) cells. These enzyme variants were then screened for enzymatic activity in clarified whole cell lysates at pH 4 using the fluorescently quenched α-gliadin hexapeptide analogue QXL520-PQPQLP-K(5-FAM)-NH2 (FQ) (SEQ ID NO: 69) as a substrate. Of the 107 enzyme variants tested in this assay, 13% resulted in a loss of enzymatic function, 32% did not demonstrate a significant difference in activity relative to KumaWT, and 55% resulted in an increase in observed activity against this substrate. Twenty-eight of the most promising enzyme variants that exhibited a significant increase in activity in cell lysates were then purified in order to obtain an accurate comparison of enzymatic activity to that of KumaWT. After purification and correction for protein concentration, the activities of these enzymes ranged from 2-fold to 120-fold more active than KumaWT (Table 1). The most active variant, which was named KUMAMAX™ polypeptide, was selected for further characterization.

TABLE 1

Fold change in hydrolytic activity on PQ motif of all purified and sequenced mutants, relative to wild type Kumamolysin-As. These are the fold-change results (calculated as described in Supplementary Table 1) for all mutants that were purified, sequenced, and tested against wild-type Kumamolysin in the pure protein assay. The assay took place at pH 4, with enzyme final concentration of 0.0125 mg/mL and substrate concentration of 5 μM.

| Mutations to Wild Type Kumamolysin-As (Preprocessed) | Fold Change in Activity of PQ Hydrolysis Relative to Wild Type Kumamolysin-As |
|---|---|
| Wild Type (WT) | 1.0 |
| T357A | 2.0 |
| G319S, D368S | 2.0 |
| D358G | 3.0 |
| D293A | 3.0 |
| D358N | 4.0 |
| G319S, S354N, D358G, D368H | 5.0 |
| D358G, D368H | 6.0 |
| G319S, D358G, D368H | 7.0 |
| N291D, Q361D | 7.5 |
| S354N, D358G, D368H | 9.0 |
| N291D | 10.0 |
| N291D, D293A, Q361D, D358N | 14.8 |
| N291D, D293A | 15.0 |
| N291D, D293A, D358G, Q361D | 15.0 |
| N291D, D358N | 18.9 |
| N291D, Q361D, D358G | 20.0 |
| N291D, G319S, D358G, Q361D, D368H | 23.1 |
| N291D, D293A, D358N | 24.0 |
| S262G, T292S, N291D, G319S, D358G, D368H | 29.0 |
| N291D, D293A, G319S, D358G, Q361D, D368H | 40.9 |
| T292S, N291D, G319S, D358G, D368H | 49.0 |
| N291D, G319S, S354N, D358G, Q361D, D368H | 50.0 |
| N291D, G319S, S354N, D358G, D368H | 54.6 |
| N291D, D293A, G319S, S354N, D358G, Q361D, D368H | 58.0 |
| D293T, N291D, G319S, D358G, D368H | 58.0 |
| S262K, D293N, N291D, G319S, D358G, D368H | 62.0 |
| N291D, G319S, D358G, D368H | 93.0 |
| V119D, S262K, D293T, N291D, G319S, D358G, D368H | 120.0 |

Figure 2:
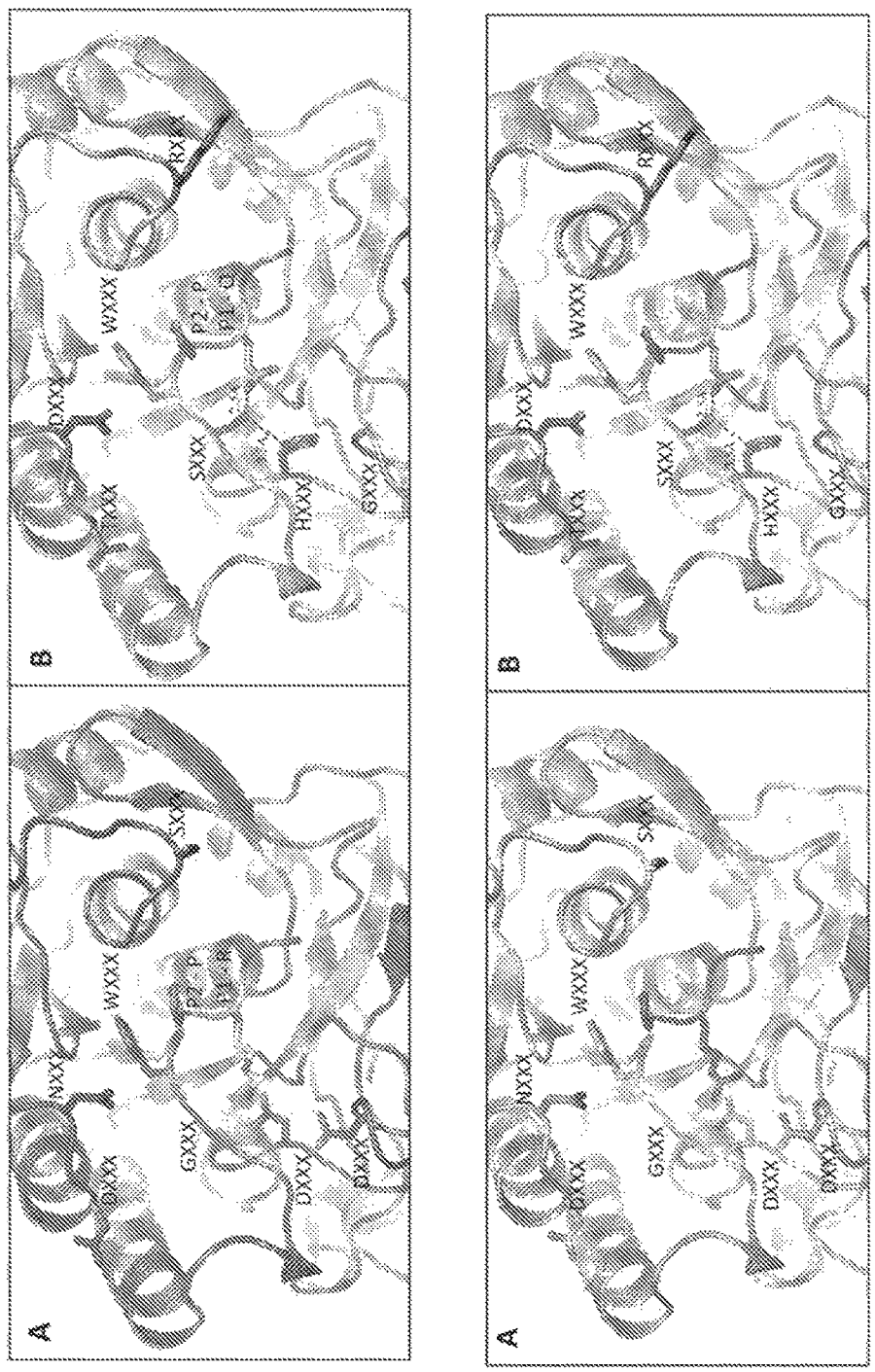
FIG. 2. Computational models of the peptide binding sites for KumaWT and KUMAMAX™ polypeptide. A) KumaWT in complex with a PR dipeptide motif. B) KUMAMAX™ polypeptide in complex with the designed PQ dipeptide motif. Computationally designed residues in the active site are labeled and highlighted in sticks. The modeled peptides were based on a bound form of Kumamolisin-AS (PDB ID: 1T1E) and final structures were generated using the Rosetta Molecular Modeling Suite. Images were generated using PyMol v1.5.

KUMAMAX™ polypeptide contains seven mutations from the wild-type amino acid sequence: V119D, S262K, N291D, D293T, G319S, D358G, D368H (FIG. 2B). Of these, the mutations G319S, D358G, and D368H appear to synergistically introduce a new hydrogen bond with the desired glutamine residue at position P1. As modeled, the G319S mutation appears to introduce a hydroxyl group that is located 2.5 Å from the carbonyl oxygen of the glutamine amide, potentially contributing a new hydrogen bond that interacts with glutamine in the P1 pocket. The D368H mutation is predicted to stabilize the serine hydroxyl, and its position in the active site is in turn sterically allowed by the D358G mutation. In addition to providing a novel desired interaction with glutamine as modeled, these three mutations also remove the two acidic residues predicted to stabilize the positively charged arginine residue in the native KumaWT substrate (FIG. 2). V119D, which was unexpectedly incorporated during site directed mutagenesis, is located in the propeptide domain and therefore does not affect catalytic activity of the mature enzyme. The other three mutations do not make direct contacts with residues in the P2-P2' pockets, and therefore likely introduce interactions with other components of the hexapeptide, the fluorophore, or the quencher. It is clear that these mutations are important for the overall catalytic enhancement observed, as the G319S/D358G/D368H triple mutant alone demonstrated only a 7-fold increase in catalytic activity over KumaWT; roughly 17-fold lower than that determined for KUMAMAX™ polypeptide.

Kinetic Characterization and Substrate Specificity

The catalytic efficiencies for KUMAMAX™ polypeptide and KumaWT against the FQ immunogenic gluten substrate analogue, as calculated by fitting a velocity versus substrate curve over 6-100 μM substrate, were found to be 568 $M^{-1}$ $s^{-1}$ and 4.9 $M^{-1}$ $s^{-1}$, respectively (Table 2) These values are consistent with the observation that KUMAMAX™ polypeptide demonstrated a 120-fold increase in enzymatic activity towards the FQ substrate in the initial activity screen mentioned above. Unfortunately, no significant saturation of velocity at these substrate concentrations was observed, and therefore the individual kinetic constants $k_{cat}$ and $K_M$ could not be determined. This is not surprising since previous analyses of the kinetic constants of KumaWT report a Km of 40 μM. Therefore, no significant saturation would be expected at substrate concentrations less than 100 μM.

TABLE 2

Kinetic Constants of peptide substrates for KUMAMAX™ polypeptide and KumaWT. The catalytic efficiency ($k_{cat}/K_M$ $M^{-1}s^{-1}$) for both KumaWT and KUMAMAX™ polypeptide for the fluorescently (Fl) quenched (Qu) PQPQLP (SEQ ID NO: 34) peptide was fit to a linear curve as no saturation was observed up to 100 μM substrate. The fluorescence signal was quantified as described in Materials and Methods with a standard curve that accounted for substrate quenching of product fluorescence. The catalytic efficiency for the pNA-linked peptides was determined in a similar manner, and is described in the Materials and Methods. All fits had at least six independently measured rates with an $R^2$ greater than 0.9. n.d. not detected.

| | Catalytic Efficiency $M^{-1}s^{-1}$ | | | | |
|---|---|---|---|---|---|
| | Qu-PQPQLP-Fl | Suc-APQ-pNA | Suc-APR-pNA | Suc-APE-pNA | Suc-AQP-pNA |
| KumaWT | 4.9 ± 0.2 | n.d. | 131.8 ± 3.8 | 4.0 ± 0.1 | n.d. |
| KUMAMAX™ polypeptide | 568.5 ± 14.6 | 6.7 ± 0.4 | n.d. | 1.4 ± 0.2 | n.d. |

While the increased activity of KUMAMAX™ polypeptide compared to KumaWT against the fluorescently quenched PQPQLP (SEQ ID NO: 34)hexapeptide substrate suggests that KUMAMAX™ polypeptide has increased preference for a PQ dipeptide motif, it does not report directly on substrate specificity. To confirm that the specificity of KUMAMAX™ polypeptide had indeed been altered to prefer the PQ dipeptide over the native PR dipeptide of KumaWT, four peptides in the form of Succinyl-Alanine-P2-P1-P1' were provided as substrates to both enzymes in order to assess P2 and P1 specificity. These peptides contained the reporter p-nitroaniline (pNA) at the P1' position, which allows for a spectrometric readout of peptide cleavage. The four peptides harbored the following amino acids at the P2 and P1 positions, respectively: proline-glutamine (PQ), proline-arginine (PR), glutamine-proline (QP), and proline-glutamate (PE). Catalytic efficiencies were calculated for each substrate and are reported in Table 2. As in the determination of catalytic activities against the FQ substrate, no saturation of activity on these peptides by KumaWT or KUMAMAX™ polypeptide was observed. This suggests that the pNA group may partially disrupt binding in the P1' pocket, since substrate concentrations up to 1 mM were tested, well beyond saturation levels previously reported for alternative KumaWT substrates.

In this specificity assay, KUMAMAX™ polypeptide demonstrated its highest level of activity on the PQ substrate, the dipeptide that it had been designed to prefer. While KUMAMAX™ polypeptide was not explicitly designed to demonstrate a decrease in specificity for the PR motif or for other motifs, its increased specificity for PQ could decrease its activity for non-targeted motifs. Indeed, KUMAMAX™ polypeptide exhibited no significant catalytic activity against the QP or PR substrates in this assay (Table 2). Consistent with previous reports[14], KumaWT exhibited its highest level of activity on the PR motif. KumaWT demonstrated significantly lower levels of activity on the three other peptide substrates. While catalytic activity of KumaWT on the PQ dipeptide motif has previously been reported[14], no significant activity on the PQ dipeptide substrate was observed in this assay, which may be due to disruptive effects of pNA on the binding of this peptide to the enzyme active site. Both enzymes demonstrated activity towards the isosteric substrate PE, which is predicted to have neutral charge at pH 4; however, KUMAMAX™ polypeptide demonstrated a roughly 5-fold decrease in activity on the PE peptide substrate compared to its activity on the PQ substrate, which illustrates its exquisite selectivity for the PQ dipeptide motif.

As discussed previously, there are several enzymes currently being explored as OET for Celiac disease. Two of these enzymes are engineered forms of the prolyl endopeptidase SC PEP and the glutamine-specific endoprotease EP-B2[15]. To compare the catalytic efficiencies of these proteases to that of KUMAMAX™ polypeptide, the native SC PEP and EP-B2 enzymes were expressed in *E. coli* BL21(DE3) cells, purified, and their catalytic activities assessed. SC-PEP demonstrated a catalytic efficiency of 1.6 $M^{-1} s^{-1}$ on the FQ gluten substrate analogue at pH 4, which represents a roughly 350-fold lower level of activity on this substrate than KUMAMAX™ polypeptide. At pH 4, SC PEP did not exhibit any significant activity on any of the four pNA linked peptide substrates, including QP. Although previous studies using similar pNA-linked peptides have demonstrated activity of SC PEP on these substrates, those assays were performed at a pH of 4.5 or higher[15]. Like other groups, we found that SC PEP demonstrated significant levels of activity on the QP substrate at pH 7, with a catalytic efficiency of 2390 $M^{-1} s^{-1}$, thereby confirming that this recombinant SC PEP was fully functional (data not shown). This is consistent with previous literature reporting that SC PEP has low to negligible levels of catalytic activity in the pH range of the stomach, and is thus only expected to be effective once α-gliadin peptides have reached the small intestine[15,16].

For EP-B2, only very low levels of activity were detected on the FQ substrate at pH 4, and no activity on any of the four pNA peptide substrates was observed (data not shown). This is inconsistent with previous reports of EP-B2 activity using comparable substrates[11]. EP-B2 is a difficult enzyme to purify, as it forms inclusion bodies in *E. coli* and requires refolding to obtain active enzyme. We were unable to obtain soluble protein using previously reported methods for the refolding of EP-B2[11,17,18], so we used an on-column refolding process which resulted in soluble protein produced. Although this soluble EP-B2 demonstrated the expected self-processing activity at pH 4[11] (data not shown), the lack of activity of this enzyme suggests that it may not have refolded properly using our methods. This could be due to alternative N and C-terminal tags arising from the use of different protein expression vectors and warrants further investigation.

Protease Stability

In addition to demonstrating catalytic activity at low pH, any protein therapeutic intended for use in the human digestive tract must exhibit resistance to degradation by digestive proteases. Two of the most abundant proteases in the stomach and small intestine are pepsin and trypsin, respectively. Pepsin demonstrates optimal proteolytic activity at the low pH range of the stomach, while trypsin is primarily active at the more neutral pH of the small intestine. To assess the resistance of KUMAMAX™ polypeptide to degradation by these proteases, 0.01 or 0.1 mg/mL of KUMAMAX™ polypeptide were incubated with each protease, in their respective optimal pH ranges, at 0.1 mg/mL, which is a physiologically relevant concentration of both pepsin and trypsin. SC PEP and EP-B2 were included as controls, as EP-B2 has been established to be resistant to pepsin but susceptible to trypsin, and SC PEP demonstrates susceptibility to both proteases[11,15]. Each protein was incubated in the presence or absence of the respective protease for 30 minutes, after which the proteins were heat inactivated and the remaining non-proteolyzed fraction determined using an SDS-PAGE gel (FIG. 3).

Figure 3:
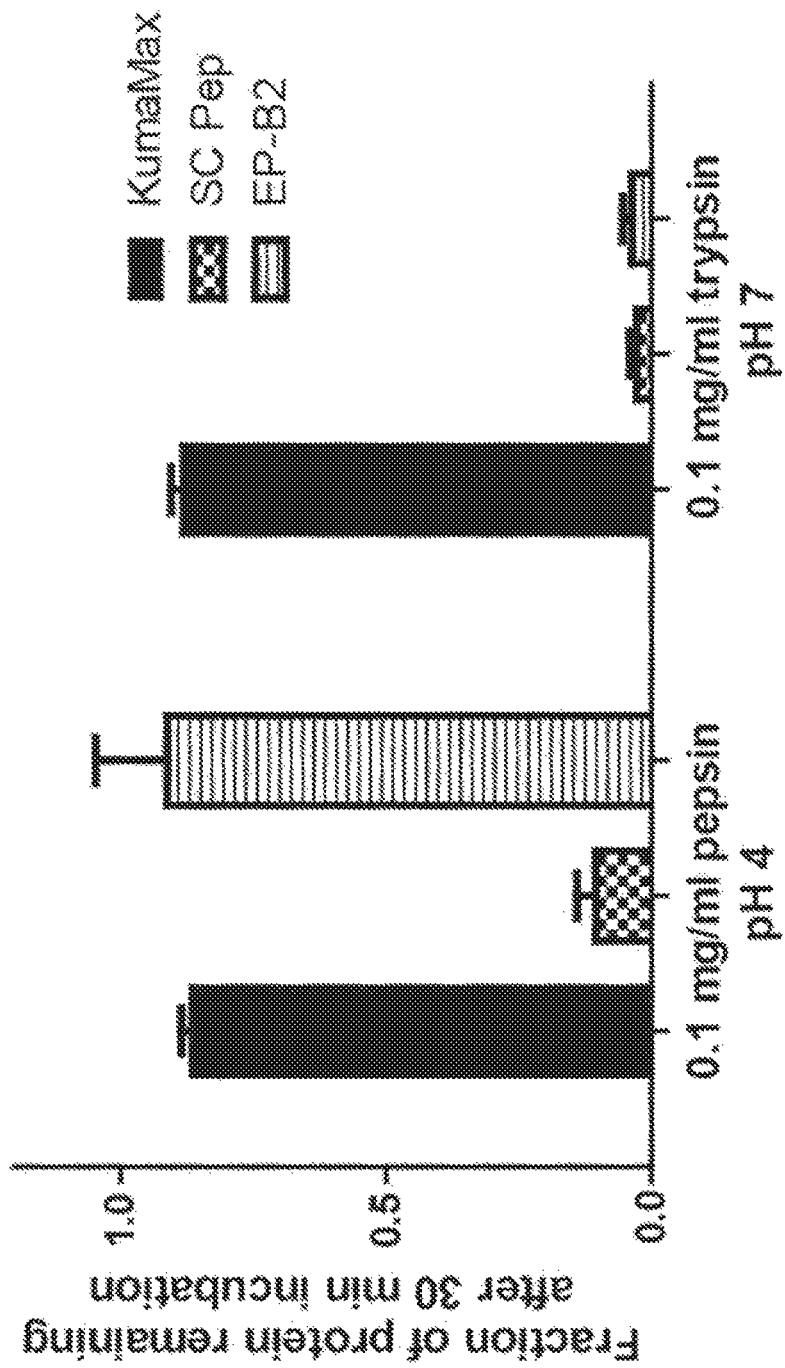
FIG. 3. Protein stability after incubation with pepsin or trypsin. Stability was measured by quantifying the relative remaining fraction of intact protein as observed on an SDS-PAGE gel after 30 minutes of incubation in the presence or absence of pepsin or trypsin at the pH indicated.

In this assay, KUMAMAX™ polypeptide demonstrated high stability against both pepsin and trypsin, with roughly 90% intact protein remaining after the half hour incubation with either protease (FIG. 3). Consistent with previous reports, SC PEP exhibited susceptibility to both pepsin and trypsin, with less than 20% of the enzyme remaining after incubation with these proteases. As expected, trypsin efficiently proteolyzed EP-B2 with less than 10% remaining after incubation, but no significant degradation of EP-B2 was observed in the presence of pepsin. To confirm that observed protein degradation was due to protease activity and not to enzymatic self-processing, each enzyme was incubated at either pH 4 or 7 and apparent proteolysis was analyzed in the absence of other proteases over the course of an hour (data not shown). KUMAMAX™ polypeptide and EP-B2, but not SC PEP, demonstrated self-processing from the pro-peptide to the active enzyme form in fewer than 10 minutes at pH 4. All three proteins remained >90% stable over the course of the hour. None of these proteins showed significant levels of self-processing or proteolysis during incubation for one hour at pH 7.

Degradation of an Immunogenic α9-Gliadin Peptide

The significant level of catalytic activity exhibited by KUMAMAX™ polypeptide on immunogenic peptide analogues (Table 2) demonstrates promise for the use of KUMAMAX™ polypeptide as a therapeutic in OET for gluten intolerance. However, these assays do not directly assess the ability of this enzyme to degrade relevant immunogenic peptides derived from gluten. Therefore, we examined the direct proteolytic activity of KUMAMAX™ polypeptide towards an immunodominant peptide present in α9-gliadin, QLQPFPQPQLPY (SEQ ID NO: 70).

KUMAMAX™ polypeptide was incubated with 500 μM of the α9-gliadin peptide at 37° C. in pH 4 at roughly a 1:100 enzyme to peptide molar ratio, which represents a physiologically relevant concentration of this peptide in the human stomach. SC PEP was included in this experiment for the sake of comparison, since this enzyme demonstrates significantly less activity against the FQ substrate than KUMAMAX™ polypeptide. Samples from the incubation were quenched every 10 minutes in 80% acetonitrile to halt the proteolysis reaction. The remaining fraction of intact immunogenic peptide was determined using high-performance liquid-chromatography mass spectroscopy, in which the M+H parent ion of the α9-gliadin peptide was monitored. KUMAMAX™ polypeptide demonstrated a high level of activity against the immunogenic peptide in this assay, as over 95% of the immunogenic peptide had been proteolyzed after a 50 minute incubation with KUMAMAX™ polypeptide, while no significant degradation of the peptide was observed in the presence of SC PEP or in the absence of protease (FIG. 4A). The half-life of the peptide in the presence of KUMAMAX™ polypeptide was determined by plotting the fraction of peptide remaining against the incubation time, and was calculated to be 8.5±0.7 minutes (FIG. 4B).

Discussion

Enzyme therapy is an attractive method for the treatment of Celiac disease since this form of treatment would not require intravenous injection. However, it is a challenge to identify an appropriate protease for use in OET that demonstrates all the properties necessary to be an effective therapeutic for Celiac disease. Specifically, an ideal protease for use in OET would maintain activity in a pH range from 2-4 at 37° C. and would resist degradation by common digestive proteases. In addition, the protein therapeutic would ideally demonstrate stringent specificity for a common motif found in immunogenic gluten-derived peptides. Finally, the protein should be easily produced using recombinant methods. While it is unlikely that a single natural enzyme will encompass all of these properties, we demonstrate that a protein containing several of these important characteristics can be engineered to demonstrate the lacking qualities through computational analysis, mutagenesis, and screening.

The engineered protease, KUMAMAX™ polypeptide, demonstrated a high level of activity on, and specificity towards, the desired PQ dipeptide motif (Table 2). The specificity for the PQ motif, as opposed to the native PR motif, potentially derives from the addition of new hydrogen bonds in the S1 pocket of KUMAMAX™ polypeptide that, as modeled, make direct contacts with the glutamine in this dipeptide motif (FIG. 2B). This specificity switch not only directs activity against a motif found commonly throughout gluten, but it also greatly decreases activity against non-targeted substrates (Table 2). The inability for an oral protease to recognize non-targeted substrates is an important characteristic as it reduces competitive inhibition by the large number of other peptides produced in the stomach during digestion of a meal. KUMAMAX™ polypeptide or KumaWT can potentially act as platforms for engineering greater specificity, as KumaWT has demonstrated some level of selectivity beyond the P2 and P1 sites[14]. Using this method, a panel of customized proteases specific for unique immunogenic epitopes could be generated.

Methods

Protein Expression and Purification

The genes encoding each protein of interest, harbored in the pET29b plasmid, were transformed into *Escherichia coli* BL21 (DE3) cells. Individual colonies were picked, inoculated into Terrific Broth™ with 50 μg/μL Kanamycin (TB+Kan), and incubated overnight at 37° C. 500 uL of the overnight culture was added to 500 mL autoinduction media (5 g tryptone, 2.5 g yeast extract, 465 mL ddH$_2$O), and shaken at 37° C. for roughly 4 hours, then the autoinduction components were added (500 uL MgSO$_4$, 500 uL 1000× trace metals, 25 mL 20×NPS, 10 mL 20×5052, 500 uL 50 mg/mL Kan). The cultures were then shaken at 18° C. for 30 hours before being spun down. Pellets were resuspended in 10 mL 1×PBS, then lysed via sonication with 5 mL lysis buffer (50 mM HEPES, 500 mM NaCl, 1 mM bME, 2 mg/mL lysozyme, 0.2 mg/mL DNase, ddH$_2$O) and spun down. The proteins were then purified over 1 mL TALON cobalt affinity columns. KUMAMAX™ polypeptide, KumaWT, and SC Pep were washed three times with 20 mL wash buffer (10 mM imidazole, 50 mM HEPES, 500 mM NaCl, 1 mM bME, ddH$_2$O), and then eluted in 15 mL of elution buffer (200 mM imidazole, 50 mM HEPES, 500 mM NaCl, 1 mM bME). EP-B2 had to be refolded on the column, so after lysis the pellets were resuspended in 10 mL of EP-B2 buffer, which differs from the wash buffer only in that it is diluted in guanidine hydrochloride instead of ddH$_2$O to allow for denaturation of the EP-B2 inclusion bodies. This resuspension was pelleted, and the supernatant (containing denatured EP-B2) was filtered with a 0.8 μm filter onto the column. EP-B2 was washed once with 20 mL of the EP-B2 buffer, before being washed twice with 20 mL of the wash buffer to refold the protein on the column. Protein was eluted with 15 ml of the elution buffer. All proteins were concentrated from 15 mL down to ~500 uL, then dialyzed once in 1 L dialysis buffer (20% glycerol, 50 mM HEPES, 500 mM NaCl, 1 mM bME). Protein concentration was calculated spectrophotometrically with extinction coefficients of 53,985 $M^{-1}$ $cm^{-1}$ for KumaWT and all KumaWT variants, 152,290 $M^{-1}$ $cm^{-1}$ for SC Pep, and 58,245 $M^{-1}$ $cm^{-1}$ for EP-B2.

Screening Method

Kunkel mutagenesis was used to generate mutations to KumaWT. Individual colonies picked from plates were grown up in 96-deep well plates. After lysing the cells with Triton buffer (1% 100× Triton, 1 mg/mL lysozyme, 0.5 mg/mL DNase, 1×PBS), the supernatant was adjusted to pH 4 with a 100 mM sodium acetate buffer. To crudely screen for activity against the FQ substrate, 10 uL of supernatant was added to 90 uL of 5 μM substrate in a 96-well black plate, and the fluorescence was measured at 30-second intervals for 1 hour.

Purified Enzyme Assay

The variants of Kumamolisin-As that displayed the most activity on the FQ substrate in the activity screen were sequenced, then purified in small scale. 500 uL of TB+Kan overnight cultures were added to 50 mL TB+Kan and grown at 37° C. until reaching an optical density of 0.5-0.8. IPTG was added to 0.5 mM, and the cultures were expressed at 22° C. for 16-24 hours. The cells were spun down, resuspended in 500 uL of wash buffer (1×PBS, 5 mM imidazole, ddH$_2$O), transferred to a 2 mL Eppendorf tube, and lysed in 1 mL lysis buffer (1×PBS, 5 mM imidazole, 2× Bug Buster™, 2 mg/mL lysozyme, 0.2 mg/mL DNase, ddH$_2$O). After centrifugation, the supernatant was decanted into a fresh tube. Columns with 200 uL of TALON cobalt resin were placed in Eppendorf tubes, and the supernatant was poured over the columns and rocked for 20 minutes before spinning down and discarding the flow-through. The proteins were washed three times with 500 uL wash buffer, discarding the flow-through between washes. Enzymes were eluted in 200 uL elution buffer (1×PBS, 200 mM imidazole, dd H$_2$O), and concentrations were calculated spectrophotometrically using an extinction coefficient of 53,985 $M^{-1}$ $cm^{-1}$.

For the assay, the Kumamolisin-As mutants were incubated for 15 minutes in pH 4 100 mM sodium acetate buffer. Enzyme was added to 5 µM substrate so that the final protein concentration was 0.0125 mg/mL. The fluorescence was measured at 30-second intervals for 1 hour.

Kinetic Characterization

Enzyme variant proclivity for gluten degradation was measured by hydrolysis of the fluorescently quenched α-gliadin hexapeptide analogue QXL520-PQPQLP-K(5-FAM)-NH2 (FQ) (SEQ ID NO: 69) as a substrate. Each enzyme was incubated at room temperature for 15 minutes in 100 mM pH 4 sodium acetate buffer. After 15 minutes, 50 uL of fluorescent substrate was added ranging in final concentration between 100, 50, 25, 12.5, 6.25, and 0 µM peptide, and maintaining concentrations of 0.05 µM KUMAMAX™ polypeptide, 0.5 µM KumaWT, 0.5 µM SC Pep, and 0.5 µM EP-B2 across all variations in substrate concentration. The plate was read immediately on the spectrophotometer for an hour, using 455 nm wavelength for excitation and reading 485 nm wavelength for emission.

The enzymes were also tested for specificity to different dipeptide motifs using a variety of chromogenic substrates that release p-nitroaniline (pNA) upon hydrolysis: [Suc-APQ-pNA], [Suc-AQP-pNA], [Suc-APE-pNA], and [Suc-APR-pNA]. Again, each enzyme was incubated at room temperature for 15 minutes in 100 mM pH 4 sodium acetate buffer. After 15 minutes, 20 uL of substrate was added to the enzyme incubation so that the final concentrations of substrate ranged between 1000, 500, 250, 125, 62.5, 31.25, 15.625, and 0 µM, and all enzymes being tested ended in a concentration of 0.5 µM. The plate was read immediately on the spectrophotometer for an hour, monitoring absorption by the reactions at 385 nm.

The standard curve for the fluorescent peptide involved mixing substrate and product together at varying concentrations in pH 4 buffer. Substrate concentrations were 100, 50, 25, 12.5, 6.25, and 0 µM, and product concentrations were 20, 5, 1.25, 0.3125, 0.078125, 0 µM.

The standard curve for the absorbent peptide involved product concentrations of 100, 50, 25, 12.5, 6.25, 3.125, 1.5625, 0.78125, 0.390625, 0.1953125, 0.09765625, and 0 µM diluted in pH 4 buffer.

Protease Stability

Enzyme stability was determined in the presence the digestive proteases, pepsin and trypsin. KumaWT, KUMAMAX™ polypeptide, SC Pep, and EP-B2 were incubated in buffer matching the native pH environment of each digestive protease. pH 3.5 100 mM sodium acetate was used to pre-incubate the enzymes for pepsin digestion assays, and pH 7.5 dialysis buffer (see "Protein Expression and Purification") for the trypsin digestion assays. Each experimental enzyme was incubated at 37° C. for 15 minutes in each buffer, at a concentration of 0.2 mg/mL.

After pre-incubation in the appropriate buffer, 0.1 mg/mL digestive protease was added. The reactions were done in triplicate, and were incubated at 37° C. for 30 minutes. Adding SDS and boiling for 5 minutes ensured digestive protease inactivation. An SDS-PAGE gel allowed quantification of enzyme degradation, using ImageJ.

The rate of protein self-proteolysis was determined at pH 4 and 7.5 in the absence of pepsin or trypsin. Each enzyme, at a concentration of 0.2 mg/mL, was incubated in pH 4 100 mM sodium acetate and pH 7.5 dialysis buffer. At 20, 40, and 60 minutes, timepoints were taken. SDS was added, and the aliquots were boiled for 5 minutes to ensure denaturation of the enzymes and inhibition of further self-proteolysis. Again, an SDS-PAGE gel in conjunction with ImageJ allowed quantification of enzyme self-proteolysis.

LCMS Gliadin Degradation Assay

Enzyme activity on full-length α9-gliadin was measured using high-performance liquid-chromatography mass spectrometry. For each enzyme, 7 µL of pH 4 1M sodium acetate buffer was added to 28 µL of 5 µM enzyme, and incubated alongside separate tubes of 3 µL gliadin at 37° C. for 15 minutes. Next 27 µL of each enzyme mixture, and 27 µL of dialysis buffer as a control, were added to each tube of gliadin. These were incubated once more at 37° C., and 5 µL samples were taken at 10, 20, 30, 40, and 50 minutes. Each timepoint sample was quenched in 95 µL of 80% acetonitrile with 1% formic acid and approximately 33 µM leupeptin. The samples were analyzed on the HPLC to compare gliadin degradation by the different proteases over time.

REFERENCES

1. Armstrong, M. J., Hegade, V. S. & Robins, G. Advances in coeliac disease. *Curr Opin Gastroenterol* 28, 104-12 (2012).
2. Sollid, L. M. Coeliac disease: dissecting a complex inflammatory disorder. *Nat Rev Immunol* 2, 647-55 (2002).
3. Wieser, H. Chemistry of gluten proteins. *Food Microbiol* 24, 115-9 (2007).
4. Shan, L. et al. Structural basis for gluten intolerance in celiac sprue. *Science* 297, 2275-9 (2002).
5. Shan, L. Identification and analysis of multivalent proteolytically resistant peptides from gluten: implications for celiac sprue. *Journal of Proteome Research* (2005).
6. Chand, N. & Mihas, A. A. Celiac disease: current concepts in diagnosis and treatment. *J Clin Gastroenterol* 40, 3-14 (2006).
7. Shan, L., Marti, T., Sollid, L. M., Gray, G. M. & Khosla, C. Comparative biochemical analysis of three bacterial prolyl endopeptidases: implications for coeliac sprue. *Biochem J* 383, 311-8 (2004).
8. Siegel, M. et al. Rational design of combination enzyme therapy for celiac sprue. *Chem Biol* 13, 649-58 (2006).
9. Stepniak, D. et al. Highly efficient gluten degradation with a newly identified prolyl endoprotease: implications for celiac disease. *Am J Physiol Gastrointest Liver Physiol* 291, G621-9 (2006).
10. Ehren, J. et al. A food-grade enzyme preparation with modest gluten detoxification properties. *PLoS One* 4, e6313 (2009).
11. Bethune, M. T., Strop, P., Tang, Y., Sollid, L. M. & Khosla, C. Heterologous expression, purification, refolding, and structural-functional characterization of EP-B2, a self-activating barley cysteine endoprotease. *Chem Biol* 13, 637-47 (2006).
12. Okubo, A. et al. Processing, catalytic activity and crystal structures of kumamolisin-As with an engineered active site. *FEBS J* 273, 2563-76 (2006).
13. Gardner, J. D., Ciociola, A. A. & Robinson, M. Measurement of meal-stimulated gastric acid secretion by in vivo gastric autotitration. *J Appl Physiol* 92, 427-34 (2002).
14. Wlodawer, A. et al. Crystallographic and biochemical investigations of kumamolisin-As, a serine-carboxyl peptidase with collagenase activity. *J Biol Chem* 279, 21500-10 (2004).
15. Ehren, J., Govindarajan, S., Moron, B., Minshull, J. & Khosla, C. Protein engineering of improved prolyl endopeptidases for celiac sprue therapy. *Protein Eng Des Sel* 21, 699-707 (2008).
16. Bethune, M. T. & Khosla, C. Oral enzyme therapy for celiac sprue. *Methods Enzymol* 502, 241-71 (2012).
17. Gass, J., Vora, H., Bethune, M. T., Gray, G. M. & Khosla, C. Effect of barley endoprotease EP-B2 on gluten digestion in the intact rat. *J Pharmacol Exp Ther* 318, 1178-86 (2006).
18. Vora, H., McIntire, J., Kumar, P., Deshpande, M. & Khosla, C. A scaleable manufacturing process for pro-EP-B2, a cysteine protease from barley indicated for celiac sprue. *Biotechnol Bioeng* 98, 177-85 (2007).

We claim:

1. A method of degrading gliadin in a meal ingested by an individual in need of such treatment, said method comprising the step of orally administering to said individual a therapeutically effective dose of a pharmaceutical composition comprising a polypeptide comprising an amino acid sequence at least 85% identical to the amino acid sequence of SEQ ID NO:35 residues 1-378, and a pharmaceutically acceptable carrier; wherein (a) the polypeptide degrades a PQPQLP (SEQ ID NO:34) peptide at pH 4;

(b) residue 278 is Ser, residue 78 is Glu, and residue 82 is Asp according to the amino acid residue position of SEQ ID NO:35; and (c) the polypeptide comprises an amino acid change from SEQ ID NO: 67 residues 1-378 at one or more residues selected from the group consisting of amino acid residues 73, 102, 103, 104, 130, 165, 168, 169, 172, and 179;

wherein said treatment reduces exposure of said individual to immunogenic gliadin peptides.

2. The method of claim 1, wherein the pharmaceutical composition is administered during digestion.

3. The method of claim 1, wherein the pharmaceutical composition is administered within 15 minutes of ingestion of a meal.

4. The method of claim 1, wherein the pharmaceutical composition is administered within 10, 20, 30, 40, or 50 minutes of ingestion of a meal.

5. The method of claim 1, wherein the meal comprises gluten.

6. The method of claim 1, wherein the meal comprises one or more ingredients selected from the group consisting of wheat, barley, and rye.

7. The method of claim 1, comprising an amino acid sequence at least 90% identical to the amino acid sequence of SEQ ID NO:35 residues 1-378.

8. The method of claim 1, wherein the polypeptide comprises the amino acid sequence of any one of SEQ ID NO:36-66 residues 1-378.

9. The method of claim 1, wherein the polypeptide comprises the amino acid sequence of SEQ ID NO:66 residues 1-378.

10. The method of claim 1, wherein the one or more amino acid changes are selected from the group consisting of:
residue 102: D,
residue 103: S;
residue 104: A, T, and N;
residue 130: S;
residue 165: N;
residue 168: A;
residue 169: N, and G;
residue 172: D; and
residue 179: S, and H.

11. The method of claim 1, wherein if the amino acid change is at residue 73, the residue 73 amino acid is not N.

12. The method of claim 1, wherein the amino acid change from SEQ ID NO:67 is at one or more residues selected from the group consisting of amino acid residues 102, 103, and 104.

13. The method of claim 1, wherein the amino acid change from SEQ ID NO:67 is at one or more residues selected from the group consisting of amino acid residues 130, 165, 168, and 169.

14. The method of claim 1, wherein the amino acid change from SEQ ID NO:67 is at amino acid residue 179.

15. The method of claim 1, wherein the amino acid change from SEQ ID NO:67 is at amino acid residue 73 and the residue 73 is not N.

16. A method of treating an inflammatory reaction to gluten in an individual in need thereof, said method comprising the step of administering to said individual a therapeutically effective dose of a pharmaceutical composition comprising a polypeptide comprising an amino acid sequence at least 85% identical to the amino acid sequence of SEQ ID NO:35 residues 1-378, and a pharmaceutically acceptable carrier; wherein
(a) the polypeptide degrades a PQPQLP (SEQ ID NO:34) peptide at pH 4;
(b) residue 278 is Ser, residue 78 is Glu, and residue 82 is Asp according to the amino acid residue position of SEQ ID NO:35; and
(c) the polypeptide comprises an amino acid change from SEQ ID NO: 67 residues 1-378 at one or more residues selected from the group consisting of amino acid residues 73, 102, 103, 104, 130, 165, 168, 169, 172, and 179.

17. The method of claim 16, wherein the pharmaceutical composition is administered during digestion.

18. The method of claim 16, wherein the pharmaceutical composition is administered orally.

19. The method of claim 16, comprising an amino acid sequence at least 90% identical to the amino acid sequence of SEQ ID NO:35 residues 1-378.

20. The method of claim 16, wherein the polypeptide comprises the amino acid sequence of any one of SEQ ID NO:36-66 residues 1-378.

21. The method of claim 16, wherein the polypeptide comprises the amino acid sequence of SEQ ID NO:66 residues 1-378.

22. The method of claim 16, wherein the one or more amino acid changes are selected from the group consisting of:
residue 102: D,
residue 103: S;
residue 104: A, T, and N;
residue 130: S;
residue 165: N;
residue 168: A;
residue 169: N, and G;
residue 172: D; and
residue 179: S, and H.

23. The method of claim 16, wherein if the amino acid change is at residue 73, the residue 73 amino acid is not N.

24. The method of claim 16, wherein the amino acid change from SEQ ID NO:67 is at one or more residues selected from the group consisting of amino acid residues 102, 103, and 104.

25. The method of claim 16, wherein the amino acid change from SEQ ID NO:67 is at one or more residues selected from the group consisting of amino acid residues 130, 165, 168, and 169.

26. The method of claim 16, wherein the amino acid change from SEQ ID NO:67 is at amino acid residue 179.

27. The method of claim 16, wherein the amino acid change from SEQ ID NO:67 is at amino acid residue 73 and the residue 73 is not N.

28. A method of treating gluten intolerance in an individual in need thereof, said method comprising the step of administering to said individual a therapeutically effective dose of a pharmaceutical composition comprising a polypeptide comprising an amino acid sequence at least 85% identical to the amino acid sequence of SEQ ID NO:35 residues 1-378, and a pharmaceutically acceptable carrier; wherein
(a) the polypeptide degrades a PQPQLP (SEQ ID NO:34) peptide at pH 4;
(b) residue 278 is Ser, residue 78 is Glu, and residue 82 is Asp according to the amino acid residue position of SEQ ID NO:35; and
(c) the polypeptide comprises an amino acid change from SEQ ID NO: 67 residues 1-378 at one or more residues selected from the group consisting of amino acid residues 73, 102, 103, 104, 130, 165, 168, 169, 172, and 179.

29. The method of claim 28, wherein the pharmaceutical composition is administered during digestion.

30. The method of claim 28, wherein the pharmaceutical composition is administered orally.

31. The method of claim 28, comprising an amino acid sequence at least 90% identical to the amino acid sequence of SEQ ID NO:35 residues 1-378.

32. The method of claim 28, wherein the polypeptide comprises the amino acid sequence of any one of SEQ ID NO:36-66 residues 1-378.

33. The method of claim 28, wherein the one or more amino acid changes are selected from the group consisting of:
  residue 102: D,
  residue 103: S;
  residue 104: A, T, and N;
  residue 130: S;
  residue 165: N;
  residue 168: A;
  residue 169: N, and G;
  residue 172: D; and
  residue 179: S, and H.

34. The method of claim 28, wherein if the amino acid change is at residue 73, the residue 73 amino acid is not N.

35. The method of claim 28, wherein the amino acid change from SEQ ID NO:67 is at one or more residues selected from the group consisting of amino acid residues 102, 103, and 104.

36. The method of claim 28, wherein the amino acid change from SEQ ID NO:67 is at one or more residues selected from the group consisting of amino acid residues 130, 165, 168, and 169.

37. The method of claim 28, wherein the amino acid change from SEQ ID NO:67 is at amino acid residue 179.

38. The method of claim 28, wherein the amino acid change from SEQ ID NO:67 is at amino acid residue 73 and the residue 73 is not N.

\* \* \* \* \*